(12) United States Patent
Vogel et al.

(10) Patent No.: US 7,387,715 B2
(45) Date of Patent: *Jun. 17, 2008

(54) SAMPLE POSITIONING AND ANALYSIS SYSTEM

(75) Inventors: Horst Vogel, Préverenges (CH); Christian Schmidt, Epalinges (CH)

(73) Assignee: Molecular Devices Corporation, Sunnyvale, CA (US)

( * ) Notice: Subject to any disclaimer, the term of this patent is extended or adjusted under 35 U.S.C. 154(b) by 400 days.

This patent is subject to a terminal disclaimer.

(21) Appl. No.: 10/334,815

(22) Filed: Dec. 31, 2002

(65) Prior Publication Data

US 2003/0146091 A1 Aug. 7, 2003

Related U.S. Application Data

(63) Continuation-in-part of application No. 10/229,863, filed on Aug. 27, 2002, now Pat. No. 7,244,349, which is a continuation-in-part of application No. 09/581,837, filed on Oct. 13, 2000, now Pat. No. 6,758,961, and a continuation-in-part of application No. 09/708,905, filed on Nov. 8, 2000, now abandoned, and a continuation-in-part of application No. 09/952,461, filed on Sep. 14, 2001, now abandoned, and a continuation-in-part of application No. 09/957,116, filed on Sep. 19, 2001, now abandoned, and a continuation-in-part of application No. 10/093,680, filed on Mar. 7, 2002, now Pat. No. 7,201,836, said application No. 09/952,461 is a continuation of application No. 09/581,837, filed on Oct. 13, 2000, now Pat. No. 6,758,961, said application No. 09/957,116 is a continuation-in-part of application No. 09/581,837, filed on Oct. 13, 2000, now Pat. No. 6,758,961, and a continuation-in-part of application No. 09/952,461, filed on Sep. 14, 2001, now abandoned, said application No. 10/093,680 is a continuation-in-part of application No. 09/957,116, filed on Sep. 19, 2001, now abandoned.

(60) Provisional application No. 60/164,128, filed on Nov. 8, 1999, provisional application No. 60/232,365, filed on Sep. 14, 2000, provisional application No. 60/233,800, filed on Sep. 19, 2000, provisional application No. 60/322,178, filed on Sep. 13, 2001.

(30) Foreign Application Priority Data

Dec. 17, 1997 (CH) .................................... 2903/97

(51) Int. Cl.
*G01N 33/487* (2006.01)

(52) U.S. Cl. .............................. 204/403.01; 435/287.1; 435/288.7

(58) Field of Classification Search ........... 204/403.01, 204/403.03, 416; 205/777.5, 778; 435/4, 435/173.4, 173.6, 287.1, 288.4, 288.7
See application file for complete search history.

(56) References Cited

U.S. PATENT DOCUMENTS

| | | | |
|---|---|---|---|
| 3,856,633 A | 12/1974 | Fletcher, III |
| 4,055,799 A | 10/1977 | Coster et al. |
| 4,062,750 A | 12/1977 | Butler |
| 4,071,315 A | 1/1978 | Chateau |
| 4,128,456 A | 12/1978 | Lee et al. |
| 4,225,410 A | 9/1980 | Pace |
| 4,231,660 A | 11/1980 | Remy et al. |
| 4,441,507 A | 4/1984 | Steffin |
| 4,456,522 A | 6/1984 | Blackburn |
| 4,490,216 A | 12/1984 | McConnell |
| 4,510,442 A | 4/1985 | Neher |
| 4,661,321 A | 4/1987 | Byrd et al. |
| 4,661,451 A | 4/1987 | Hansen |
| 4,803,154 A | 2/1989 | Uo et al. |
| 4,894,343 A | 1/1990 | Tanaka et al. |
| 4,911,806 A | 3/1990 | Hofmann |
| 4,912,060 A | 3/1990 | Fein |
| 4,952,518 A | 8/1990 | Johnson et al. |
| 5,009,846 A | 4/1991 | Gavet et al. |
| 5,041,266 A | 8/1991 | Fox |
| 5,055,263 A | 10/1991 | Meltzer |
| 5,111,221 A | 5/1992 | Fare et al. |

| | | | | | | |
|---|---|---|---|---|---|---|
| 5,164,319 | A | 11/1992 | Hafeman et al. | 6,461,860 B2 | 10/2002 | Mathes et al. |
| 5,169,600 | A | 12/1992 | Ishizaka et al. | 6,470,226 B1 | 10/2002 | Olesen et al. |
| 5,187,096 | A | 2/1993 | Giaever et al. | 6,475,760 B1 | 11/2002 | Baumann et al. |
| 5,204,239 | A | 4/1993 | Gitler et al. | 6,475,808 B1 | 11/2002 | Wagner et al. |
| 5,215,926 | A * | 6/1993 | Etchells et al. ............. 436/501 | 6,488,829 B1 | 12/2002 | Schroeder et al. |
| 5,225,374 | A | 7/1993 | Fare et al. | 6,596,143 B1 | 7/2003 | Wang et al. |
| 5,229,074 | A * | 7/1993 | Heath et al. .................. 422/64 | 6,602,714 B1 | 8/2003 | Tagge et al. |
| 5,229,163 | A | 7/1993 | Fox | 6,613,285 B1 | 9/2003 | Carnahan |
| 5,234,566 | A | 8/1993 | Osman et al. | 6,630,835 B1 | 10/2003 | Cheng et al. |
| 5,262,128 | A | 11/1993 | Leighton et al. | 6,635,470 B1 | 10/2003 | Vann |
| 5,310,469 | A | 5/1994 | Cunningham et al. | 6,638,743 B2 | 10/2003 | Baumann et al. |
| 5,378,342 | A | 1/1995 | Ikematsu et al. | 6,649,357 B2 | 11/2003 | Bryan et al. |
| 5,393,401 | A | 2/1995 | Knoll | 6,668,230 B2 | 12/2003 | Mansky et al. |
| 5,443,955 | A | 8/1995 | Cornell et al. | 6,670,115 B1 | 12/2003 | Zhang |
| 5,506,141 | A | 4/1996 | Weinreb et al. | 6,682,649 B1 | 1/2004 | Petersen et al. |
| 5,508,200 | A | 4/1996 | Tiffany et al. | 6,699,697 B2 | 3/2004 | Klemic et al. |
| 5,510,628 | A | 4/1996 | Georger, Jr. et al. | 6,762,036 B2 | 7/2004 | Farb et al. |
| 5,512,489 | A | 4/1996 | Girault et al. | 2001/0005489 A1 | 6/2001 | Roach et al. |
| 5,532,128 | A | 7/1996 | Eggers et al. | 2001/0005774 A1 | 6/2001 | Kato et al. |
| 5,563,067 | A | 10/1996 | Sugihara et al. | 2001/0045359 A1 | 11/2001 | Cheng et al. |
| 5,605,662 | A | 2/1997 | Heller et al. | 2002/0072103 A1 | 6/2002 | Matsumoto et al. |
| 5,632,957 | A | 5/1997 | Heller et al. | 2002/0074227 A1 | 6/2002 | Nisch et al. |
| 5,750,015 | A | 5/1998 | Soane et al. | 2002/0076825 A1 | 6/2002 | Cheng et al. |
| 5,780,752 | A | 7/1998 | Okubo et al. | 2002/0104757 A1 | 8/2002 | Schmidt |
| 5,810,725 | A | 9/1998 | Sugihara et al. | 2002/0108869 A1 | 8/2002 | Savtchenko |
| 5,858,804 | A | 1/1999 | Zanzucchi et al. | 2002/0119579 A1 | 8/2002 | Wagner |
| 5,889,216 | A | 3/1999 | Okubo et al. | 2002/0137121 A1 | 9/2002 | Rubinsky et al. |
| 5,904,824 | A | 5/1999 | Oh | 2002/0144905 A1 | 10/2002 | Schmidt |
| 5,911,871 | A | 6/1999 | Preiss et al. | 2002/0155586 A1 | 10/2002 | Cheng et al. |
| 5,955,352 | A | 9/1999 | Inoue et al. | 2002/0164777 A1 | 11/2002 | Kelly et al. |
| 5,958,345 | A | 9/1999 | Turner et al. | 2002/0182627 A1 | 12/2002 | Wang et al. |
| 5,962,081 | A | 10/1999 | Öhman et al. | 2002/0190732 A1 | 12/2002 | Cheng et al. |
| 5,981,268 | A | 11/1999 | Kovacs et al. | 2002/0195337 A1 | 12/2002 | Osipchuk et al. |
| 6,008,010 | A | 12/1999 | Greenberger et al. | 2003/0022268 A1 | 1/2003 | Lepple-Wienhues |
| 6,015,714 | A | 1/2000 | Baldarelli et al. | 2003/0052002 A1 | 3/2003 | Vogel et al. |
| 6,027,695 | A | 2/2000 | Oldenburg et al. | 2003/0059936 A1 | 3/2003 | Baumann et al. |
| 6,032,062 | A | 2/2000 | Nisch | 2003/0070923 A1 | 4/2003 | Schroeder et al. |
| 6,033,916 | A | 3/2000 | Sieben et al. | 2003/0080314 A1 | 5/2003 | Nisch et al. |
| 6,043,037 | A | 3/2000 | Lucas | 2003/0098248 A1 | 5/2003 | Vogel et al. |
| 6,048,722 | A | 4/2000 | Farb et al. | 2003/0104512 A1 | 6/2003 | Freeman et al. |
| 6,056,861 | A | 5/2000 | Fuhr et al. | 2003/0121778 A1 | 7/2003 | Dodgson et al. |
| 6,063,260 | A | 5/2000 | Olesen et al. | 2003/0129581 A1 | 7/2003 | Owen et al. |
| 6,068,818 | A | 5/2000 | Ackley et al. | 2003/0132109 A1 | 7/2003 | Bullen et al. |
| 6,093,296 | A | 7/2000 | Soane et al. | 2003/0134416 A1 | 7/2003 | Yamanishi et al. |
| 6,099,803 | A | 8/2000 | Ackley et al. | 2003/0138767 A1 | 7/2003 | Bullen et al. |
| 6,103,479 | A | 8/2000 | Taylor | 2003/0139336 A1 | 7/2003 | Norwood et al. |
| 6,106,784 | A | 8/2000 | Lund et al. | 2003/0146091 A1 | 8/2003 | Vogel et al. |
| 6,113,768 | A | 9/2000 | Fuhr et al. | 2003/0153067 A1 | 8/2003 | Stett et al. |
| 6,117,291 | A | 9/2000 | Olesen et al. | 2003/0219884 A1 | 11/2003 | Lison et al. |
| 6,132,582 | A | 10/2000 | King et al. | 2004/0062685 A1 | 4/2004 | Norton et al. |
| 6,143,496 | A | 11/2000 | Brown et al. | 2004/0251145 A1 | 12/2004 | Robertson |
| 6,151,519 | A | 11/2000 | Sugihara et al. | | | |
| 6,156,181 | A | 12/2000 | Parce et al. | | | |
| 6,163,719 | A | 12/2000 | Sherman | | | |

FOREIGN PATENT DOCUMENTS

| | | |
|---|---|---|
| 6,177,000 B1 | 1/2001 | Peterson |
| 6,207,031 B1 | 3/2001 | Adourian et al. |

| | | |
|---|---|---|
| AU | 75770/91 | 2/1995 |
| DE | 4115414 | 11/1992 |
| DE | 19605830 | 2/1997 |
| DE | 19628928 | 1/1998 |
| DE | 19646505 | 5/1998 |
| DE | 19712309 | 5/1998 |
| DE | 19815882 | 10/1999 |
| DE | 19827957 | 12/1999 |
| DE | 19936302 | 2/2001 |
| DE | 19948473 | 4/2001 |
| DE | 19961951 | 6/2001 |
| DE | 10008373 | 9/2001 |
| DE | 10022772 | 11/2001 |
| DE | 10047390 | 4/2002 |
| DE | 10061347 | 6/2002 |
| DE | 20220299 U1 | 5/2003 |
| DE | 10218325 | 11/2003 |
| DE | 10254158 | 6/2004 |
| DE | 10320899 | 12/2004 |

| | | |
|---|---|---|
| 6,225,059 B1 | 5/2001 | Ackley et al. |
| 6,228,326 B1 | 5/2001 | Boxer et al. |
| 6,235,520 B1 | 5/2001 | Malin et al. |
| 6,267,872 B1 | 7/2001 | Akeson et al. |
| 6,277,629 B1 | 8/2001 | Wolf et al. |
| 6,284,113 B1 | 9/2001 | Bjornson et al. |
| 6,287,517 B1 | 9/2001 | Ackley et al. |
| 6,315,940 B1 | 11/2001 | Nisch et al. |
| 6,329,209 B1 | 12/2001 | Wagner et al. |
| 6,355,491 B1 | 3/2002 | Zhou et al. |
| 6,365,129 B1 | 4/2002 | Fogarty |
| 6,368,851 B1 | 4/2002 | Baumann et al. |
| 6,376,233 B1 | 4/2002 | Wolf et al. |
| 6,377,057 B1 | 4/2002 | Borkholder |
| 6,379,916 B1 | 4/2002 | Meyer |
| 6,403,367 B1 | 6/2002 | Cheng et al. |
| 6,448,794 B1 | 9/2002 | Cheng et al. |

| | | |
|---|---|---|
| EP | 0094193 | 5/1983 |
| EP | 0299778 | 1/1989 |
| EP | 0299779 | 1/1989 |
| EP | 0162907 | 1/1992 |
| EP | 0639768 | 2/1995 |
| EP | 0962524 | 9/1999 |
| EP | 0960933 | 12/1999 |
| EP | 1035918 | 9/2000 |
| EP | 1040349 | 10/2000 |
| EP | 1178315 | 2/2002 |
| EP | 1203823 | 5/2002 |
| EP | 0689051 | 11/2002 |
| EP | 1333279 | 8/2003 |
| EP | 1418427 | 5/2004 |
| FR | 2659347 | 9/1991 |
| GB | 2360162 | 5/2001 |
| GB | 2355354 | 4/2002 |
| GB | 2 371 626 | 7/2002 |
| GB | 2401689 | 11/2004 |
| JP | 4-204211 | 7/1992 |
| JP | 4-204244 | 7/1992 |
| JP | 4-338240 | 11/1992 |
| JP | 2003-307481 | 10/2003 |
| JP | 2004301529 | 10/2004 |
| WO | WO 85/02201 | 5/1985 |
| WO | WO 89/01159 | 2/1989 |
| WO | WO 91/13977 | 9/1991 |
| WO | WO 92/21020 | 11/1992 |
| WO | WO 94/15701 | 7/1994 |
| WO | WO 94/25862 | 11/1994 |
| WO | WO 96/13721 | 5/1996 |
| WO | WO 97/17426 | 5/1997 |
| WO | WO 97/22875 | 6/1997 |
| WO | WO 97/25616 | 7/1997 |
| WO | WO 97/40104 | 10/1997 |
| WO | WO 97/46882 | 12/1997 |
| WO | WO 97/49987 | 12/1997 |
| WO | WO 98/01150 | 1/1998 |
| WO | WO 98/22819 | 5/1998 |
| WO | WO 98/47003 | 10/1998 |
| WO | WO 98/54294 | 12/1998 |
| WO | WO 98/58248 | 12/1998 |
| WO | WO 99/19729 | 4/1999 |
| WO | WO 99/28037 | 6/1999 |
| WO | WO 99/31503 | 6/1999 |
| WO | WO 99/34202 | 7/1999 |
| WO | WO 99/39829 | 8/1999 |
| WO | WO 99/66329 | 12/1999 |
| WO | WO 00/25121 | 5/2000 |
| WO | WO 00/34776 | 6/2000 |
| WO | WO 00/71742 | 11/2000 |
| WO | WO 01/07583 | 2/2001 |
| WO | WO 01/07584 | 2/2001 |
| WO | WO 01/07585 | 2/2001 |
| WO | WO 01/25769 | 4/2001 |
| WO | WO 01/27614 | 4/2001 |
| WO | WO 01/34764 | 5/2001 |
| WO | WO 01/48474 | 7/2001 |
| WO | WO 01/48475 | 7/2001 |
| WO | WO 01/59153 | 8/2001 |
| WO | WO 01/59447 | 8/2001 |
| WO | WO 01/69241 | 9/2001 |
| WO | WO 01/71349 | 9/2001 |
| WO | WO 01/75438 | 10/2001 |
| WO | WO 01/81425 | 11/2001 |
| WO | WO 01/86290 | 11/2001 |
| WO | WO 01/94939 | 12/2001 |
| WO | WO 02/00217 | 1/2002 |
| WO | WO 02/02608 | 1/2002 |
| WO | WO 02/03058 | 1/2002 |
| WO | WO 02/04656 | 1/2002 |
| WO | WO 02/08748 | 1/2002 |
| WO | WO 02/10747 | 2/2002 |
| WO | WO 02/12896 | 2/2002 |
| WO | WO 02/16936 | 2/2002 |
| WO | WO 02/27909 | 4/2002 |
| WO | WO 02/28523 | 4/2002 |
| WO | WO 02/29402 | 4/2002 |
| WO | WO 02/31505 | 4/2002 |
| WO | WO 02/052045 | 7/2002 |
| WO | WO 02/059597 | 8/2002 |
| WO | WO 02/059598 | 8/2002 |
| WO | WO 02/059603 | 8/2002 |
| WO | WO 02/065092 | 8/2002 |
| WO | WO 02/066596 | 8/2002 |
| WO | WO 02/073159 | 9/2002 |
| WO | WO 02/074983 | 9/2002 |
| WO | WO 02/077259 | 10/2002 |
| WO | WO 02/077627 | 10/2002 |
| WO | WO 02/082046 | 10/2002 |
| WO | WO 02/095357 | 11/2002 |
| WO | WO 02/103354 | 12/2002 |
| WO | WO 03/046216 | 6/2003 |
| WO | WO 03/047738 | 6/2003 |
| WO | WO 03/067251 | 8/2003 |
| WO | WO 03/089564 | 10/2003 |
| WO | WO 03/093494 | 11/2003 |
| WO | WO 2004/011084 | 2/2004 |
| WO | WO 2004/018690 | 3/2004 |
| WO | WO 2004/021002 | 3/2004 |
| WO | WO 2004/034052 | 4/2004 |
| WO | WO 2004/038410 | 5/2004 |
| WO | WO 2004/044574 | 5/2004 |
| WO | WO 2004/074829 | 9/2004 |
| WO | WO 2004/100229 | 11/2004 |
| WO | WO 2005/007866 | 1/2005 |
| WO | WO 2005/012554 | 2/2005 |

OTHER PUBLICATIONS

Wang et al, Neuron, vol. 15, Oct. 1995, pp. 755-760.*
*Haptotaxis and the Mechanism of Cell Mobility*, Carter, Nature, pp. 256-261, Jan. 21, 1967.
*Effect of Internal Fluoride and Phosphate on Membrane Currents During Intracellular Dialysis of Nerve Cells*, Kostyuk et al., Nature, vol. 257, pp. 691-693, Oct. 23, 1975.
*Adhesion of Cells to Surfaces Coated with Polylysine*, Mazia et al., Journal of Cell Biology, vol. 66, pp. 198-200, 1975.
*The Feynman Lectures on Physics*, Feynman et al., pp. 10-1 through 10-5, ᶜ Feb. 1977.
*Role of Electrogenic Sodnam Pump in Slow Synaptic Inhibition is Re-evaluated*, Kostyuk et al., Nature, vol. 267, May 5, 1977.
*Fusion of Phospholipid Vesicles with Planar Phospholipid Bilayer Membranes*, Cohen et al., J. Gen. Physiol., vol. 75, pp. 251-270, Mar. 1980.
*Improved Patch-Clamp Techniques for High-Resolution Current Recording From Cells and Cell-Free Membrane Patches*, Hamill et al., Pflügers Arch., vol. 391, pp. 85-100, 1981.
*Preparation of Large Unilamellar Vesicles*, Hub et al., FEBS Letters, vol. 140, No. 2, pp. 254-256, Apr. 1982.
*Formation and Properties of Cell-Size Lipid Bilayer Vesicles*, Mueller et al., Biophysics Journal, vol. 44, pp. 375-381. Dec. 1983.
*Perfusion of Oocytes*, Yoshii et al., Intracellular Perfusion of Excitable Cells. pp. 77-89, 1984.
*Intracellular Perfusion of Excitable Cells*, Kostyuk et al., pp. 35-51, 1984.
*Novel Method of Cell Fusion in Field Constriction Area in Fluid Integrated Circuit*, Masuda et al., IEEE Trans. IAS, XP-002181725, pp. 1549-1553, Oct. 1987.
*A Membrane Fusion Strategy for Single-Channel Recordings of Membranes Usually Non-Accessible to Patch-Clamp Pipette Electrodes*, Criado et al., FEBS Letters, vol. 224, No. 1, pp. 172-176, Nov. 1987.
*Muscarinic Activation of Ionic Currents Measured by a New Whole-Cell Recording Method*, Horn et al., Journal of General Physiology, vol. 92, pp. 145-159, August 1988.

*Controlled Outgrowth of Dissociated Neurons on Patterned Substrates*, Kleinfeld et al., *The Journal of Neuroscience*, vol. 8, No. 11, pp. 4098-4120, Nov. 1988.

*Single Channel Recordings of Reconstituted Ion Channel Proteins: An Improved Technique*, Keller et al., *Pflügers Arch.*, vol. 411. pp. 94-100, 1988.

*Anti-T2 Monoclonal Antibody Immobilization on Quartz Fibers: Stability and Recognition of T2 Mycotoxin*, Williamson et al., *Analytical Letters*, vol. 22, No. 4, pp. 803-816, 1989.

*Current-Voltage Relationships of a Sodium-Sensitive Potassium Channel in the Tonoplast of Chara Corallina*, Bertl, *Journal of Membrane Biology*, vol. 109, pp. 9-19, 1989.

*Optimizing Planar Lipid Bilayer Single-Channel Recordings for High Resolution with Rapid Voltage Steps*, Wonderlin et al., *Biophysics Journal*, vol. 58, pp. 289-297, Aug. 1990.

*Patch Clamp of Cation Channels*. Lewis et al., *Current Topics in Membrane and Transport*, vol. 37, pp. 215-245, 1990.

*Reconstitution of Epithelial Ion Channels*. Bridges et al., *Current Topics in Membranes and Transport*, vol. 37, pp. 283-312, 1990.

*Low Access Resistance Perforated Patch Recordings Using Amphotericin B*, Rae et al., *Journal of Neuroscience Methods*, vol. 37, pp. 15-26, 1991.

*Receptor Screening and the Search for New Pharmaceuticals*, Hodgson, *Bio/Technology*, vol. 10, pp. 973-980, Sep. 1992.

*Functional Reconstitution of the Nicotinic Acetylcholine Receptor by CHAPS Dialysis Depends on the Concentrations of Salt, Lipid, and Protein*, Schürholz et al., *Biochemistry*, vol. 31, pp. 5067-5077, 1992.

*Patch Voltage Clamping with Low-Resistance Seals: Loose Patch Clamp*, Roberts et al., *Methods and Enzymology*, vol. 207, pp. 155-176, 1992.

*Insertion of Ion Channels into Planar Lipid Bilayers by Vesicle Fusion*, Labarea et al., *Methods of Enzymology*, vol. 207, pp. 447-463, 1992.

*Patch Clamp Techniques: An Overview*, Cahalan et al., *Methods in Enzymology*, vol. 207, pp. 3-14, 1992.

*Glass Technology for Patch Clamp Electrodes*, Rae et al., *Methods in Enzymology*, vol. 207, pp. 66-92, 1992.

*Patterning Self-Assembled Monolayers Using Microcontact Printing: A New Technology for Biosensors?*, Mrksich et al., *TB Tech*, vol. 13, pp. 228-235, Jun. 1995.

*Lipid Vesicle Adsorption Versus Formation of Planar Bilayers on Solid Surfaces*, Nollert et al., *Biophysical Journal*, vol. 69, pp. 1447-1455, Oct. 1995.

*Phenomenology and Kinetics of Lipid Bilayer Spreading on Hydrophilic Surfaces*, Rädler et al., *Langmuir*, vol. 11, No. 11, pp. 4539-4548, 1995.

*A Highly Stable and Selective Biosensor Using Modified Nicotinic Acetylcholine Receptor (nAChR)*, Eray et al.; *Biosystems*, vol. 35, pp. 183-188, 1995.

*G Proteins and Regulation of Adenylate Cyclase (Nobel Lecture)*, Gilman. *Angew. Chem. Int Ed. Engl.*, vol. 34, pp. 1406-1419, 1995.

*Signal Transduction: Evolution of an Idea (Nobel Lecture)*, Rodbell, *Angew. Chem. Int. Ed. Engl.*, vol. 34, pp. 1420-1428, 1995.

*Shape Change and Physical Properties of Gian Phospholipid Vesicles Prepared in the Presence of an AC Electric Field*, Mathiyet et al., *Biophysical Journal*, vol. 70, pp. 1112-1121, Mar. 1996.

*Ion Channels from Synaptic Vesicle Membrane Fragments Reconstituted into Lipid Bilayers*, Kelly et al., *Biophysical Journal*, vol. 70, pp. 2593-2599, Jun. 1996.

*Controlling Cell Attachment on Contoured Surfaces with Self-Assembled Monolayers of Alkanethiolates on Gold*, Mrksich et al. *Proc. Natl. Acad. Sci.* USA, vol. 93, pp. 10775-10778, Oct. 1996.

*Preparation of Giant Liposomes in Physiological Conditions and Their Characterization Under an Optical Microscope*, Akashi et al., *Biophysical Journal*, vol. 71, pp. 3242-3250, Dec. 1996.

*Preparation of Giant Myelin Vesicles and Proteoliposomes to Register Ionic Channels*, Regueiro et al., *Journal of Neurochemistry*, vol. 67, No. 5, pp. 2146-2154, 1996.

*Critical Dependence of the Solubilization of Lipid Vesicles by the Detergent CHAPS on the Lipid Composition. Functional Reconstitution of the Nicotinic Acetylcholine Receptor Into Preformed Vesicles Above the Critical Micellization Concentration*, Schürholz, *Biophysical Chemistry*, vol. 58, pp. 87-96, 1996.

*A Novel Chloride Channel in Vicia faba Guard CellVacuoles Activated by the Serine/Threonine Kinase, CDPK*, Pei et al., *EMBO Journal*, vol. 15, No. 23, pp. 6564-6574, 1996.

*Investigating Channel Activity*, Aidley et al., *Ion Channels: Molecules in Action*, pp. 33-57, 1996.

*Single Binding Versus Single Channel Recordings: A New Approach to Study Ionotropic Receptors*, Edelstein et al., *Biochemistry*, vol. 36, No. 45, pp. 13755-17650, 1997.

*Nystatin/Ergosterol Method for Reconstituting Ion Channels into Planar Lipid Bilayers*, Woodbury, *Methods in Enzymology*, vol. 294, pp. 319-350, 1999.

*Isolation of Transport Vesicles that Deliver Ion Channels to the Cell Surface*, Sattsangi et al., *Methods in Enzymology*, vol. 294, pp. 339-350 (abstract only included). 1999.

*New UC Berkeley "Bionic Chip" Features Living Biological Cell Successfully Merged With Electronic Circuitry*, University of California Berkeley, Press Release, Feb. 25, 2000.

*Researchers Make 'Bionic Chip,'* Edwards, Associated Press, Feb. 25, 2000.

*A Chip-Based Biosensor for the Functional Analysis of Single Ion Channels*, Schmidt et al., *Angew. Chem. Int. Ed 2000*, vol. 39, No. 17, pp. 3137-3140, 2000.

*Osmotically Evoked Shrinking of Guard-Cell Protoplasts Causes Vesicular Retrieval of Plasma Membrane into the Cytoplasm*, Kubitscheck et al., *Planta*, vol. 210, pp. 423-431, 2000.

*The Lipid Bilayer Concept and its Experimental Realization: From Soap Bubbles, Kitchen Sink, to Bilayer Lipid Membranes*, Tien et al., *Journal of Membrane Science*, vol. 189, pp. 83-117, 2001.

*Neuron Programming Tutorial #1*, Martin, Internet pp. 1-7, Mar. 3, 2002.

*Induction to Voltage Clamp and Current Clamp*, Purves, Internet pp. 1-2, Mar. 3, 2002.

*Microfluidics-Based lab-on-a-chip Systems*, Weigl, *IVDT*, pp. 1-6, internet reprint Apr. 11, 2002.

*Patch Clamping Directly Measures Ionic Current*, Sophion Bioscience, Internet pp. 1-2, May 1, 2002.

*Patch Clamp Technique*, Nanion Products, Internet pp. 15, May 1, 2002.

*Patch Clamp on a Chip*, Sigworth et al., *Biophysical Journal*, vol. 82, pp. 2831-2832, Jun. 2002.

*A Microfabricated Chip for the Study of Cell Electroporation*, Huang et al., pp. 1-4, undated.

McCrone "Microscopy" from Kirk-Othmer, *Encyclopedia of Chemical Technology*, pp. 651, 658-659, 1995.

*HTS Approaches to Voltage-Gated Ion Channel Drug Discovery*, Denyer et al., *Drug Discovery Today*, vol. 3, No. 7, pp. 323-332, Jul. 1998.

*Cell-Based Assays and Instrumentation for Screening Ion-Channel Targets*, Gonzalez et al., *Drug Discovery Today*, vol. 4, No. 9, pp. 431-439, Sep. 1999.

*Microstructured Glass Chip for Ion-Channel Electrophysiology*, Fertig et al., *Physical Review E*, vol. 64, No. 4, Part 1, pp. 040901-1 to 040901-4, Sep. 2001.

*Ion-Channel Assay Technologies: Quo Vadis?*, Xu et al., *Drug Discovery Today*, vol. 6, No. 24, pp. 1278-1287, Dec. 2001.

*Whole Cell Patch Clamp Recording Performed on a Planar Glass Chip*, Fertig et al., *Biophysical Journal*, vol. 82, pp. 3056-3062, Jun. 2002.

*Micromolded PDMS Planar Electrode Allows Patch Clamp Electrical Recordings From Cells*, Klemic et al., *Biosensors and Bioelectonics*, vol. 17, pp. 597-604, Jun. 2002.

*An Interview with Kirk S. Schroeder, President, Essen Instruments*, *Assay and Drug Development Technologies*, vol. 1, No. 1-1, pp. 3-8, 2002.

*IonWorks™ HT: A New High-Throughput Electrophysiology Measurement Platform*, Schroeder et al., *Journal of Biomolecular Screening*, vol. 8, No. 1, pp. 50-64, Feb. 2003.

*Characterization of a Micromachined Planar Patch Clamp for Cellular Electrophysiology*, Matthews et al., *1st International IEEE EMBS Neural Engineering Conference*, pp. 1-4, Mar. 20-24, 2003.

*Automated Electrophysiology: High Throughput of Art*, Wang et al., *Assay and Drug Development Technologies*, vol. 1, No. 5, pp. 695-708 (reprint pp. 1-13), Oct. 2003.

*High Throughput Ion-Channel Pharmacology: Planar-Array-Based Voltage Clamp*, Kiss et al., *Assay and Drug Development Technologies*, vol. 1, No. 1, Part 2, pp. 127-135, Feb. 2003.

*Patchers v. Screeners: Divergent Opinion on High Throughput Electro-physiology*, Comley, *Drug Discover World*, pp. 47-57, Fall 2003.

*High Throughput Electrophysiology: New Perspectives for Ion Channel Drug Discovery*, Willumsen, *Receptors and Channels*, vol. 9, No. 1, pp. 3-12, 2003.

*High Throughput Electrophysiology Using a Fully Automated, Multiplexed Recording System*, Trumbull et al., *Receptors and Channels*, vol. 9, No. 1, pp. 19-28, 2003.

*Microstructured Apertures in Planar Glass Substrates for Ion Channel Research*, Fertig et al., *Receptors and Channels*, vol. 9, No. 1, pp. 29-40, 2003.

*Upscaling and Automation of Elecrophysiology: Toward High Throughput Screening in Ion Channel Drug Discovery*, Asmild et al., *Receptors and Channels*, vol. 9, No. 1, pp. 49-58, 2003.

*Cytocentering: A Novel Technique Enabling Automated Cell-by-Cell Patch Clamping with the Cytopatch™ Chip*, Stett et al., *Receptors and Channels*, vol. 9, No. 1, pp. 59-66, 2003.

*Screening Technologies for Ion Channel Targets in Drug Discovery*, Zheng et al., *American Pharmaceutical Review*, pp. 85-92, 2003.

*Intracellular Perfusion of Helix Giant Neurons*, Kryshtal et al., *Neirofiziologiya*, vol. 7, No. 3, pp. 327-329 (reprinted in English as pp. 258-259), May-Jun. 1975.

*Current Fluctuations, Associated with the Activation of Calcium Channel Mechanism in the Membrane of Nerve Cells*, Kristhal et al., *USSR Academy of Science Report*, vol. 231, No. 5, 1976.

*Asymmetrical Displacement Currents in Nerve Cell Membrane and Effect of Internal Fluoride*, Kostyuk et al., *Nature*, vol. 267, pp. 70-72, May 5, 1977.

*Separation of Sodium and Calcium Currents in the Somatic Membrane of Mollusc Neurones*, Kostyuk et al., *J. Physiol.*, vol. 270, pp. 545-568, 1977.

*Properties of Internally Perfused, Voltage-Clamped, Isolated Nerve Cell Bodies*, Lee et al., *Journal of General Physiology*, vol. 71, pp. 489-507, 1978.

*Ionic Currents in the Neuroblastoma Cell Membrane*, Kostyuk et al., *Neuroscience*, vol. 3, pp. 327-332, 1978.

*The Extracellular Patch Clamp: A Method for Resolving Currents Through Individual Open Channels in Biological Membranes*, Neher et al., *Pflugers Arch.*, vol. 375, pp. 219-228, 1978.

*Effects of Internal Free Calcium Upon the Sodium and Calcium Channels in the Tunicate Egg Analysed by the Internal Perfusion Technique*, Takahashi et al., vol. 279, pp. 519-549, 1978.

*Single Acetylcholine-Activated Channels Show Burst-Kinetics in Prescence of Desensitizing Concentrations of Agonist*, Sakmann et al., *Nature*, vol. 286, pp. 71-73, Jul. 3, 1980.

*Single Na+ Channel Currents Observed in Cultured Rat Muscle Cells*, Sigworth et al., *Nature*, vol. 287, pp. 447-449, Oct. 2, 1980.

*A Receptor for Protons in the Nerve Cell Membrane*, Krishtal et al., *Neuroscience*, vol. 5, pp. 2325-2327, 1980.

*Fluctuations in the Microsecond Time Range of the Current Through Single Acetylcholine Receptor Ion Channels*, Colquhoun et al., *Nature*, vol. 294, pp. 464-466, Dec. 3, 1981.

*Intracellular Perfusion*, Kostyuk et al., *Journal of Neuroscience Methods*, vol. 4, pp. 201-210, 1981.

*Receptor for Protons in the Membrane of Sensory Neurons*, Krishtal et al., *Brain Research*, vol. 214, pp. 150-154, 1981.

*A 'Receptor' for Protons in Small Neurons of Trigeminal Ganglia: Possible Role in Nociception*, Krishtal et al., *Neuroscience Letters*, vol. 24, pp. 243-246, 1981.

*Intracellular Perfusion*, Kostyuk, *Ann. Rev. Neurosci.*, vol. 5, pp. 102-120, 1982.

*Science and Technology of Patch-Recording Electrodes*, Corey et al., *Single-Channel Recording*, pp. 53-68, 1983.

*Perfusion of Isolated Neurons Fixed in Plastic Film*, Kostyuk et al., *Intracellular Perfusion of Excitable Cells*, pp. 35-51, 1984.

*Electrical Measurements on Perfused Cells*, Osipchuk et al., *Intracellular Perfusion of Excitable Cells*, pp. 103-129, 1984.

*The Patch Clamp is More Useful Than Anyone had Expected*, Sigworth, *Federation Proceedings*, vol. 45, No. 12, pp. 2673-2677, Nov. 1986.

*Quantitative Video Microscopy of Patch Clamped Membranes Stress, Strain, Capacitance, and Stretch Channel Activation*, Sokabe et al., *Biophysical Journal*, vol. 59, pp. 722-728, Mar. 1991.

*Perfusion of Nerve Cells and Separation of Sodium and Calcium Currents*, Kostyuk, *Cellular Neurobiology: A Practical Approach*, pp. 121-135, 1991.

*The Patch Clamp Technique*, Neher et al., *Scientific American*, vol. 266, pp. 44-51, Mar. 1992.

*A Novel Method for Glass Micropipette Polishing for Electropatch Clamp Recording Using Oxygen Plasma*, Itoh et al., *Biochemical and Biophysical Research Communications*, vol. 191, No. 2, pp. 447-452, 1993.

*Fast 3D Laser Micromachining of Silicon for Micromechanical and Microfluidic Applications*, Mullenborn et al., *The 8th International Conference on Solid-State Sensors and Actuators, and Eurosensors IX*, pp. 166-169, Jun. 25-29, 1995.

*A Practical Guide to Patch Clamping*, Penner, *Single-Channel Recording*, pp. 3-30, 1995.

*Geometric Parameters of Pipettes and Membrane Patches*, Sakmann et al., *Single-Channel Recording*, pp. 637-650, 1995.

*Glass-Funnel Technique for the Recording of Membrane Currents and Intracellular Perfusion of Xenopus Oocytes*, Shuba et al., *Pflugers Arch.—Eur. J. Physiol.*, vol. 432, pp. 562-570, 1996.

*Seal-Promoting Solutions and Pipette Perfusion for Patch Clamping Plant Cells*, Maathuis et al., *The Plant Journal*, vol. 11, No. 4, pp. 891-896, 1997.

*A 0.1-700 Hz Current Through a Voltage-Clamped Pore: Candidate Protein for Initiator of Neural Oscillations*, McGeoch et al., *Brain Research*, vol. 766, pp. 188-194, 1997.

*Fabrication of a Novel Microsystems for the Electrical Characterisation of Cell Arrays*, Hediger et al., *Sensors and Actuators*, vol. 56, pp. 175-180, 1999.

*Electroporation of Cells and Tissues*, Weaver, *IEEE Transactions on Plasma Science*, vol. 28, No. 1, pp. 24-33, Feb. 2000.

*Characterization of Single-Cell Electroporation by Using Patch-Clamp and Fluorescence Microscopy*, Ryttsen et al., *Biophysical Journal*, vol. 79, pp. 1993-2001, Oct. 2000.

*Biological-to-Electronic Interface with Pores of ATP Synthase Subunit C in Silicon Nitride Barrier*, McGeoch et al., *Medical & Biological Engineering & Computing*, vol. 28, pp. 113-119, 2000.

*Planar Patch Clamping not an Automatic Choice*, Shah, *Drug Discovery & Development*, pp. 59-63, Jul. 2004.

*Characterization, Toxicity and Therapeutic Efficacy of Adriamycin Encapsulated in Liposomes*, Olson et al., *European Journal of Cancer & Clinical Oncology*, vol. 18, No. 2, pp. 167-176, Feb. 1982 (abstract only).

*Impedance Analysis of Support Lipid Bilayer Membranes: A Scrutiny of Different Preparation Techniques*, Steinem et al., *Biochimica et. Biophysica Acta*, vol. 1279, pp. 169-180, 1996.

*Planar Lipid Bilayers on Solid Supports From Liposomes—Factors of Imporatance for Kinetics and Stability*, Puu et al., *Biochimica et, Biophysica Acta*, vol. 1327, pp. 149-161, 1997.

*Automated Patch-Clamps Enable Faster Ion Screening*, McGee, *Drug Discovery & Development*, pp. 51-53, Jan. 2005.

*Characterization of hERG Screen Using the IonWorks HT: Comparison to a hERG Rubidium Efflux Screen*, Sorota et al., *Assay and Drug Development Technologies*, vol. 3, No. 1, pp. 47-57, 2005.

*Cloe Screen™ HERG Safety Single Cell Planar Patch Clamp Method* article/information pages, Cyprotex, undated (internet print date May 4, 2005).

*Planar Lipid Bilayers on Patch Pipettes: Bilayer Formation and Ion Channels Incorporation*, Ehrlich, *Methods in Enzymology*, vol. 207, pp. 463-470, 1992.

*The Axon Guide for Electrophysiology and Biophysics Laboratory Techniques*, Axon Instruments, Inc., Jun. 1993.

*Molecular Biology of the Cell*, Third Edition, Alberts et al., pp. 178-189, ᶜ 1994.

*Modeling Success and Failure of Langmuir-Blodgett Transfer of Phospholipid Bilayers to Silicon Dioxide*, Osborn et al., *Biophysical Journal*, vol. 68, pp. 1364-1373, Apr. 1995.

\* cited by examiner

*Primary Examiner*—Kaj K. Olsen

(74) *Attorney, Agent, or Firm*—Morgan, Lewis & Bockius LLP; David J. Brezner; Victor E. Johnson

(57) ABSTRACT

Systems for positioning and/or analyzing samples such as cells, vesicles, cellular organelles, and fragments, derivatives, and mixtures thereof, for electrical and/or optical analysis, especially relating to the presence and/or activity of ion channels.

64 Claims, 13 Drawing Sheets

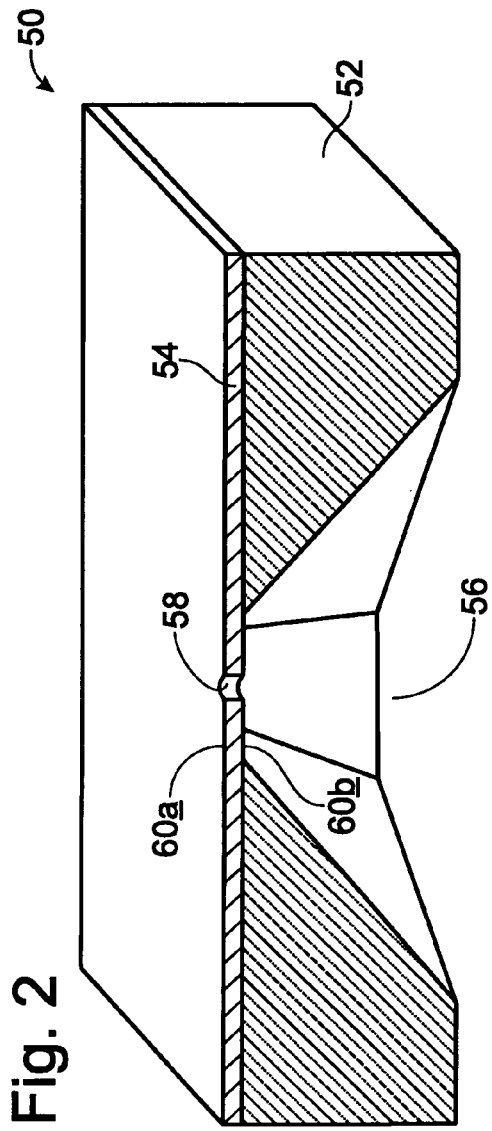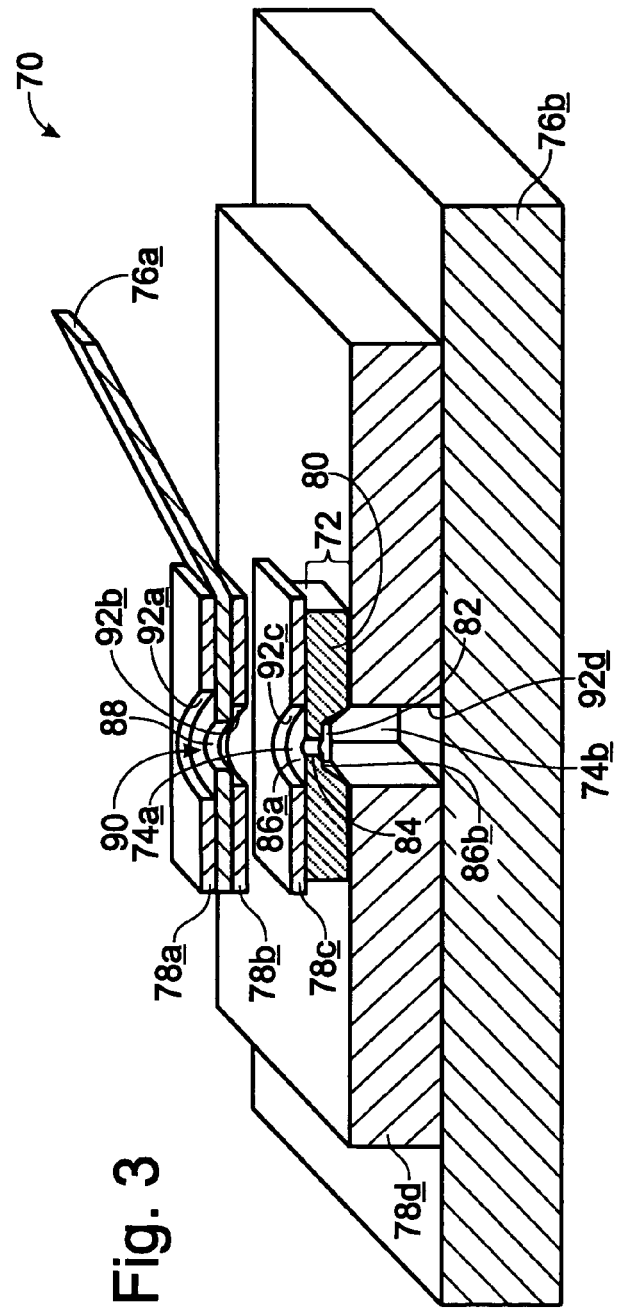

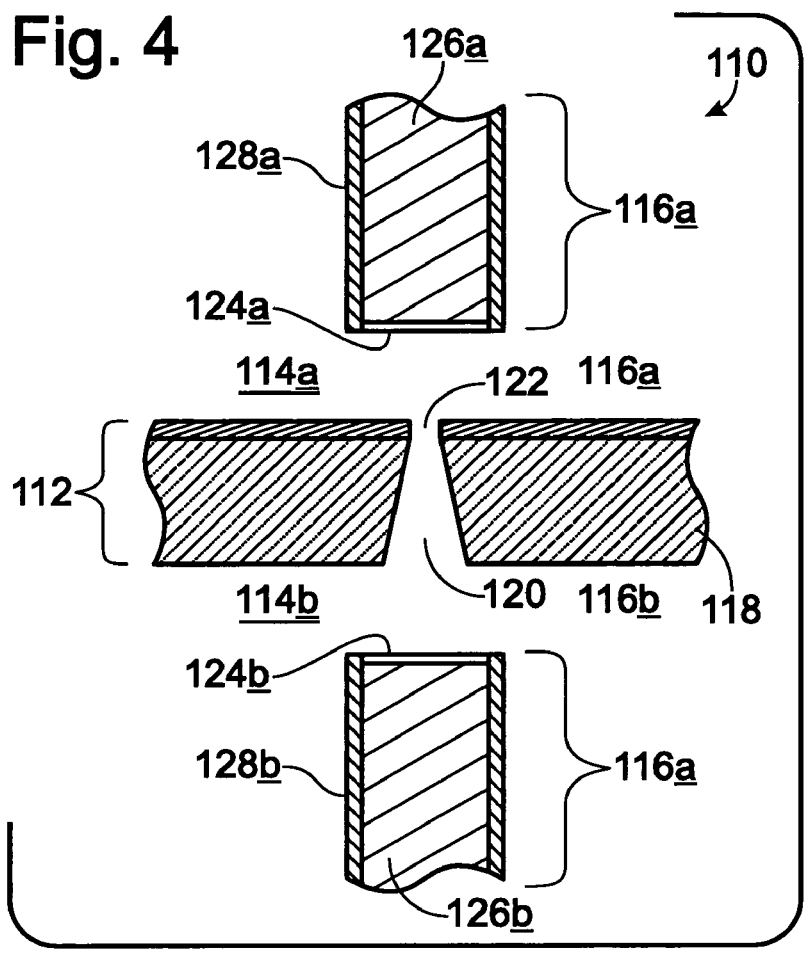
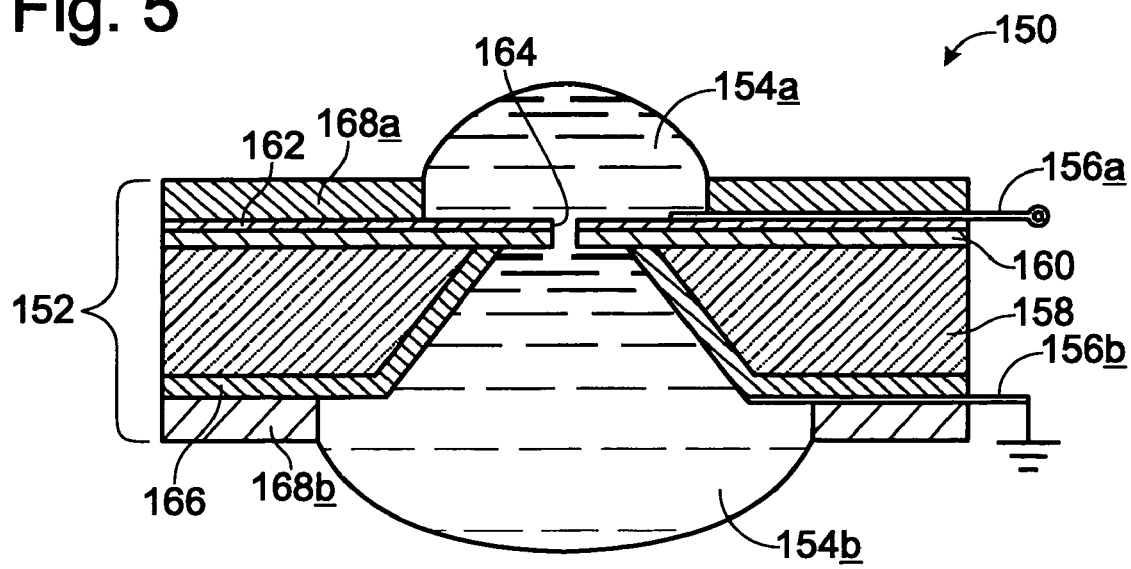

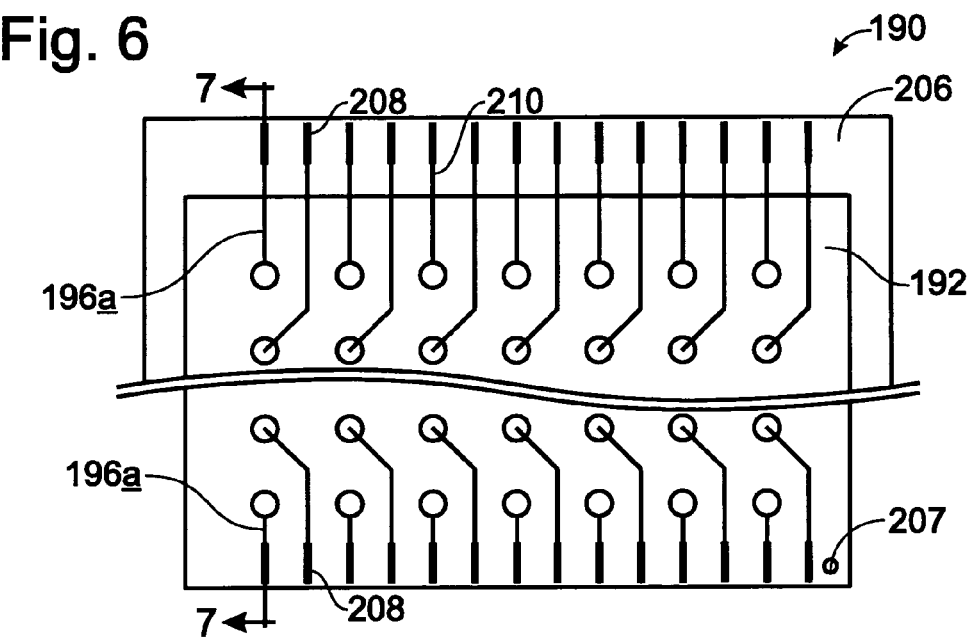
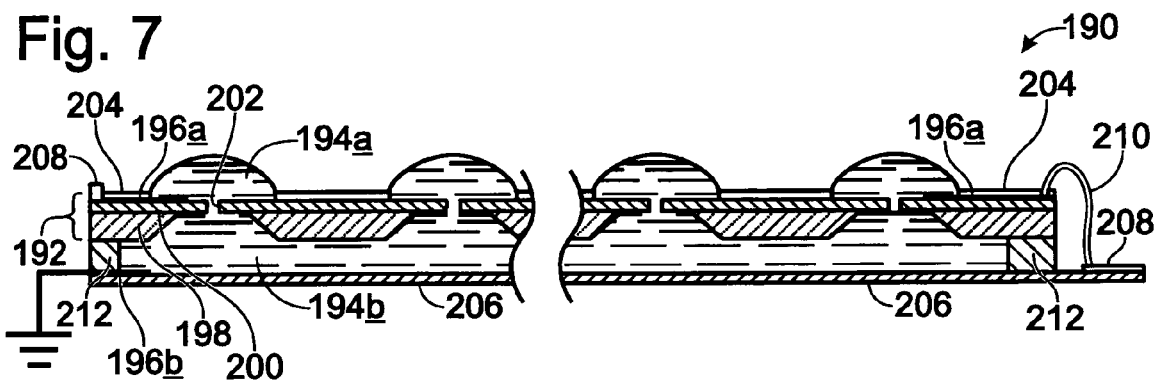
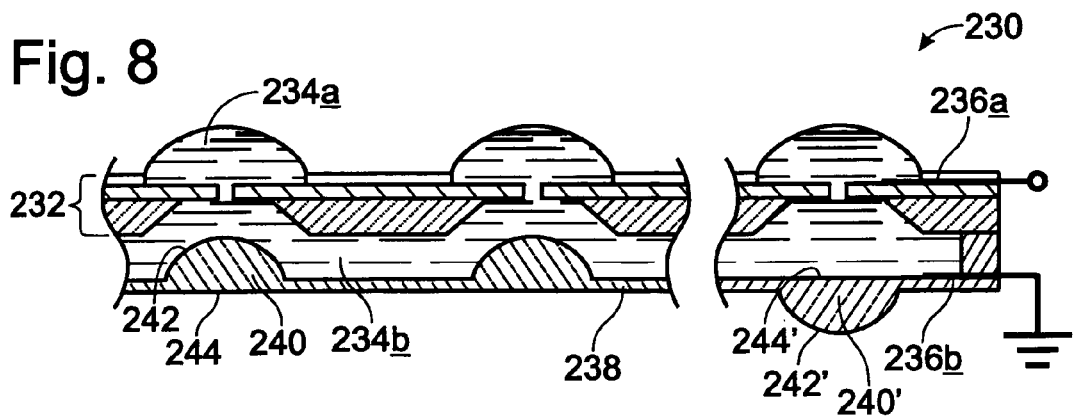

SAMPLE POSITIONING AND ANALYSIS SYSTEM

CROSS-REFERENCE TO PRIORITY APPLICATIONS

This application is a continuation-in-part of U.S. patent application Ser. No. 10/229,863, filed Aug. 27, 2002 now U.S. Pat. No 7,244,349.

U.S. patent application Ser. No. 10/229,863, in turn, is a continuation-in-part of the following U.S. patent applications: Ser. No. 09/581,837, filed Oct. 13, 2000 (now U.S. Pat. No. 6,758,961); Ser. No. 09/708,905, filed Nov. 8, 2000 (now abandoned); Ser. No. 09/952,461, filed Sep. 14, 2001 (now abandoned); Ser. No. 09/957,116, flied Sep. 19, 2001 (now abandoned); and Ser. No. 10/093,680, filed Mar. 7, 2002 now U.S. Pat. No. 7,201,836. U.S. patent application Ser. No. 10/229,863 also claims the benefit under 35 U.S.C. § 119(e) of U.S. Provisional Patent Application Ser. No. 60/322,178, filed Sep. 13, 2001.

U.S. patent application Ser. No. 09/581,837 (now U.S. Pat. No. 6,758,961), in turn, claims priority from PCT Patent Application Ser. No. PCT/IB98/01150, filed Jul. 28, 1998, which, in turn, claims priority from Swiss Patent Application Ser. No. 2903/97, flied Dec. 17, 1997.

U.S. patent application Ser. No. 09/708,905 (now abandoned), in turn, claims the benefit under 35 U.S.C. § 119(e) of U.S. Provisional Patent Application Ser. No. 60/164,128, filed Nov. 8, 1999.

U.S. patent application Ser. No. 09/952,461 (now abandoned), in turn, is a continuation of U.S. patent application Ser. No. 09/58 1,837 (now U.S. Pat. No. 6,758,961), filed Oct. 13, 2000, which claims priority from PCT and Swiss patent applications, as listed above, U.S. patent application Ser. No. 09/952,461 (now abandoned) also claims the benefit under 35 U.S.C. § 119(e) of the following U.S. provisional patent applications: Ser. No. 60/232,365, filed Sep. 14, 2000; Ser. No. 60/233,800, filed Sep. 19, 2000; and Ser. No. 60/322,178, filed Sep. 13, 2001.

U.S. patent application Ser. No. 09/957,116 (now abandoned), in turn, is a continuation-in-pan of the following U.S. patent applications: Ser. No. 09/581,837, filed Oct. 13, 2000 (now U.S. Pat. No. 6,758,961), which claims priority from PCT and Swiss patent applications, as listed above; and Ser. No. 09/952,461, filed Sep. 14, 2001 (now abandoned), which claims priority from U.S., PCT, Swiss, and provisional patent applications, as listed above. U.S. patent application Ser. No. 09/957,116 (now abandoned) also claims the benefit under 35 U.S.C. § 119(e) of the following U.S. provisional patent applications: Ser. No. 60/233,800, filed Sep. 19, 2000; and Ser. No. 60/322,178, filed Sep. 13, 2001.

U.S. patent application Ser. No. 10/093,680, in turn, is a continuation of U.S. patent application Ser. No. 09/957,116, filed Sep. 19, 2001 (now abandoned), which claims priority from U.S., PCT, Swiss, and provisional patent applications, as listed above.

The above-identified U.S., PCT, Swiss, and provisional priority patent applications are all incorporated herein by reference in their entirety for all purposes.

CROSS-REFERENCES TO ADDITIONAL PRIORITY APPLICATIONS

This application is a continuation-in-part of the following PCT patent applications, which are incorporated herein by reference in their entirety for all purposes: Ser. No. PCT/IB01/00095, filed Jan. 26, 2001; and Ser. No. PCT/IB01/00097, filed Jan. 26, 2001.

This application is based upon and claims benefit under 35 U.S.C. § 119(e) of the following U.S. provisional patent applications, which are incorporated herein by reference in their entirety for all purposes: Ser. No. 60/353,411, filed Feb. 1, 2002; Ser. No. 60/360,731, filed Mar. 1, 2002; Ser. No. 60/361,202, filed Mar. 1, 2002; Ser. No. 60/362,923, filed Mar. 7,2002; Ser. No. 60/368,514, filed Mar. 28, 2002; and Ser. No. 60/383,199, filed May 22, 2002.

This application is based upon and claims benefit under 35 U.S.C. §119(e) of U.S. Provisional Patent Application Ser. No. 60/366,113, filed Mar. 19, 2002.

FIELD OF THE INVENTION

The invention relates to systems for positioning and/or analyzing samples. More particularly, the invention relates to systems for positioning and/or analyzing samples such as cells, vesicles, cellular organelles, and fragments, derivatives, and mixtures thereof, for electrical and/or optical analysis, especially relating to the presence and/or activity of ion channels.

BACKGROUND OF THE INVENTION

Cells are the smallest structural unit of biological organisms that are capable of independent functioning, consisting of a semipermeable cell membrane enclosing cytoplasm, a nucleus, and various organelles. Cell membranes are important to the functions of a cell, with variety of important biological processes occurring at or within the membrane, including the absorption of nutrients, the secretion of metabolic products, the control of cell volume, and the communication with the outside environment.

Thus, it is not surprising that the biological function of cell membranes and especially of membrane proteins has become an area of active research. Signal transduction processes in general, including nerve conduction, and neuroreceptors in particular have been shown to be influenced by pharmacologically active ingredients, making them obvious targets for drug development.[i] Ion channels and ion transporters also have been shown to be an important class of therapeutic targets. In fact, interactions with ion channels have become a major potential source of adverse effects when administering a therapeutic agent, leading the Food and Drug Administration (FDA) and other government regulatory agencies to require safety profiling of potential therapeutics against certain ion channels.

This understanding of the interactions between potential drugs and cell membrane components is beginning to play a crucial role in modern drug development. In view of the increasing number of known receptors and the rapidly growing libraries of potential pharmaceutical ingredients, there clearly is a need for highly sensitive screening methods that permit the analysis of a large number of different substances with high assay throughput per unit time, otherwise known as "high throughput screening" (or "HTS"). In particular, there is a need for automated and/or high throughput screening methods that are relevant to cell membrane components.

At present, relatively traditional methods are used for the screening of pharmaceutical ingredients. Such methods include ligand binding assays and receptor function tests that are performed separately.[ii] Although binding assays are relatively inexpensive, and amenable to high throughput, they require labeled high-affinity ligands, and generally are limited to assays for ligands that can compete effectively for labeled ligand. Fluorescent or fluorogenic reagents generally are compatible with high throughput assays, including the analysis of ion channels using fluorescent calcium indicators, and the evaluation of membrane potential effects with potential-sensitive dyes. However, such reagents typically are not sensitive enough for single cell measurements, and generally can provide only indirect measurements of the membrane component of interest.

The patch clamp was introduced by Neher and Sakmann in the early 1980s as a powerful technique for the direct study of drug effects on single receptors. In recognition of the strength of the method, Neher and Sakmann were awarded the Nobel prize in 1991. Classical patch-clamp methods often are used in conjunction with functional membrane receptor assays, including receptors coupled to G-proteins and ion channel-forming receptors.[iii] This method is highly specific and extremely sensitive: it can, in principle, be used to measure the channel activity of individual receptor molecules. In doing so, glass micropipettes with an opening diameter of typically 1-0.1 µm are pressed on the surface of a biological cell. The membrane surface that is covered by the micropipette is called a "patch." If the contact between the glass electrode and the cell membrane surface is sufficiently electrically isolating, the ion flow over the membrane patch can be measured electrically with the aid of microelectrodes, one placed in the glass pipette and the other placed in the milieu opposite the membrane.[iv] A significant advantage of this electrophysiological method is that it makes directly accessible the function of the corresponding channel-forming proteins or receptors coupled to channel-forming proteins via the measured electrical characteristics of the channel-forming proteins.

Unfortunately, several major limitations have prevented patch-clamp technology from revolutionizing receptor science and pharmaceutical drug development. For example, to produce high quality results, the patch-clamp method requires a tremendous effort in technical installation and highly qualified operators. Moreover, in addition to being expensive, a standard patch-clamp setup may require a long set-up time and have a high failure rate.

Thus, there is a need for a system for positioning and/or analyzing cells that is rapid, facile, and suitable for multi-array analysis, such as the system provided by the invention.

SUMMARY OF THE INVENTION

The invention provides systems for positioning and/or analyzing samples such as cells, vesicles, cellular organelles, and fragments, derivatives, and mixtures thereof, for electrical and/or optical analysis, especially relating to the presence and/or activity of ion channels.

BRIEF DESCRIPTION OF THE DRAWINGS

FIG. 2 is a cross-sectional side view of a substrate chip prepared from Si/SiO$_2$ in accordance with aspects of the invention.

FIG. 3 is a cross-sectional side view of a measurement system having planar electrodes in accordance with aspects of the invention.

FIG. 4 is a cross-sectional side view of a measurement system having point or wire electrodes in accordance with aspects of the invention.

FIG. 5 is a cross-sectional side view of a measurement system having open fluid compartments in accordance with aspects of the invention.

FIG. 6 is a top view of a measurement system having multiple measurement sites in accordance with aspects of the invention.

FIG. 7 is a cross-sectional side view of the measurement system of FIG. 6, taken generally along line 7-7 in FIG. 6.

FIG. 8 is a cross-sectional side view of a measurement system having optical measurement aids in accordance with aspects of the invention.

FIG. 15A shows the membrane resistance during accidental receptor openings in the absence of ligands at 400 mM KCl and positive potentials.

DETAILED DESCRIPTION

The invention provides systems such as single and multiaperture biochips for positioning and/or analyzing membrane-bound samples, such as cells, vesicles, cellular organelles, and/or portions thereof. Positioning a sample, as used here, generally comprises locating or placing the sample at a preselected position, within the system, typically for subsequent analysis. Analyzing the sample generally comprises detecting a presence or activity within the sample, while it is positioned at the preselected position, typically relating at least in part to electrical properties of the sample.

Figure 1:
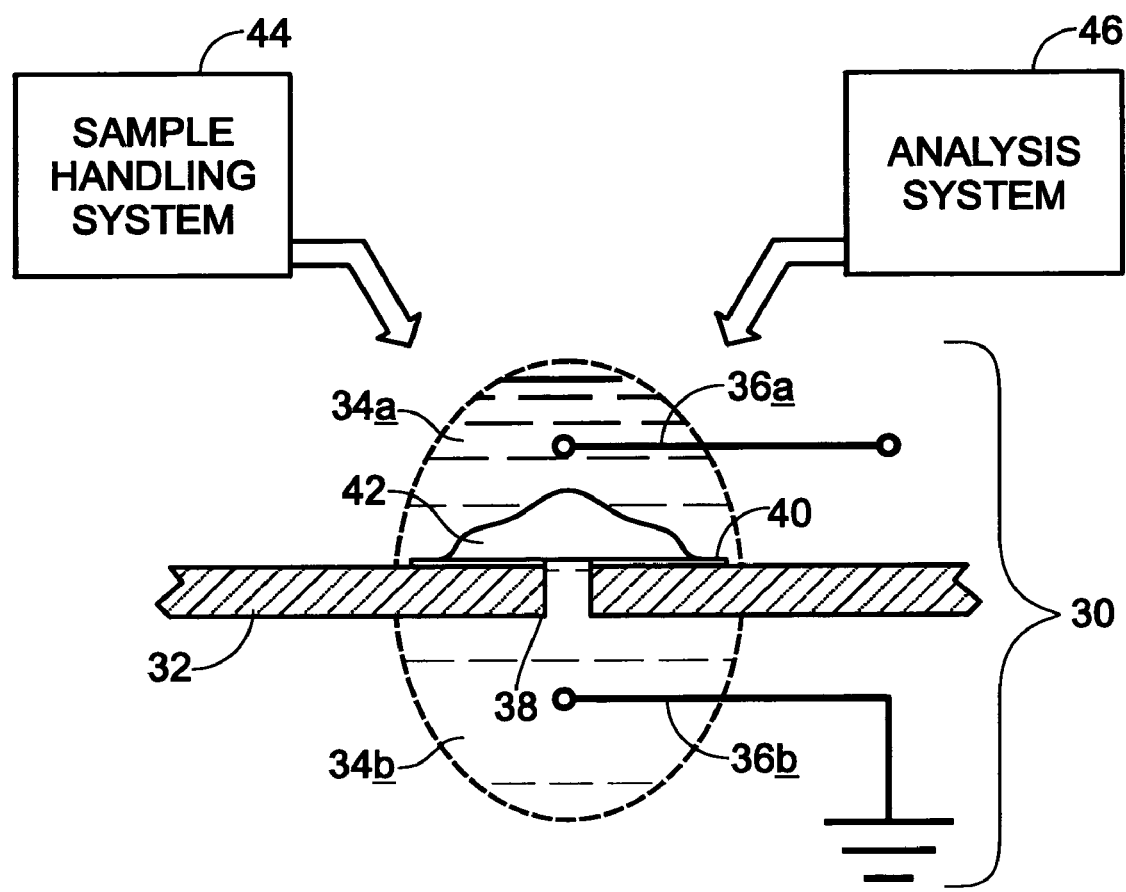
FIG. 1 is a schematic view of a system for positioning and/or analyzing samples in accordance with aspects of the invention.

FIG. 1 shows a representative system 30 for positioning and/or analyzing samples in accordance with aspects of the invention. The system includes a substrate 32, at least two fluid compartments 34a,b, and at least two electrodes 36a,b. (In some cases, for example, where only optical measurements are to be performed, the system may have only a single fluid compartment and no electrodes.) The substrate comprises a separating wall of electrically isolating material, and may include an aperture and/or window 38 and an associated adhesion surface 40 adjacent the aperture to which samples 42 may be bind or be fixed using any suitable mechanism. The fluid compartments generally comprise any region or volume adapted to support a fluid adjacent the aperture. The electrodes generally comprise any mechanism for applying and/or measuring an electric potential and associated electric field across the aperture. In most embodiments, a first side of the substrate is used as a sample or measurement side, and a second side of the substrate is used as a reference side, although these roles may be interchangeable. The measurement side is used to hold samples during positioning and/or analysis, and typically includes adhesion surface 40, a measurement fluid compartment 34a and a measurement electrode 36a. The reference side is used to complete the electric circuit, and typically includes a reference fluid compartment 34b and a reference electrode 36b. Generally, despite their different names, the measurement electrode and the reference electrode independently may be set to any suitable voltage, including ground.

The system may include or be interfaced with one or more auxiliary systems, including (1) a sample handling system 44 for introducing, removing, and/or otherwise manipulating fluids and/or samples, (2) an analysis system 46 for analyzing samples, particularly by mechanisms other than direct electrical measurement, and/or (3) an incubation system for storing samples before and/or during assays, and/or (4) a cleaning system for cleaning substrates and/or other system components.

The system may be used for a variety of applications. These applications may include automated and/or high-throughput patch-clamp analysis (e.g., for drug screening), portable biosensor analysis (e.g., for environmental analytes), and so on. These applications also may include the separation of cells or vesicles, the analysis of the sizes of cells or vesicles, the direct functional analysis of ionotropic membrane proteins, for example, in ligand binding studies, and/or the positioning of cells or vesicles for any suitable purpose, including purely optical investigations and/or microinjections, among others. Typically, a sample such as a cell or vesicle is introduced into the measurement compartment and then is directed toward the aperture, for example, using an electric force created by the two electrodes. The sample contacts the adhesion surface, binds across the aperture, and forms an electrical seal with the aperture sufficient for performing an assay of interest. The effects of an applied voltage created by the electrodes then may be studied, typically before and/or after exposure to a suitable assay condition. The studies may be performed by measuring changes in electrical properties across the aperture, such as current, resistance, or the like, and/or by measuring other changes in the sample, such as ion levels or the like.

The assay condition generally comprises any change of condition, optionally including a change in environmental condition, such as sample temperature, but more typically including the addition of one or more reagents such as candidate drug compounds to the sample. The reagent may be a chemical reagent, such as an acid, a base, a metal ion, an organic solvent, or other substance intended to effect a chemical change in the sample. Alternatively, the reagent may have or be suspected to have a biological activity or type of interaction with a given biomolecule. Selected assay components may include membrane-active substances, such as pore promoters, proteoliposomes, and/or membrane proteins. Selected assay reagents also may include oligonucleotides, nucleic acid polymers, peptides, proteins, drugs, and other biologically active molecules.

The system may have one or more advantages over prior systems for measuring electrical properties of cells and vesicles. First, the system is relatively simple, both in the production of electrically insulating patch membranes and in the associated measurements. Thus, the system, alone or in combination with modern microtechnological methods, is suitable for use in automated and/or "high throughput screening" (HTS) applications. Second, the positioning and measuring capabilities of the system are well suited to the combination of electrical and optical measurements, through which, on these planar membranes, obtained by means of the positioning process according to the invention, new, important information concerning membrane channels and receptors may be obtained.

The following sections describe various components and functionalities of the system, including (A) the substrate, (B) the apertures and windows, (C) the adhesion surfaces, including mechanisms for achieving binding, (D) the fluid compartments, (E) the electrodes, (F) multiaperture systems, (G) the analysis system, (H) the sample handling system, (I) the samples, (J) the, sample positioning process, and (K) the measurement process, among others.

A. Substrates

The substrate generally comprises any surface or set of surfaces capable of separating two fluid compartments. The substrate typically includes an aperture that passes through the substrate to connect the two fluid compartments and at least one adhesion surface adjacent the aperture for binding a sample such as a cell or vesicle for analysis. The substrate preferably is nonconductive (e.g., electrically insulating), thus reducing or eliminating electrical contact between the two fluid compartments, except through the aperture.

The substrate may be formed of any suitable material. Preferably, the substrate is nonconductive, inert (in the system), and no more than slightly modifiable chemically. Exemplary materials include silicon (including silicon (Si) and silicon derivatives, such as silicon oxide ($SO_2$; silica) and silicon oxinitride ($SiO_xN_y$)), glass, quartz, plastic, and so on. Among these, the silicon-based substrates have several advantages. First, they are commercially available. Second, they are easily processed, for example, so that they may be provided with an aperture and/or window, as described below in Example 1. Third, they readily may be coated or otherwise partially or completely covered with insulating and/or adhesion-promoting materials. Such surface layers include layers of quartz, glass, and solid and/or gelatinous polymers, among others. Such surface layers also include plastomers and elastomers, such as polyimides, polymethylmethacrylates, polycarbonates, and silica gels (e.g. Sylgard). Such surface layers also may be homogeneous or inhomogeneous, where, for example, in the latter case, they may be applied as droplets.

The substrate may include two or more pieces or components, for example, being constructed of a holder on which the material actually relevant to membrane positioning and membrane binding is fastened or into which this material is admitted, where this material for the positioning, or alternatively the binding, of the membranes has at least one aperture.

The substrate may be formed with any suitable geometry, subject to the above limitations. However, preferably, the substrate is at least substantially planar, and more preferably, the substrate is microscopically flat and molecularly relatively planar, particularly at the adhesion surface.

Examples 1-7 below, among others, describe exemplary substrates, including materials, geometries, and relationships with other components of the system.

B. Apertures and Windows

The aperture and window(s) are the portions of the substrate most immediately involved in the positioning and/or analysis of samples.

The aperture generally comprises any opening or other passage through the substrate. This opening may include a hole, a gap, and/or a slit, among others, and may allow fluid contact between fluid compartments positioned at opposite sides of the aperture. The aperture may be capable of forming an electrical seal with a sample such as a cell or vesicle that is sufficiently "tight" to use in a patch clamp experiment. Exemplary seals (depending on sample type and condition) have included >10 kΩ, >100 kΩ, >1 MΩ, >10 MΩ, >100 MΩ, >1 GΩ, >10 GΩ, >100 GΩ, and even >1 TΩ. Alternatively, or in addition, the aperture may be capable of focusing an electric field with sufficient strength to position a sample such as a cell or vesicle about the aperture. The aperture may include a hole, a gap, and/or a slit, among others.

The aperture is characterized by a length $L_{ap}$ and a diameter $d_{aperture}$. The length is determined by the thickness of the substrate adjacent the aperture, generally ranging between about 3 nm and about 1000 μm, and preferably ranging between about 100 nm and about 20 μm. The diameter of the aperture, as measured immediately adjacent the binding surface, is influenced by a variety of different factors, which may urge toward either smaller or larger apertures. First, smaller apertures generally increase the quality of the electrical seal between the aperture and the sample, up to a limit. In particular, to form a tight electrical seal, the aperture should be smaller, preferably significantly smaller, than the size of the sample (i.e., $d_{aperture} \ll d_{cell}$, $d_{vesicle}$), but larger, preferably significantly larger, than the lipids and other molecules present in the sample. Second, smaller apertures generally increase the mechanical stability of the membrane across the aperture. In particular, the force required to deflect a portion of membrane is inversely proportional to the square of the radius of the portion being deflected (i.e., proportional to the value of $r_M^{-2}$; see, e.g., Example 12), so that the selection of small (e.g., $d_{aperture} < 5$ μm) apertures may significantly increase membrane stability, particularly relative to the typical (e.g., $d_{aperture} > 100$ μm) apertures used in conventional black lipid membrane (BLM) systems. Third, smaller apertures generally increase the strength and focus of the electric field passing through the aperture, which is especially useful when positioning samples. Fourth, larger apertures generally reduce the access resistance, improving the quality of the voltage (or current) clamp, probably by easing the physical access of the conduction ions. Based on these factors, the diameter of the aperture generally is less than about 15 to 20 μm, usually is less than about 10 μm, preferably is less than about 7 μm, and more preferably is less than about 5 μm. In particular, sizes between about 0.3 μm and about 7 μm may yield an outstanding probability and quality of sealing. Stated alternatively, the aperture preferably should have a diameter of no more than a few tens of percent, and more preferably no more than about 30 percent, of the sample diameter. Thus, for cellular samples, which typically have a diameter of greater than about 20 μm, the aperture preferably should have a diameter of no more than about 5-7 μm.

The window generally comprises a portion of the fluid compartment adjacent and providing access to the aperture. The preferred size of the window is determined by factors analogous to those described above for determining the preferred size of the aperture. In brief, the diameter of the window preferably is less than about 1000 μm, and more preferably is significantly smaller, being not more than about 100 μm.

Examples 1-7 below, among others, describe exemplary apertures and windows, including geometries and relationships with other components of the system.

C. Binding and Adhesion Surfaces

The adhesion surface generally comprises any surface or set of surfaces adjacent the aperture to which samples such as cells and vesicles may bind for analysis. The adhesion surface typically is at least substantially planar over an area exceeding that of the bound portion of the sample but in some cases may be at least slightly concave in the direction of the sample. Thus, the adhesion surface may have an area of at least about 25 μm² for a cell that is about 5 μm in (bound) diameter, at least about 100 μm² for a cell that is about 10 μm in (bound) diameter, and so on.

Binding, as used here, generally comprises any stable or semi-stable association between a sample and an adhesion surface that results in an electrical seal between the sample and one or more apertures that is sufficiently "tight" to allow the desired measurement. Binding may be mediated by any suitable mechanism, direct or indirect, including electrostatic interactions, covalent bonding, ionic bonding, hydrogen bonding, van der Waals interactions, and/or hydrophobic-hydrophilic$^v$ interactions, among others. In general, binding may be facilitated by the appropriate selection, treatment, and/or modification of the substrate, the sample, the measurement medium, or a suitable combination thereof.

Binding may be facilitated by appropriate selection of the substrate. Thus, preferred substrates typically include a relatively flat or gently contoured binding surface adjacent the aperture of interest, so that cells or vesicles may bind to form an acceptable seal with the aperture without unwanted or unnecessary deformation. Moreover, preferred substrates also typically include a modifiable binding surface, so that the surface may be treated as desired to promote binding.

Binding also may be facilitated by appropriate treatment of the substrate, as suggested above. Thus, in some applications, the surface may be treated or otherwise modified so that electrostatic or, in given cases, hydrophobic, van der Waals or covalent binding of vesicles or cells, or -the corresponding membranes or membrane fragments, is promoted. For example, the binding surface may be coated with an adhesion promoter, such as poly-L-lysine, poly-D-lysine, gelatin, collagen, laminin, fibronectin, proteoglycans, polyethylenimine, albumen, BIOMATRIX EHS (Nunc Nalge International), BIOBOND (Electron Microscopy Services, Inc.), and/or MATRIGEL (Becton-Dickinson), among others. Alternatively, or in addition, the binding surface is modified in a way that promotes molecule-specific binding, such as with avidin and/or biotin, or by modification with immobilized lectins. Alternatively, or in addition, the binding surface (especially a silicon binding surface) may be coated with an oxide or oxynitride layer. Alternatively, or in addition, the binding surface may be coated with largely hydrophobic compounds such as Tocopherol. In some embodiments, an electrically charged surface may be generated by modification, in particular, by means of polycations and/or silanes, for example, aminosilanes, or the substrate may have a coating or other surface layer with an electrically charged surface. Microstructured silicon/silicon oxide or silicon/silicon nitride substrates are especially suitable for providing a good electrostatic attraction, after being coated with a substance lending the desired surface charge. Finally, to improve the quality and consistency of the surface characteristics, the substrate may be subjected to oxygen plasma cleaned and/or partially or completely hydrophylized before the modification of its surface and/or before its immediate use, in addition to or in lieu of the above modifications. In some aspects of the invention, unwanted hydrophylization/modification of the hydrophobic surface can be avoided by using silicon nitride for the surface layer.

Binding also may be facilitated by appropriate selection and/or treatment of the sample itself. Thus, the sample may include unsaturated lipids or other compositions that increase the fluidity of its membrane, potentially enhancing membrane flexibility during binding and seal formation. Alternatively, or in addition, the sample may include charged lipids or other compositions that increase the charge on the sample, potentially enhancing the ability of the sample to bind electrostatically to substrate surfaces bearing an opposite charge. For example, for a positively charged substrate surface, the vesicle might include negatively charged palmitoyl-oleoyl-phosphatidylglycerol (POPG).

In some cases, binding may be facilitated by interactions between specific binding pairs (SBPs), where one member of the pair is associated with the sample and the other member of the pair is associated with the substrate. The interactions between members of a specific binding pair typically are noncovalent, and the interactions may be readily reversible or essentially irreversible. An exemplary list of suitable specific binding pairs is shown in Table 1.

TABLE 1

Representative Specific Binding Pairs

| First SBP Member | Second SBP Member |
|---|---|
| antigen | antibody |
| biotin | avidin or streptavidin |
| carbohydrate | lectin or carbohydrate receptor |

TABLE 1-continued

Representative Specific Binding Pairs

| First SBP Member | Second SBP Member |
|---|---|
| DNA | antisense DNA |
| enzyme substrate | enzyme |
| histidine | NTA (nitrilotriacetic acid) |
| IgG | protein A or protein G |
| RNA | antisense RNA |

Binding also may be facilitated by appropriate selection and/or treatment of the measurement medium. For example, the medium may include binding mediators that participate in or otherwise promote interactions between the sample and substrate, for example, by forming cross-bridges between the sample and substrate and/or by counteracting the effects of binding inhibitors associated with the sample, substrate, or medium. The binding mediators may act specifically, for example, by binding to specific groups or molecules on the sample or substrate. Thus, biotin might act as a specific binding mediator by binding to and cross-linking avidin or streptavidin on the sample and substrate. The binding mediators also may act less specifically, or nonspecifically, for example, by binding to classes or categories of groups or molecules on the sample or substrate. Thus, $Ca^{2+}$ ions might act as a relatively nonspecific binding mediator by binding to and cross-linking negative charges on the sample and substrate. $Ca^{2+}$ ions are particularly appropriate for mediating the binding of cells or vesicles containing negative lipids and substrates containing negative surface charges, such as $SiO_2$ substrates.

After binding, samples such as cells or vesicles may be broken up, for example, by treatment with a hypotonic medium, such as pure water.

Examples 1-7, 10, and 11 below, among others, describe exemplary adhesion surfaces, including materials, treatments, modifications, geometries, and the kinetics and efficacy of sample binding.

D. Fluid Compartments

The fluid compartments generally comprise any region or volume adapted to support a fluid adjacent the aperture. The compartments may perform several functions, including covering the sample, providing a medium through which the cell may be moved during positioning, and/or providing a medium for establishing electrical contact between the electrodes, among others. The compartments generally may have any suitable volumes, but they typically have volumes between about 0.1 to 40-100 µL. Thus, assays typically require only a limited amount of sample, facilitating the analysis of effects of precious compounds.

The fluid compartments may be closed or open. A closed compartment comprises a compartment that is at least substantially bounded or delimited on all sides by a wall or other separating layer, exclusive of an input and/or output port. In contrast, an open compartment comprises a compartment that is not bounded on at least one side (i.e., over at least some solid angle) by a wall.

Closed compartments typically are physically confined, i.e., bounded by some combination of the substrate, an electrode, and one or more spacers, being established within voids and channels therein. The spacers are used in many embodiments, particularly those involving planar electrodes, to establish and maintain the relative positions of the substrate and electrodes. Such spacers typically are formed of an electrically isolating material, like the substrate. The spacers may include channels disposed between the aperture and the electrode. These channels, typically filled with a conductive solution, can serve as a sample or reference chamber. It is beneficial if the reference chamber has such small dimensions that the reference buffer solution may be fixed therein by capillary forces, and/or forced therein by surface tension (e.g., at the fluid/air interface in an open compartment).

Open compartments typically are free standing, i.e., not bounded in at least one, typically lateral, direction. Instead, the fluid may be fixed between the substrate and electrode without other physical boundaries by capillary forces and/or surface tension.

Examples 2-7 below, among others, describe exemplary fluid compartments, including geometries, boundaries, and relationships with other components of the system.

E. Electrodes

The electrodes generally comprise any mechanism for creating and/or modulating an electric potential and/or current across an aperture and/or sample, or portion thereof, particularly for use in positioning and/or analyzing samples.

The electrodes may be formed of any suitable material, particularly those capable of inducing an electrical potential and/or current flow through an aperture and/or sample upon application of a physiological potential. Suitable electrodes include silver, gold, and/or platinum, among others. Preferred electrodes include silver/silver chloride (Ag/AgCl) and/or platinum (Pt) redox electrodes.

The electrodes may be formed with any suitable geometry and be disposed in any suitable arrangement, consistent with their performing their intended function(s). Preferred electrodes have planar, cylindrical, or point geometries. Preferred electrode arrangements are symmetrical, with similar electrodes positioned at similar distances and orientations from each aperture on each side. Symmetrical electrode arrangements generally will create symmetrical electric fields. Typically, the electrodes are located opposite one another across a single aperture, with each electrode reaching into at least one compartment, or at least contacting a surface of it. The electrodes customarily are located at a distance of about 0.5 to 3 mm, and usually about 0.5 to 1 mm, from the substrate, although they can be closer or farther in some embodiments. Depending on embodiment, the electrodes may be attached directly to a recording carrier, or to a cartridge in which this carrier is packaged, and/or to a holder that is not in direct contact to the substrate.

The electrodes may be selected and/or configured to perform any desired function, for example, positioning and/or analyzing samples, preferably without unduly disrupting the samples. Typically, this will involve creating and/or measuring at least one of an electric potential and a current. The electrodes may measure current selectively (i.e., ion specifically) and/or nonselectively. Preferred electric potentials give rise to electric field intensities of greater than about 100 V/m, particularly adjacent the aperture. In the following materials, one electrode may be referred to as a measurement electrode.

Examples 2-7 below, among others, describe exemplary electrodes, including geometries (e.g., planar, cylindrical, and point), materials (e.g., silver and/or platinum), and relationships with other components of the system.

F. Multiaperture Systems

The invention provides multiaperture systems for positioning and/or analyzing samples. These systems include two or more apertures, which may be disposed at the same and/or separate sites. Apertures disposed at the same site may be used to study single samples at two or more positions on the sample. In contrast, apertures disposed at separate sites may be used to study two or more samples, sequentially and/or simultaneously, at one or more positions on each sample. The production of multiaperture systems generally is straightforward, especially using silicon substrates and Ag/AgCl electrodes, both of which are easily microstructurable. In particular, multiaperture systems may be produced from a single continuous substrate having two or more apertures or by joining together two or more smaller substrates each having one or more apertures. The latter approach may be less expensive for substrates such as silicon with costs that increase faster than area.

Exemplary multiaperture systems employ a multiarray layout having a plurality of separate measurement sites. In these systems, each site includes at least one aperture and fluid and electrical contact with at least one fluid compartment and at least one electrode, respectively, on each side of the aperture. The fluid compartments and electrodes on one side of the substrate (the measurement side) generally are separated to allow independent recordings. However, the fluid compartments and electrodes on the other side (the reference side) may be partially or totally combined, because these components typically function merely to provide a common electrical potential (e.g., ground). The sample generally may be positioned on either the measurement or the reference side, although typically it is positioned on the measurement side so that each fluid compartment independently can contain the same or different types of samples. Thus, in these exemplary systems, several apertures may be used on one substrate, and the measurements may be performed over at least two apertures sequentially and/or in parallel and/or in such a manner that all or several electrodes on one side of the substrate have a common electrical potential, or, alternatively, are combined to form one electrode. Similarly, more than two electrodes and more than one aperture can be present in such a way that at least one electrode, for example, a reference electrode, serves the measurement via more than one aperture, or the measurement arrangement can have a substrate with more than one aperture and twice as many electrodes as apertures in such a way that one aperture always is located between two electrodes.

Measurement sites may be separated using any suitable mechanism, including hydrophilic/hydrophobic surface patterning, as described below, and/or dividing the carrier surface into small compartment wells (e.g., by laminating a thin polydimethylsiloxane (PDMS) layer containing small holes to the carrier surface adjacent the aperture).

The multiaperture system generally may include any number of measurement sites, positioned in any suitable arrangement, with any suitable size or footprint, all consistent with forming electric fields within each site to position and/or analyze samples. Preferred configurations may be selected based on utility and/or convenience. Thus, preferred systems may include features selected from standard microplates, so that the system may be used with standard microplate equipment, including handlers, washers, and/or readers, among others. These features may include a rectangular frame, with a major dimension of about 125-130 mm, a minor dimension of about 80-90 mm, and a height of about 5-15 mm, although other dimensions are possible. The frame may include a base configured to facilitate handling and/or stacking, and/or a notch configured to facilitate receiving a cover. These features also may include 96, 384, 864, 1536, 3456, or 9600 measurement sites, among others, positioned on a rectangular or hexagonal array. Three exemplary configurations that will fit as rectangular arrays within a microplate-sized frame are listed in the following table:

| Number of Sites | Arrangement of Sites | Pitch (mm) Between Sites | Density (/mm²) of Sites |
| --- | --- | --- | --- |
| 96 | 8 × 12 | 9 | 1/81 |
| 384 | 16 × 24 | 4.5 | 4/81 |
| 1536 | 32 × 48 | 2.25 | 16/81 |

Here, pitch is the center-to-center site-to-site spacing, and density is the number of sites per unit area. These features also may include the color of system components, particularly components in the optical path in optical assays. For example, in fluorescence applications, system components preferably are made of opaque black plastic to reduce background photoluminescence and/or "crosstalk," where crosstalk is the transmission of light emitted in one site to adjacent sites where it may be detected. In contrast, in chemiluminescence applications, system components preferably are made of opaque white plastic to increase reflection of emitted light out of the site by the white surfaces while still reducing crosstalk.

Examples 5 and 6 below, among others, describe exemplary multiaperture positioning and/or analysis systems, including additional features such as reference fiducials not described above.

G. Analysis System

The positioning and measurement system of the present invention optionally may be coupled to or integrated with an analysis system for analyzing samples and sample components. The analysis system generally comprises any mechanism for analyzing or otherwise characterizing samples, qualitatively or quantitatively, other than by direct electrical measurement as used by the positioning and measurement system. The analysis system may require that the sample be separated from the measurement system and/or from other sample components, as described above. Alternatively, or in addition, the analysis system may allow the sample to be studied in situ, without such separation. Generally, measurements made by the positioning and measurement system and measurements made by the analysis system may be performed simultaneously or sequentially, in any order or in any combination, in association with or independent of one another.

The analysis system may be based on any suitable analytical technique, including spectroscopic, hydrodynamic, and imaging methods, among others, particularly those adaptable to high-throughput analysis of multiple samples. Preferred analysis systems are based on the optical analysis of samples, particularly luminescence-based optical analysis, but also absorption, scattering, circular dichroism, optical rotation, and imaging, among others. In luminescence analysis, light transmitted from the sample is detected and analyzed, and properties of the detected light are used to infer properties of the sample, including the presence, size, shape, mobility, quantity, activity, and/or association state of selected components of the sample. In photoluminescence, including fluorescence and phosphorescence, the emission of light from the sample is induced by illuminating the sample with appropriate excitation light. In chemiluminescence, the emission of light from the sample is induced by chemical reactions occurring within the sample. The analysis may involve measuring various properties of the detected light, including its intensity, lifetime, polarization, quantum yield, and Stokes' shift, among others. The analysis also may involve using one or more of these properties in techniques such as fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and fluorescence imaging, including confocal CCD observation, among others.

In luminescence assays, light typically is detected from a luminophore, i.e., a molecule or other species that emits luminescence. The luminophore may be endogenous or exogenous. Moreover, the luminophore may be the material of interest in the assay but more commonly is simply a reporter that provides information about another material that is the true material of interest. In particular, the luminophore may be an exogenous molecule that reports on (1) membrane potential, (2) the presence or concentration of a target metal, such as $Ca^{2+}$, $Mg^{2+}$, and $Zn^{2+}$, (3) the presence or concentration of an inorganic ion, such as $Na^+$, $K^+$, and $Cl^-$, (4) pH, (5) reactive oxygen species, including nitric oxide, (6) ion channels, including $Ca^{2+}$ channels, $Na^+$ channels, $K^+$ channels, and $Cl^-$ channels, (7) signal transduction, (8) cell viability, and (9) endocytosis and exocytosis, among others. Suitable luminophores for reporting on this and other information are described in Richard P. Haugland, *Handbook of Fluorescent Probes and Research Chemicals* ($6^{th}$ ed. 1996), which is incorporated herein by reference in its entirety for all purposes.

The combination of optical technologies with the patch-clamp technologies presented here permits, for the first time, the distinction or resolution of ligand binding events and channel activities, among others. In this way, for example, important information regarding the stabilization of changes in receptor conformation through ligand binding and/or the functional variation in ligand binding sites in receptors may be obtained.[vii] Such information is potentially important for understanding the particular mode of action of individual agonists and antagonists, and thus exhibits great promise for future drug development.

The optical analysis system typically will include a light source, a detector, and one or more optical relay structures for directing excitation light from the light source to the sample and for directing emission light from the sample to the detector. However, the light source and excitation optical relay structure are optional during analysis utilizing chemiluminescence methods. The optical analysis system may use epi- and/or trans-detection schemes, involving illuminating off of and/or through the sample, respectively.

Exemplary optical analysis systems, and components thereof, are described below under Examples and in the various patents, patent applications, and other materials listed above under Cross-References and incorporated herein by reference. Preferred optical analysis systems are described in the following materials, which are incorporated herein by reference in their entirety for all purposes: U.S. Pat. No. 5,355,215, issued Oct. 11, 1994; U.S. Pat. No. 6,097,025, issued Aug. 1, 2000; U.S. Provisional Patent Application Ser. No. 60/267,639, filed Feb. 10, 2001; and Joseph R. Lakowicz, *Principles of Fluorescence Spectroscopy* ($2^{nd}$ ed. 1999).

The combined system is suitable for simultaneous and/or sequential electrical and optical (e.g., photoluminescence) measurements. Suitable apparatus may include a planar, and vertically easily realizable, optically transparent structure, for example, with the use of planar pointed electrodes, or alternatively point electrodes disposed outside of the vertical lines going through the aperture. This allows not only fluorescence or electrical analysis of single cells (or membranes) but also the combined optical-electrical observation of cells (or membranes), particularly in response to exposure to externally applied substances, such as potential medical drugs. This revolutionary approach allows significantly more efficient selection of new drugs and the elucidation of their molecular action.

Example 7 below, among others, describes an exemplary analysis system. Additional examples are described in the various patents and patent applications listed above under Cross-References and incorporated herein by reference.

H. Sample-Handling System

The positioning and measurement system according to the invention optionally may be coupled to or integrated with a sample-handling system for adding, manipulating, exchanging, and/or removing samples and sample components, including cells and vesicles, sample media, and compounds and reagents, such as candidate modulators and/or other analytes. The sample-handling system may add samples such as cells or vesicles to arbitrary compartments, convey liquid into and/or out of arbitrary compartments, and/or exchange samples and/or liquid between arbitrary compartments, among others. The sample-handling system also may separate samples, or sample components, in particular using capillary electrophoresis (CE) and/or high-pressure liquid chromatography (HPLC), and serve the analysis of the separated substances, or it can be provided with means that serve the continuous or regular testing of the state of the liquid in the compartments as well as with means for retroactive regulation according to preset filling parameters. Because it is reasonable, according to the analysis strived for, to bring the membrane into contact with measurement solution on both sides, the addition of a substance to be investigated obviously can be done on the side customarily serving as the reference side. The sample-handling system may be multiplexed to interact with several substrates and/or with a multiaperture substrate, among others.

The sample-handling system may be based on any suitable mechanism, including tubes, pumps, hydrostatic pressure differentials, electro-osmotic processes, piezo drop-on-demand processes, ink-jet processes, contact transfer processes, temperature-controlled processes, and/or mechanical displacement, among others. In some embodiments, fluids such as reference buffers may be introduced into a pasty gel, whereby an exchange of the liquid lying outside the gel is possible without changing the composition of the reference buffer stored in the gel. Suitable gels include agarose and polyacrylamide.

Example 2 below, among others, describes an exemplary sample handling system. Additional examples are described in the various patents and patent applications listed above under Cross-References and incorporated herein by reference, including U.S. patent application Ser. No. 09/777,343, filed Feb. 5, 2001 (now U.S. Pat. No. 6,902,703 1); and U.S. Provisional Patent Application Ser. No. 60/267,639, filed Feb. 10, 2001.

I. Samples

The sample generally comprises any species having a membrane or other surface capable of forming a seal with an aperture sufficient for performing electrical measurements such as patch clamp experiments. The sample may include cells, vesicles, cellular organelles, membrane-bound viruses, and fragments, derivatives, and mixtures thereof Biological samples may include or be derived from (1) eukaryotic cells, i.e., cells with a nucleus, including cells from plants, animals, fungi, yeast, and protozoans, or enucleated derivatives thereof; (2) prokaryotic organisms, including bacteria and archaebacteria; (3) viruses; (4) organelles or extracts, such as nuclei, mitochondria, endosomes, the Golgi apparatus, peroxisomes, lysosomes, endoplasmic reticulum, chloroplasts, axons, and dendritic processes, among others; and (5) gametes, including eggs and sperm. These cells and other materials may be obtained from any suitable source, including cell cultures, patient samples, and tissues, among others. These cells also may be subjected to any suitable treatments to alter membrane properties, for example, to introduce a novel or modified ion channel, among others. These treatments may include genetic modification by any suitable method, including chemical treatment, irradiation, transfection, infection, and/or injection, among others.

Vesicles and other synthetic samples may include or be derived from (1) unilamellar vesicles, (2) multilamellar vesicles, (3) small vesicles (having diameters less than about 1000 nm), (4) large vesicles (having diameters greater than about 1000 nm), (5) monodisperse vesicles, and (6) polydisperse vesicles. These vesicles may be formed from any suitable lipid(s) and/or protein(s) using any suitable technique. Exemplary lipids include DLPC, DMPC, DPPC, DSPC, DOPC, DMPE, DPPE, DOPE, DMPA, DPPA, DOPA, DMPG, DPPG, DOPG, DMPS, DPPS, and DOPS, among others.

Examples 8 and 15-18 below, among others, describe exemplary samples, including vesicle and cell samples.

J. Sample Positioning

The electrical, optical, and/or other analysis of samples generally is preceded by a positioning step, in which the sample is directed to or otherwise located at the adhesion surface. Sample positioning generally occurs in two sequential substeps: (1) a first (prepositioning) substep, in which the sample is introduced to the measurement compartment, and (2) a second (micropositioning) substep, in which the sample is brought into proximity or actual contact with the adhesion surface. These steps may be performed robotically, at least substantially without direct human involvement or intervention.

The prepositioning substep generally involves introducing the sample to the measurement compartment, preferably in a manner that facilitates subsequent binding of the sample to the adhesion surface. Thus, the sample may be introduced generally above the adhesion surface (or associated aperture), so that it is directly between the electrodes, if they are symmetrically arranged, and so that gravity will tend to pull it straight down toward the aperture. Alternatively, or in addition, the sample may be introduced relatively close to the adhesion surface, and/or with an initial velocity toward the adhesion surface, among others.

The micropositioning step generally involves bringing the sample into proximity or actual contact with the adhesion surface, once the sample is in the measurement compartment. Generally, samples may be micropositioned using any suitable force or other mechanism, including sedimentation (e.g., "1 g-sedimentation" under the influence of gravity), electromagnetic forces (e.g., electrophoresis, electro-osmosis, and the like), optical forces (e.g., optical tweezers), fluid-mediated forces (e.g., pressure, vacuum, flow, diffusion, and the like), and/or manual forces. Alternatively, or in addition, the cells may be positioned by fluid flow from the sample compartment to the reference compartment by a hydrostatic pressure difference or by a difference in surface tension between the two compartments. Preferably, samples are micropositioned using electromagnetic forces, specifically, field focusing of an electric field created by applying a potential across the two electrodes. In brief, this technique exploits the field focusing that occurs adjacent the aperture, creating an electric force that, at least adjacent the aperture, points in all positions toward the aperture, with a strength that increases with proximity to the aperture.

Examples 2 and 9 below, among others, describe exemplary methods for prepositioning and micropositioning samples, respectively.

K. Measurement Process

The measurement process provided by aspects of the invention allows in particular the measurement of ion channel flows in a reliable and reproducible manner, often with a high signal-to-noise ratio. These abilities reflect the precise positioning and electrically tight binding of cells, vesicles, cellular organelles, and/or membranes of corresponding origin, at microstructured apertures in a planar substrate. This electrically tight binding may be achieved at least in part by strong interactions between the surface of the substrate and the surface of the bound membrane, such as strong electrostatic attractions.

The electrical characteristics of transmembrane ion channels or ionotropic receptors may be characterized using "voltage-clamp technologies," such as classical voltage-clamp, patch-clamp, and oocyte voltage-clamp, among others.[viii] Specifically, an electrical potential difference is applied across the membrane containing the relevant ion channel(s), and, simultaneously, the current necessary to maintain this difference is analyzed. The relationship between the voltage and current may be expressed mathematically using Ohm's Law, which states that V=IR, or equivalently, I=V/R, where V=voltage, I=current, and R=resistance. The current provides insight into membrane electrical properties, such as its conductivity, and therefore insight into the conformation state of the channel-forming protein (e.g., open (passing ions) or closed (blocking ions)). Thus, the current may be used to analyze voltage dependencies, ligand binding events, and so on.

The ability of current measurements to yield meaningful data in a patch clamp or other electrophysiology experiment is dependent on ensuring that the measured current reflects ion flow through the sample (e.g., through ion channels in the membrane) and not through other components of the system. In particular, to obtain acceptable or better signal-to-noise ratios, it typically is desirable to ensure that the measured current includes no more than a ten or twenty percent contribution from unintended sources (e.g., that sources of noise lie under the signals to be measure by approximately the factor of five or ten). Unfortunately, the ion flow through ionotropic membrane proteins with 0.1 to 50 pA at a −60-mV membrane potential is in general very small, so that leakage currents occurring essentially between the membrane and its fastening quickly may become significant, representing a principal problem in all voltage-clamp technologies.

The problem of leakage currents can be solved in a variety of ways. For example, enlarging the aperture and thereby the patch of membrane to be analyzed may reduce the contribution of leakage currents to the total signal, because the area of the membrane patch and so the intended signal will grow as the radius of the aperture squared, while the circumference of the membrane and so the leakage current will grow merely as the radius. Unfortunately, increasing the size of the membrane may lead to a loss in specificity, particularly in biological systems, because more channels and more types of channels will be in the membrane area analyzed. Then, in general, an unambiguous or completely artifact-free statement, for example, in the case of the addition of ligands, may no longer be possible.

Establishing and maintaining a very high seal between the membrane and aperture also may reduce the contribution of leakage currents. This invention uses this principle, at least in part. To implement the seal, a planar substrate chip having a surface that is strongly adhesive for cells and vesicles is used. This chip separates the two compartments clamped at different potentials during the measurement, where a (sub) micrometer-sized aperture is located in its middle. This aperture is filled with reference buffer solution and electrically tightly sealed during current measurements by strong binding of cells and vesicles to the surface. This electrically tight binding may permit the measurement of very small ion flows (e.g., down to at least about 0.1 pA) and, concomitantly, the plotting of membrane resistance with a good or better signal-to-noise ratio.

Further (mechanical) stability may be derived from using capillary forces to fill and store the reference and/or measurement buffers. In particular, unbounded or open fluid compartments may experience fewer disturbances (e.g., due to temperature differentials) of the membrane due to hydrostatic pressure than closed systems.

The measurement systems described here may be used for a variety of applications, some of which are described below in Example 16, including "perforated-patch," "whole-cell," and "inside-out" patch clamp techniques. For example, measurement systems of the planar type are particularly well suited, due to the short diffusion times associated therewith, to the use of "perforated-patch" techniques.[ix] In these techniques, an electrical connection to the interior of the cells (cytosol) is achieved by permeabilization of the area of the membrane suspended across the aperture with pore-forming antibiotics. An advantage of this technique is that it does not require washing out the cytosol with measurement buffer solution for simultaneous electrical access. In particular, a pore former such as, for example, amphotericin B or nystatin can be added to the reference compartment, after a biological cell, or, under special circumstances, a vesicle (if its mechanical stability is sufficiently high) is bound to the upper side of the aperture. In doing so, the rate of perforation of the membrane patch over the aperture is significantly greater than in comparable standard patch-clamp techniques.

For example, measurement systems of the planar type also are particularly well suited to the use of "whole-cell" techniques. In these techniques, an electrical connection to the cytosol is achieved by destroying the membrane patch, for example, using a voltage pulse. This destruction, in turn, may facilitate the simple addition of larger proteins into the cytoplasm, via the reference solution, again because the planar layout of the measurement system allows significantly faster diffusion of large macromolecules into the cytosol or the interior of a vesicle than comparable standard whole-cell techniques.[x]

The system facilitates the addition and/or exchange of various system components, including solutions and/or substances, as suggested above. For example, in some applications, the measurement solution, the reference solution, or both solutions may be replaced by another solution. Alternatively; or in addition, a substance to be analyzed may be added to the solution on the measurement and/or reference side, The substance may include a pore former that can be added to one or both compartments with the aim of increasing the electrical conductivity, or, alternatively, the permeability of the membrane wit respect to certain ions. The substance also may include detergent-solubilized proteins or proteoliposomes of arbitrary size, with the aim of fusing them to the membrane over the aperture and thereby making arbitrary membrane proteins contained therein accessible to electrical or optical measurements. The fusion of proteoliposonies is described in detail in U.S. patent application Ser. No. 09/952,461, filed Sep. 14, 2001 (now abandoned).

Examples 12-21 below, among others, describe exemplary results obtained from various electrical measurements on vesicle and cell-derived membranes.

EXAMPLES

The following examples describe selected aspects and embodiments of the invention. These examples are included for illustration and should not be interpreted as restricting, limiting, or defining the entire scope of the invention. Additional examples are described in the following patent applications, which are incorporated herein by reference in their entirety for all purposes: U.S. patent application Ser. No. 09/581,837, filed Jun. 16, 2000; U.S. patent application Ser. No. 09/952,461, filed Sep. 14, 2001; U.S. Provisional Patent Application Ser. No. 60/322,178, filed Sep. 13, 2001; U.S. patent application Ser. No. 09/957,116, filed Sep. 14, 2001; and U.S. patent application Ser. No. 10/093,680, filed Mar. 7, 2002.

Example 1

Substrate Chip

This example, illustrated in FIG. 2, describes an exemplary Si/SiO$_2$ chip substrate 50 for use in positioning and/or studying cells, vesicles, and the like, in accordance with aspects of the invention.

The substrate includes a body 52, a surface layer 54, a window 56, and an aperture 58. The body comprises an at least substantially planar, commercially available silicon wafer. The surface layer comprises a silicon oxide or silicon oxynitride layer formed adjacent one or more sides of the body. In this embodiment, the surface layer has a thickness of at least about 50 to 200 nm and provides at least one adhesion surface 60a,b capable of binding cells, vesicles, and/or other samples. The window and aperture comprise openings through the body and surface layer, respectively. These openings are at least substantially concentrically aligned, with dimensions sufficient to allow fluid contact between opposite sides of the substrate.

The substrate may be produced using any suitable method, including photolithography or, for apertures having diameters of less than about 1.5 µm, electron beam lithography. These methods may involve anisotropic etching of the silicon in a medium containing KOH, as well as reactive ion etching of the silica layer.

In alternative embodiments, the substrate may include a body and/or a surface layer having a different geometry and/or formed of different materials. In addition, the window may be absent, or the window and the aperture both may be openings in the body, particularly in embodiments lacking a surface layer.

Example 2

Measurement System with Planar Electrodes

This example, illustrated in FIG. 3, describes an exemplary measurement system 70 having planar electrodes, in accordance with aspects of the invention.

The measurement system includes a substrate 72, at least two fluid compartments 74a,b, at least two redox electrodes 76a,b, and optionally at least four spacers 78a-d. In this embodiment, all of these components are at least substantially planar; however, in other embodiments, one or more of these components may have a different geometry. Generally, samples may be introduced into either compartment, and measurements may be performed with the system in any orientation. However, to simplify the description, the top fluid compartment 74a and top electrode 76a (as drawn) are referred to here as the measurement compartment and measurement electrode, and the bottom fluid compartment 74b and the bottom electrode 76b (as drawn) are referred to as the reference compartment and the reference electrode.

The substrate is used to support cells, vesicles, and other samples for electrical analysis. The substrate includes a body 80, a window 82, and an aperture 84 connecting the two fluid compartments. The substrate further includes at least one adhesion surface 86a,b positioned adjacent one or both ends of the aperture for binding cells, vesicles, and/or other samples. An exemplary substrate is described in more detail in Example 1.

The fluid compartments are used to support fluids such as electrolyte solutions or growth media in apposition to the substrate and aperture. The compartments are formed by apertures or voids in the substrate, spacers, and/or electrodes.

The electrodes are used to apply and/or measure an electric potential and associated electric field across the aperture. Measurement electrode 76a comprises a 0.8-mm thick chlorinated square (e.g., 4×4 mm$^2$) or annular (e.g., d=2 mm) silver (Ag) plate, preferably having a frustoconical or funnel-shaped opening 88 (e.g., $d_{min}$=0.4 to 1 mm). The measurement electrode is positioned at least substantially parallel to the surface of the substrate, preferably at a distance of up to about 1 mm from the surface of the substrate. The measurement electrode further is positioned so that opening 88 is at least substantially concentrically positioned above aperture 84. Reference electrode 76b comprises a 2-mm thick square silver plate (e.g., 20×20 mm$^2$), which preferably has a purity greater than about 99.98% silver. The preferred silver/silver chloride (Ag/AgCl) reference electrode may be produced during manufacture of the system, for example, (1) by exposing the reference compartment to a molecular Cl$_2$ gas, typically while applying a potential to the electrode, or (2) by filling the reference compartment with 1 M HCl, and then chlorinating the exposed silver for 90 seconds under a 0.8-V potential. The substrate is mounted, after its underside is wetted with buffer solution, over the reference compartment filled with reference buffer solution. In this embodiment, the reference electrode functions to support and maintain other components of the system.

The spacers may be used for several functions, including (1) separating the substrate and electrodes, (2) forming the fluid compartments, and (3) contributing to the structure of a feed opening 90 used to introduce samples to the sample compartment. Specifically, first and second spacers 78a,b are positioned about the measurement electrode. These spacers include openings 92a,b that may be aligned concentrically with opening 88 in the measurement electrode and aperture 84 in the substrate to form a "feed opening" for introducing samples into the system. The feed opening may be of arbitrary form; typically, however, it is elliptical, in particular circular, with a preferred diameter of about 0.2 to 2 mm, and a more preferred diameter of about 0.5 to 1 mm, to facilitate its concentric alignment with the aperture. A third spacer 78c is positioned between the measurement electrode and the substrate to form an insulating barrier between these two elements. This spacer, preferably formed from silicone (e.g., Sylgard 184, Dow Corning, USA), includes a ring-like opening 92c that again may be mounted concentrically about aperture 84, for example, with a radius r of about 1 mm. The ring-like opening forms, together with the meniscus that forms between the chip and measurement electrode, the sample chamber (sample compartment) for the addition of cells, vesicles, and/or measurement solution. Finally, a fourth spacer 78d is positioned between the reference electrode and the substrate to forming an insulating barrier between these two elements. This spacer, preferably formed as a 0.5 to 2 mm-thick silicon rubber seal (e.g., Sylgard), includes a channel or chamber 92d having dimensions of about 1 mm in width and less than about 6 mm in length. The spacer may be imprinted and, if filled with buffer solution, produce contact between the aperture, or alternatively the membrane, and the reference electrode.

The measurement system may be configured or adapted to facilitate the addition, positioning, and/or analysis of samples. Thus, the setup preferably has means on one or both sides of the substrate that make possible an addition of liquid, a storage of liquid, and, in given cases, an exchange of liquid, as well as the addition of cells, vesicles, or other cellular organelles, or parts of the same, between the substrate and the electrode(s). For example, during measurement, or membrane production, a small (e.g., 5 to 10 μL) volume of measurement or vesicle solution (e.g., a cell suspension) may be added (e.g., by pipette) directly to the feed opening, the window, and/or the aperture, on the measurement side of the substrate or on the upper side of the measurement electrode. The aperture preferably has a diameter such that, when a voltage differential exists over the chip, an inhomogeneous electrical field, mediated by the electrodes, is set up around the aperture. This field may increase in magnitude near the aperture, such that samples can be moved electrophoretically toward the aperture. Furthermore, the substrate preferably includes at least one surface 94a,b, on one or both sides of the aperture, that is attractive for biological membranes, permitting the molecule-specific and/or multivalent ion-mediated binding of cells, vesicles, membrane fragments, and/or cellular organelles. The surface of the substrate further may be structured to create hydrophilic and hydrophobic areas, with the hydrophilic area preferably positioned around the aperture.

Example 3

Measurement System with Point or Wire Electrodes

This example, illustrated in FIG. 4, describes an exemplary measurement system 110 having point or wire electrodes, in accordance with aspects of the invention.

The measurement system includes a substrate 112, two fluid compartments 114a,b, and two point or wire electrodes 116a,b. The substrate and fluid compartments are used to support samples and fluids, respectively, as described above. The substrate includes a body 118, a window 120, and an aperture 122 connecting the two fluid compartments. The substrate further may be surface modified and/or fastened to a holder, including a glass or Teflon holder. The electrodes are used to apply an electric potential and associated electric field across the aperture, also as described above. Here, the electrodes comprise the chlorinated end surfaces 124a,b of two silver wires 126a,b, or, alternatively, two silver electrodes, disposed above and below the substrate. The electrodes preferably have diameters between about 0.1 and 2 mm and a relative separation of about 4 mm. In some embodiments, the electrodes may be provided with a protective outer layer 128a,b that covers and protects the outside surface of the electrodes, except at the end surfaces.

The measurement system may be used for positioning and/or analyzing samples. In an exemplary approach, sample medium is added to both sides of the substrate, and held between the substrate and electrode by capillary forces. Next, the offset is calibrated, and a suitable voltage is applied (typically, V=−60 to −100 mV). Then, cells or vesicles are added to an appropriate (e.g., modified) side of the substrate, and cell binding and/or membrane formation are pursued with the aid of a change in the electrical parameters. Finally, the properties of ion channels or other membrane components are studied using suitable electrophysiology methods. Throughout, the addition or exchange of samples and/or sample media may be performed using a sample handling system, as described above, such as a pipette or tube mounted near the aperture.

Example 4

Measurement System Having Open Fluid Compartments

This example, illustrated in FIG. 5, describes an exemplary measurement system 150 having open fluid compartments, in accordance with aspects of the invention.

The measurement system includes a substrate 152, at least two fluid compartments 154a,b, and at least two electrodes 156a,b. These components perform at least substantially the same functions as their namesakes in Examples 2 and 3.

The substrate comprises an insulating silicon chip 158. The substrate may include a groove that is closed by a thin silicon nitride ($Si_3N_4$) 160/silicon oxide ($SiO_2$) 162 diaphragm containing a small aperture 164 having a diameter that usually is less than about 20 μm. The substrate further may include a surrounding insulating layer 166, for example, thermally grown silicon oxide, to reduce system capacitance. The surface of the substrate may be treated to promote the tight adhesion of cell or vesicle-associated lipid bilayers, for example, by (1) physisorption of poly-L-lysine (with a typical molecular weight greater than about 15,000 daltons), (2) chemical modification with 4-aminobutyl-dimethyl-methoxysilane, and/or (3) attachment of molecules that bind (specifically or nonspecifically) to the cell surface (e.g., lectins), among others.

The fluid compartments comprise open regions of the substrate surface adjacent the aperture to which fluid is confined. Here, fluid is confined by a combination of hydrophilic and hydrophobic interactions. Specifically, fluid is attracted to the region adjacent the aperture by hydrophilic interactions and excluded from regions away from the aperture by surrounding layers of hydrophobic material 168a,b attached or bound to the surface. Consequently, the buffer compartments are delineated by the surface of the substrate on one side and by surface tension on the opposing side, creating dome-shaped compartments, as shown.

The electrodes comprise conductive elements such as Ag/AgCl for generating an electric potential across the aperture. The electrodes, which may be used for positioning and/or recording, are immersed in the fluid compartments. The electrodes may be directly attached to the substrate (e.g., by sputtering or printing) or to a container that contains the substrate. Here, a first (measurement or recording)

electrode is used to apply a measurement voltage, and a second (reference) electrode is used to apply a ground.

The measurement system may be used for positioning and/or analyzing samples, at least substantially as described above. In particular, upon application of a voltage between the two fluid compartments, mediated by the redox electrodes immersed in the two compartments, a strongly inhomogeneous field is created around the aperture that attracts cells, vesicles, and other charged objects towards the aperture. After these samples bind and/or form membranes, they may be analyzed electrically and/or optically, among others.

Example 5

Measurement System Having Multiple Measurement Sites

This example, illustrated in FIGS. 6 and 7, describes an exemplary measurement system 190 having multiple measurement sites, in accordance with aspects of the invention. The drawings show two alternative embodiments, separated by break lines, that include different carrier/electrode configurations.

The measurement system includes a plurality of measurement sites, each capable of positioning and/or analyzing a sample, as described above. More specifically, the measurement system includes a substrate 192, a plurality of fluid compartments 194a,b, and a plurality of electrodes 196a,b. The measurement sites are formed from portions of the substrate and combinations (e.g., pairs) of fluid compartments and electrodes. The substrate preferably comprises (1) a silicon body 198, (2) a silicon nitride diaphragm 200 having a plurality of apertures 202, at least one per measurement site, and (3) a hydrophobic and/or insulating surface coat 204. The fluid compartments preferably comprise (1) a plurality of measurement compartments 194a, and (2) at least one reference compartment 194b. The electrodes preferably comprise (1) a plurality of measurement electrodes 196a, at least one per aperture or measurement site, and (2) at least one reference (ground) electrode 196b. The measurement system further may include additional features, such as (1) a support or carrier plate 206 to simplify the design and/or to increase the reliability of the system, and/or (2) one or more reference fiducials 207 for reference and/or alignment purposes, as described below.

The components of the measurement system are described in more detail in subsequent subsections. Briefly, on one side, the substrate contains a patterned surface that physically separates the measurement compartments, allowing independent measurements. The patterned surface may be created by the patterned attachment of hydrophilic materials at measurement sites and hydrophobic materials at intervening positions. The measurement compartments may be accessed independently using a separate measurement electrode for each compartment, where each electrode is connected independently to one or more voltage sources, such as a voltage clamp circuit. On the other side, the substrate contains a reference compartment that can be separated but that preferably is unified to form a single compartment in contact with a single (usually ground) electrode. In some embodiments, the substrate includes a silicon chip containing grooves that are closed by a silicon nitride/silicon oxide diaphragm. The diaphragm includes a small aperture having a diameter of less than about 20 µm. The substrate otherwise may be surrounded by an insulating layer, for example, a thermally grown silicon oxide layer, to reduce the system capacitance.

5A. Substrate

The substrate generally comprises any structure adapted to provide two or more sites for positioning and/or analyzing samples electrically, as described above. The substrate may be formed from any suitable material, including silicon, plastic, and/or glass. The substrate generally may include any number of sample sites arranged in any suitable format, as described above. Preferred formats include 8×12 (96) rectangular arrays and 16×24 (384) rectangular arrays, with standard microplate footprints. Some embodiments may include additional sites, including additional rows or columns of sites. For example, in one such embodiment, the system includes an additional row of sites, configured as an 8×13 (104) rectangular array.

5B. Fluid Compartments

The fluid compartments generally comprise any region adapted to support fluid for bathing the sample and for providing electrical contact between the measurement and reference compartments.

The measurement compartments are used for positioning and/or analyzing samples. These compartments are defined by hydrophilic spots on the chip surface, surrounded by a hydrophobic surface coating, for localizing fluid. The measurement compartments include an aperture positioned within the hydrophilic spot and a measurement electrode positioned for electrical contact with the associated measurement fluid. The hydrophilic spot typically includes an at least substantially planar or concave adhesion surface, which may be selected and/or treated as described above to promote sample binding and/or membrane formation.

The reference compartments are used for completing the electric circuit, typically to electric ground. These "backside" compartments may be combined to form one or more large compartments (corresponding to two or more measurement compartments), since the separate compartments typically would contain the same buffer solution and each be connected to ground. In particular, a single large backside compartment and a single backside electrode are sufficient for spatial resolution of individual recordings, if the measurement compartments are addressed individually. In some embodiments, the backside electrode may be deposited directly on the recording chip or on an embedding cartridge.

5C. Electrodes

The electrodes generally comprise any mechanism adapted to apply and/or measure an electric potential across the aperture, with each measurement site in contact with at least one measurement electrode and at least one reference electrode, as described above.

The composition of the electrodes is selected to allow current flow at physiological potentials. Preferred electrodes include silver/silver chloride (Ag/AgCl) and/or platinum (Pt) redox electrodes for both the sample and reference compartments. Particularly preferred electrodes include silver (Ag) as the electrode material, chlorinated within a chlorine ($Cl_2$) atmosphere.

The number of electrodes may vary. The upper side of the substrate (associated with the measurement compartments) preferably includes enough separate electrodes independently to address each corresponding recording site, e.g., 8×13 electrodes on a 2.25 mm grid. In contrast, the lower side of the substrate (associated with the reference compartment) preferably includes a single electrode.

The electrodes may be insulated outside the measurement compartment. Preferred insulation material preferably has a high electrical resistance and a low dielectric constant and loss. Particularly preferred insulation material is produced from Teflon, silicon nitride ($Si_3N_4$), and/or Sylgard by spin coating or chemical vapor deposition (CVD). These materials are sufficiently hydrophobic (even after short oxygen-plasma treatment) to confine the measurement and reference compartments. Moreover, these materials may include or be formed to include grooves or holes, potentially improving fluid support and/or reducing evaporation.

The electrodes at the various measurement sites may be connected electrically to corresponding contacts 208 for clean and/or easy access to appropriate electronic components, such as amplifiers, recording devices, and the like. In a preferred embodiment, the contacts are positioned near the edge or border of the substrate, and a bonding wire 210 joins the electrodes and contacts, although more generally any mechanism capable of establishing an electrical connection may be employed. In particular, the electrodes can be bonded to contacts placed on a plastic (e.g., polypropylene) carrier that embeds the entire recording chip.

5D. Support Element

The support element generally comprises any mechanism for independently and portably supporting the substrate and associated system components, potentially simplifying design and/or increasing reliability. The support element may support the substrate at its edges and/or in its interior, with the interior support potentially reducing or preventing sagging and/or stress of the substrate. In an exemplary embodiment, the support element includes a carrier plate 206 and a spacer 212 sandwiched between the substrate and the carrier plate near the edges of the substrate. The carrier plate may be formed from glass (e.g., PYREX) and/or any other suitable material. The substrate, spacer, and carrier plate may be joined using any suitable mechanism, such as anodic bonding. The separation between the substrate and the carrier plate (i.e., the spacer thickness) preferably is chosen to be less than about 1 mm, to allow filling of the backside (i.e., reference) compartment by capillary forces. By extending the glass plate over the borders of the chip, in some embodiments, it may be possible to bond the upper electrodes to contacts placed on the glass plate.

5E. Reference Fiducials

The reference fiducials generally comprise any feature or characteristic of the measurement system adapted to provide information that facilitates sample handling and/or analysis, for example, as described in U.S. Pat. No. 6,258,326, issued Jul. 10, 2001, which is incorporated herein by reference in its entirety for all purposes.

The reference fiducials, or a subset thereof, may be used to encode information and/or to provide reference positions. For example, the reference fiducials may encode information relating to the identity of the manufacturer of the system and/or one or more properties of the system and/or the associated samples. Alternatively, or in addition, the reference fiducials may provide reference positions useful to correct for cross-system drift (due to dimensional irregularities in the system) and/or to align the system with ancillary devices, such as an electrical device for electrical analysis and/or an optical device for optical analysis.

The reference fiducials may encode information using any suitable mechanism, including electrical and/or optical mechanisms. For example, the reference fiducials may encode information electrically, based on the resistance, capacitance, and/or inductance, among others, of a particular portion or portions of the system. Alternatively, or in addition, the reference fiducials may encode information optically, based on the size, shape, position, color, absorptivity, reflectivity, and/or transmissivity of a particular portion or portions of the system.

The reference fiducials may be identified and read using any suitable mechanism, including the electrical device and/or optical device used in sample analysis.

Example 6

Measurement System Having Optical Measurement Aids

This example, illustrated in FIG. 8, describes an exemplary measurement system 230 having optical measurement aids, in accordance with aspects of the invention.

The measurement system includes a substrate 232, a plurality of fluid compartments 234*a,b*, a plurality of electrodes 236*a,b*, and a carrier plate 238, at least substantially as described above in Example 5. However, the system further includes an optical measurement aid for use in conjunction with a suitable optical analysis system, as described above. The optical measurement aid generally comprises any element or mechanism adapted to facilitate and/or enable optical analysis of samples such as cells or vesicles positioned on or near the substrate. The optical measurement aid may comprise a modification of one or more of the elements listed above and/or a new element in addition to and/or in lieu of one or more of the elements listed above.

The optical measurement aid may comprise a support element that includes a short spacer and/or a thin, optically transparent carrier plate, as described above. A short spacer and/or a thin carrier plate may shorten the optical path length between the optical device and sample, by reducing the separation between the substrate and carrier plate. A thin carrier plate also may better match the optical requirements of the optical analysis system. To this end, the thickness of the carrier plate may be selected to correspond to the thickness of a standard microscope cover slip, for example, 0.08 to 0.13 mm thick (No. 0), 0.13 to 0.17 mm thick (No. 1), 0.16 to 0.19 mm thick (No. 1½), or 0.17 to 0.25 mm thick (No. 2), among others. To related ends, the carrier plate may be selected to improve overall optical transmission, for example, by using crystal-clear, pure water-white glass or super clarity, clear-white borosilicate glass. Alternatively, or in addition, the carrier plate may be selected to improve transmission of polarized light, for example, by using strain-free glass or fused silica. Alternatively, or in addition, the carrier plate may be selected to have uniform surface quality, exceptional flatness, and/or precise dimensions, among others.

The optical measurement aid also may comprise a carrier plate or other interface having an array of lenses 240 such as microlenses that correspond in number and spacing to the array of measurement sites. These lenses may be formed from any suitable material (such as glass or plastic) using any suitable technique (such as etching or molding). The lenses may be used for high-magnification and/or high numerical aperture analysis of samples, including the analysis of single cells positioned on single apertures. To assist such analysis, the x-y resolution of the recording apertures and microlenses preferably is less than a few (e.g., about 1-4) µm, which may be facilitated using a high-precision bonding process. Moreover, the z resolution of these components preferably is less than a few (e.g., about 1-4) µm, which may be facilitated using lenses having high numerical apertures.

The lenses in the array generally may have any shape capable of collecting light from the sample and/or focusing light onto the sample. For example, the lenses may be plano-convex, meaning that they have a flat (piano) surface and an opposed outwardly bulging (convex) surface. The plano-convex lenses may have two orientations. In the first orientation, exemplified by lens 240, the convex surface 242 faces toward the sample site, and the planar surface 244 faces away from the sample site. In the second orientation, exemplified in FIG. 8 by lens 240', the convex surface 242' faces away from the sample site, and the planar surface 244' faces toward the sample site. In either orientation, the lens will collect light transmitted from the sample and direct the collected light toward a detector, such as an imaging detector (e.g., a charge-coupled device (CCD)) or a point detector (e.g., a photomultiplier tube (PMT)), among others.

The optical measurement aid also may include a window 246 in the substrate having a shape configured to match an optical sensed volume, including the frustoconical shape through which excitation light is directed onto the sample and/or from which emission light is detected from the sample, for example, as described in U.S. patent application Ser. No: 09/478,819, filed Jan. 5, 2000 (now U.S. Pat. No. 6,488,892), which is incorporated herein by reference in its entirety for all purposes. The matching may be used in optical analysis to increase sensitivity (for example, by avoiding detection from walls of the sample well) and/or to decrease sample volume, among others.

Example 7

Analysis System

Figure 9:
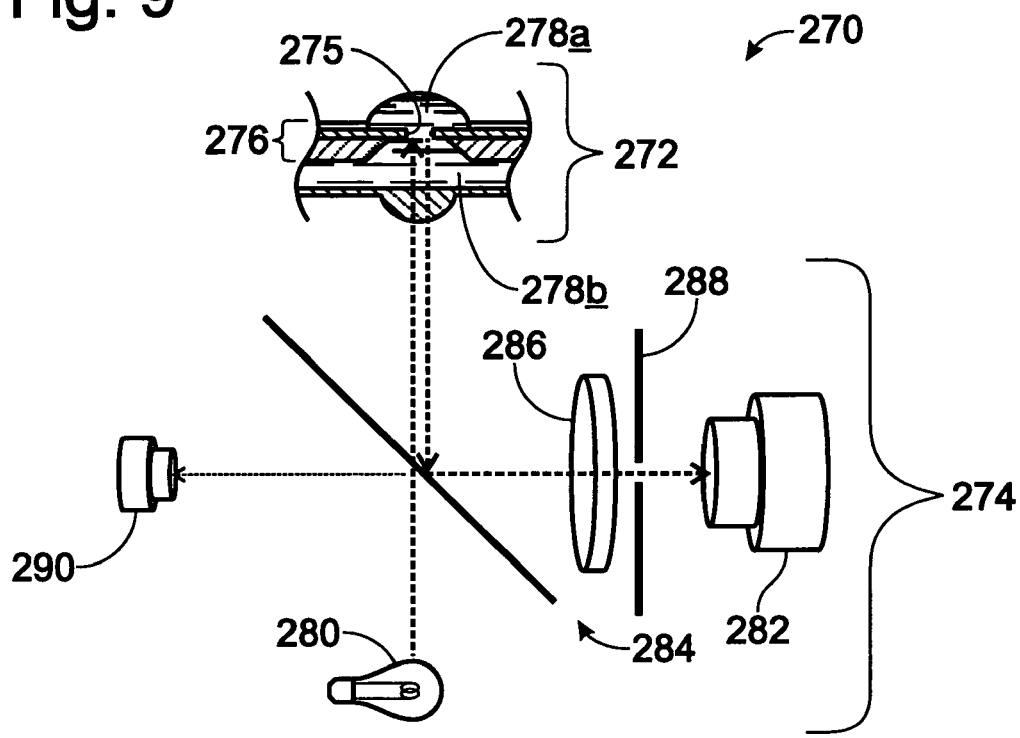
FIG. 9 is a partially cross-sectional partially schematic side view of a measurement system for combined electrical/optical detection.

This example, illustrated in FIG. 9, describes an exemplary measurement system 270 for combined electrical/optical detection, in accordance with aspects of the invention.

The combined measurement system includes an electrical analysis system 272 and an optical analysis system 274.

The electrical analysis system generally comprises any system for performing electrical measurements such as patch clamp measurements on a sample such as a cell, vesicle, or biological organelle. The electrical analysis system may include any suitable combination of apertures 275, substrates 276, fluid compartments 278a,b, and electrodes (not visible in this view), among other elements, as described above. Exemplary systems are described above in Examples 2-6.

The optical analysis system generally comprises any system for detecting light transmitted from the sample, particularly photoluminescence and chemiluminescence light. The optical analysis system may include a light source 280, a detector 282, and an optical relay structure 284 for transmitting excitation light from the light source to the sample and emission light from the sample to the detector. The system further may include additional components for performing additional and/or duplicative functions, including (1) filters 286 positioned in the excitation and/or emission optical paths for altering the intensity, wavelength, and/or polarization of the excitation and emission light, respectively, (2) confocal optics elements 288 such as an aperture positioned in an image plane for reducing detection of out-of-focus light, and (3) a reference monitor 290 positioned to detect a portion of the excitation light for correcting for variations (e.g., fluctuations and/or inhomogeneities) in the excitation light.

The light source generally comprises any mechanism for producing light suitable for use in an optical assay, such as a photoluminescence, scattering, and/or absorbance assay, among others. Suitable light sources include lasers, arc lamps, incandescent lamps, fluorescent lamps, electroluminescent devices, laser diodes, and light-emitting diodes (LEDs), among others. The light source may be capable of use in one or more illumination modes, including continuous and time-varying modes, among others.

The detector generally comprises any mechanism for detecting light transmitted from a sample in an optical assay. Suitable detectors include charge-coupled devices (CCDs), intensified charge-coupled devices (ICCDs), videcon tubes, photomultiplier tubes (PMTs), photodiodes, and avalanche photodiodes, among others. The detector may be capable of use in one or more detection modes, including (a) imaging and point-reading modes, (b) discrete (e.g., photon-counting) and analog (e.g., current-integration) modes, and (c) steady-state and time-resolved modes, among others.

The optical relay structure generally comprises any mechanism for transmitting light between the light source, sample, and detector (or simply the sample and detector in a chemiluminescence assay). Suitable optical relay structures may include mirrors, lenses, and/or fiber optics, among others. Here, the optical relay structure includes a beamsplitter that generally transmits excitation light toward the sample and generally reflects emission light toward the detector.

FIG. 9 shows an exemplary embodiment of a combined electrical/optical measurement system, including components as described above. Here, a parallel read-out system is used for confocal-optical recordings, for example, using the chip substrate system of FIG. 8. In either order, the chip substrate is placed in an appropriate light beam that is able to excite fluorescent probes of interest, and the sample membranes or cells are positioned at the individual apertures of the chip. The samples are excited using one parallel light beam, for example, using a 45-degree mirrored beamsplitter. The fluorescent light coming from the biological sample or any associated fluorescent probes is transmitted to an optional filter and confocal optics element to increase the signal-to-noise ratio before being projected onto the light sensitive chip of a CCD camera. The confocal optics element reduces or eliminates out-of-focus light not originating from the sample. The spatial resolution of the CCD chip allows detection of fluorescence from all apertures (and consequently all biological samples) simultaneously, if desired.

More generally, the system may be configured to allow top and/or bottom illumination and/or detection of the sample(s), permitting the following combinations: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and is preferred for absorbance assays.

Alternatively, or in addition, the system may be configured to allow illumination and/or detection at oblique angles. For example, illumination light may impinge on the bottom of a sample holder at an acute angle (e.g., about 45 degrees) relative to detection. In comparison with a straight-on epi system (light source and detector directed at about 90 degrees to sample holder) or a straight-through trans system (light source directed through sample holder directly at detector), an oblique system may reduce the amount of excitation light reaching the detector.

Suitable systems, and components thereof, for top/bottom and/or oblique illumination are described in the following materials, which are incorporated herein by reference in their entirety for all purposes: U.S. Pat. No. 5,355,215, issued Oct. 11, 1994; U.S. Pat. No. 6,097,025, issued Aug. 1, 2000; and U.S. Provisional Patent Application Ser. No. 60/267,639, filed Aug. 10, 2001.

Example 8

Producing, Sizings anid Binding of Vesicles

This example describes exemplary methods for producing, sizing, and binding lipid vesicles.

A mixture of 100 μL asolectin (Fluka) or egg lecithin (EPC), 50 μL palmitoyloleylphosphatidylglycerol (POPG), and 3 μL dipalmitoyl phosphatidyl-ethanolamine-rhodamine (DPPE-rhodamine) (Molecular Probes, USA) (all 10 mg/mL in chloroform, Avanti Polar Lipids), and 70 μL methanol is dried in a rotary vaporizer (Büchi Rotavapor R-114) at low (400 mm Hg) pressure in a 10 mL round flask to form a film. After a 1-hour incubation under vacuum, to the flask is added either 10 mL $H_2O$ or 10 mL of a buffer solution having a concentration of less than 150 mM of KCl and/or less than 600 mM of sucrose or preferably of sorbitol. After a subsequent 16-hour incubation at 37° C., the resulting lipid vesicles appear as an almost transparent cloud. The lipid vesicles are aspirated and removed using a 1 mL pipette and stored at 4° C. until further use. Storage of the vesicle solution may be improved by the addition of sodium azide ($NaN_3$) to a concentration of 0.2% by weight. This vesicle preparation procedure yields mostly (>90%) unilamellar vesicles, with sizes up to 250 μm. However, some of the vesicles may contain additional smaller vesicles, which are not relevant for membrane formation.

The ability of the resulting vesicles to establish electrically tight seals against a surface aperture is enhanced by purification of the initial vesicle mixture to remove vesicles and lipid impurities that are smaller than about 10 μm in size. Without such purification, the binding of such smaller vesicles in the vicinity of the aperture may prevent electrically tight sealing of the aperture by large (e.g., larger than 10 μm) vesicles. The vesicles may be sized by dialysis, for example, using a nylon mesh with a 20-μm pore size for at least about 20 hours. If necessary, the membrane fluidity of the resulting vesicles may be lowered, for example, by adjusting the lipid composition so that it includes a higher fraction of low-fluidity lipids and/or by lowering the temperature so that it is closer to the phase-transition temperature of the vesicles (e.g., less than or equal to about 4° C., or more preferably less than or equal to about 1° C., for some lipids). The unilamellarity of the resulting vesicle membranes may be demonstrated and/or verified using any suitable analytical technique, such as microscopic analysis using a confocal microscope.[xi]

More generally, vesicles maybe produced, sized, and bound using any suitable methods, For example, large unilamellar vesicles (giant unilamellar vesicles, GUVs) may be produced using the hydration method.[xii] Similarly, proteoliposomes may be produced using an appropriately modified hydration method.[xiii] Additional vesicles may be produced using the methods described in U.S. patent application Ser. No. 09/952,461, filed Sep. 14, 2001 (now abandoned).

Example 9

Electrophoretic Positioning of Vesicles

Figure 10:
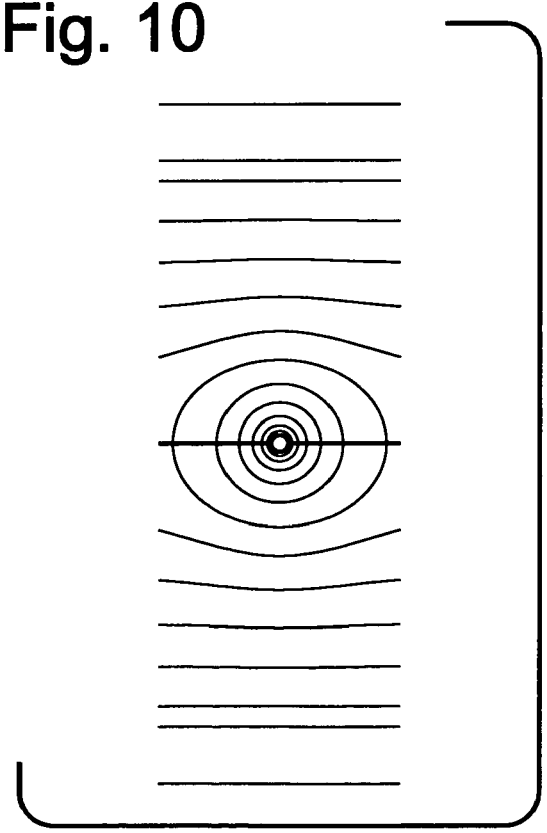
FIG. 10 is a contour plot of the electric potential adjacent an aperture in a substrate in accordance with aspects of the invention, computed by finite element method (FEM) simulation.

This example, illustrated in FIG. 10, describes exemplary methods for electrophoretically positioning samples such as cells and lipid vesicles. The positioning attainable using these methods may exceed that attainable using gravity sedimentation, in at least the following ways: (1) a decrease in the necessary number of vesicles or cells, (2) an increase in the total rate of membrane formation, and (3) an increase in the probability of a successful membrane setup or cell binding. Vesicles and cells also may be prepositioned prior to electrophoretic positioning to improve performance, for example, by introducing the vesicles or cells to the sample so that they are initially positioned above the aperture.

The electrophoretic positioning methods make use of inhomogeneities in the electric potential and associated electric field surrounding the aperture. FIG. 10 shows results of a finite element method (FEM) simulation of the electric potential distribution around a substrate in accordance with aspects of the invention. The substrate includes a 4-μm aperture positioned between parallel electrodes. The field distribution is shown as a series of equipotential lines (corresponding a cross-section through the three-dimensional equipotential surfaces), with a spacing of 4 mV, where the potential difference between the electrodes is 80 mV. The field-line curve is distorted in this simulation from its normal circular form to an elliptical form to reflect leak currents in the edge region of the carrier chips. The following parameters were used in the simulation: $C_{buffer}$=10 mM KCl, V=80 mV, $d_{aperture}$=4 μm, and spacing between the aperture and each electrode=1 mm.

The electric field associated with an electric potential is minus the spatial rate of change of the potential, i.e., $E=-\nabla V$. Thus, the electric field is perpendicular to the equipotential surfaces at all positions, pointing in the direction of decreasing potential. Moreover, the electric field is stronger where the equipotential surfaces are closer together, and weaker where these surfaces are farther apart. Consequently, from FIG. 10, the electric field points toward the aperture (on one side of the aperture), with a strength that increases with proximity to the aperture.

These electrophoretic positioning methods generally may be used in any system capable of creating and focusing an electric field through an aperture. In preferred systems, the electrodes used to create the field are positioned relatively close together, for example, within about 5-10 mm, reducing the voltage required to create an acceptable electric field. Specifically, the measurement and reference electrodes are located, one above and one below the substrate, at a distance of about 0.2 to 3 mm, preferably about 0.5-2 mm, and more preferably about 0.5 to 1 mm. The clamp voltage generated by these electrodes is not critical; however, it customarily lies in the range $V_c$=-300 to -300 mV, preferably lies in the range -60 to -100 mV, and more preferably lies in the range -60 to -80 mV. The associated electrophoretic-driving force directs vesicles and cells, following the electric field, toward the aperture. In particular, because the electric field is strongly inhomogeneous, increasing sharply in magnitude with proximity to the aperture, vesicles and cells move automatically toward the aperture. In particular, the fields are most effective near the aperture (e.g., within about 200 μm of the aperture), so that samples preferably are brought into this range by prepositioning or reach it convectively.

For this purpose, a hole (for example, d<1 mm) may be located in the measurement electrode with respect to the aperture.

The following subsections describe two alternative methods of electrophoretic positioning.

9A. Variation 1

The offset voltage $V_{offset}$ between the electrodes may be corrected before each measurement. To do so, 5 µL of buffer solution is added directly to the aperture, and the measurement electrode is brought to within about 1 mm from the substrate surface. After a liquid meniscus forms between the surface of the substrate and the electrode, the offset voltage and the capacitance of the system are adjusted to compensate.

A 10-µL dispersion of lipid vesicles subsequently is added to the upper side of the measurement electrode, where the vesicles can sediment through the circular opening located in the measurement electrode. Vesicles that move through the measurement electrode opening may be accelerated directly to the aperture opening under the influence of an electric field generated by the applied electrode voltage, $V_M$=−50 to −80 mV. In doing so, the focusing achieved, measured in the number of vesicles passing through the aperture opening with unmodified surfaces, is a function of the size of the window (that is, the portion of the $SiO_2$ layer laid open by etching). Smaller $SiO_2$ windows (e.g., less than about 45×45 µm$^2$) clearly increase vesicle throughput.

9B. Variation 2

The offset voltage $V_{offset}$ between the electrodes may be corrected before each measurement. To do so, 5 µL of buffer solution is added between the substrate and the measurement electrode, or alternatively between the substrate and the reference electrode, after which the voltage is determined at which the current flow vanishes, satisfying the expression $I(V_{offset})=0$.

A 3-µL dispersion of lipid vesicles subsequently is added to the measurement compartment near the aperture, where, in the case of a plane parallel electrode arrangement, the vesicles can sediment through the circular opening located in the measurement electrode. Vesicles that come into the vicinity (e.g., less than about 200 µm) of the aperture experience a very high field intensity (generally but not necessarily between about 100 kV/m and several kV/m) and are accelerated according to the electric field curve directly to the aperture. After the vesicles bind to the substrate and form an electrically tight seal, they are analyzed electrically.

Example 10

Sealing of Vesicles with Unmodified Surfaces

Figure 11:
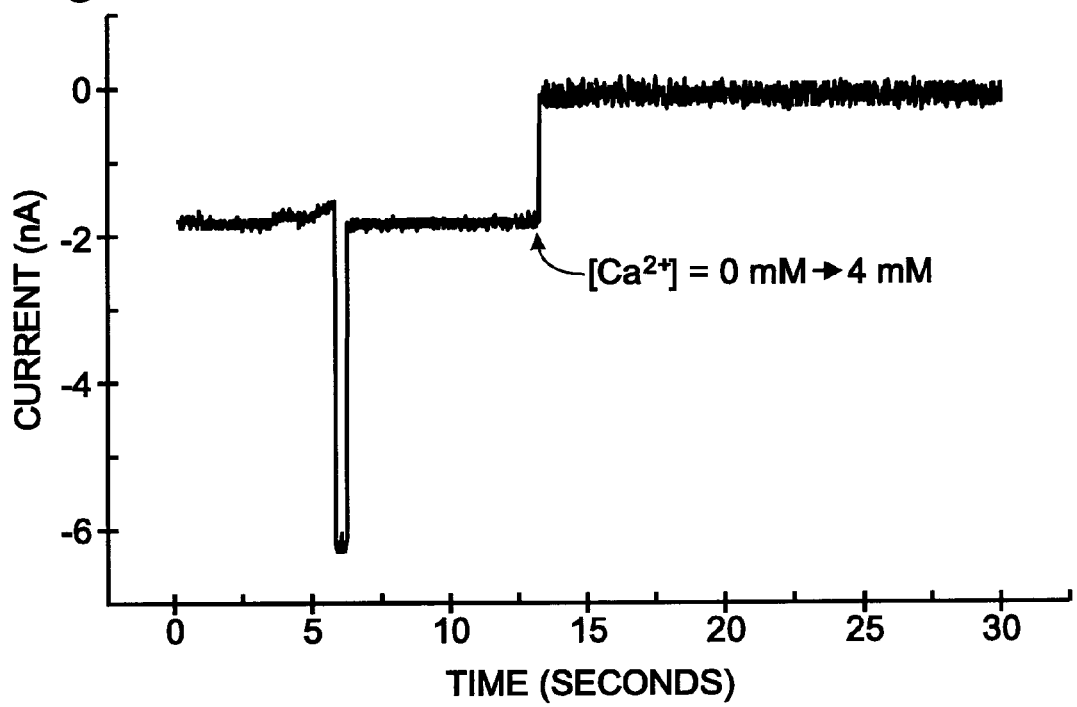
FIG. 11 is a plot of current versus time showing a decrease in current upon addition of $Ca^{2+}$ to a final concentration of 4 mM following the docking of vesicles at a 7-µm aperture in the unmodified surface of a suitable substrate.

The example, illustrated in FIG. 11, describes the sealing of vesicles, as described above, with unmodified surfaces. In particular, FIG. 11 shows a plot of current versus time after the docking or binding of vesicles to a 7-µm aperture in the unmodified surface of a suitable substrate. The plot shows that the addition of $Ca^{2+}$ to a final concentration of 4 mM leads quickly to a tight electrical seal between the vesicle membrane and the substrate surface. Specifically, the addition of $Ca^{2+}$ causes a rapid, significant drop in current, indicating that the membrane has at least substantially blocked ion pathways through the aperture.

Example 11

Binding and Adsorption of Vesicles on Modified $SiO_2$ Surfaces

Figure 12A:
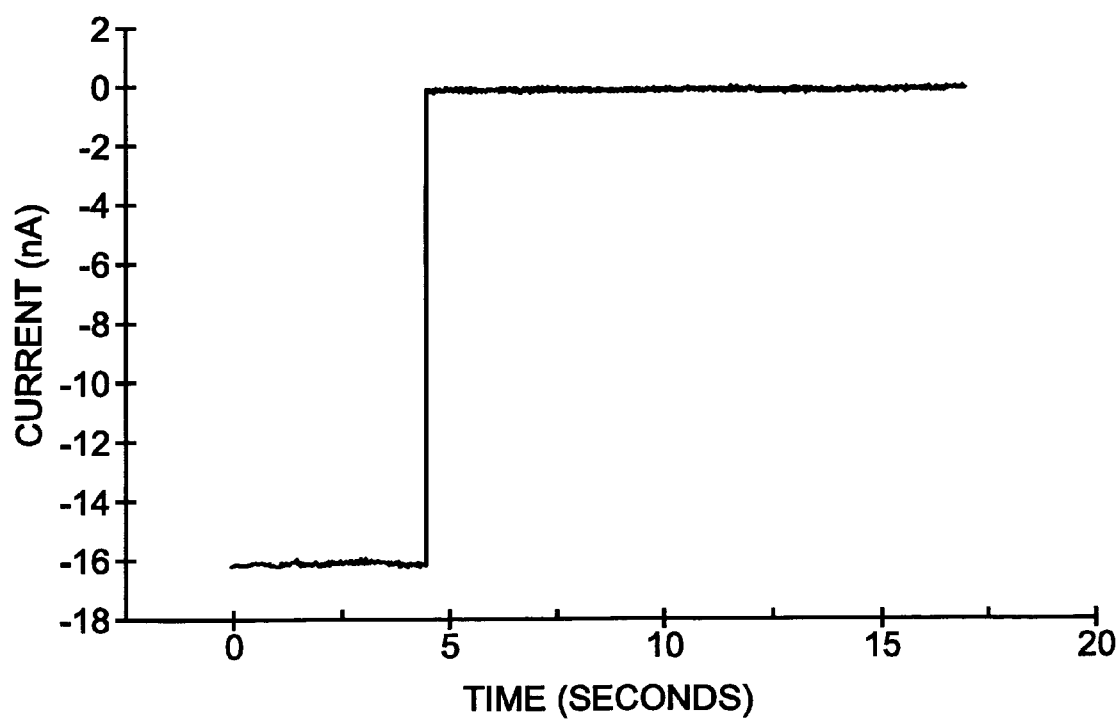
FIG. 12AB is a pair of plots of current versus time showing the time course of vesicle binding and the subsequent development of membranes with very high electrical insulation resistance for (A) a 4-µm aperture and (B) a 7-µm aperture in a poly-L-lysine-coated SiO$_2$ substrate.

The example, illustrated in FIG. 12AB, describes the binding and/or other interactions of vesicles as described above with polylysine-modified $SiO_2$ surfaces.

The binding between these vesicles and surfaces may be strong and rapid, manifesting itself in less than about 0.5 seconds after an appropriate proximity is reached. The probability of successfully positioning a vesicle and subsequently forming an electrically tight membrane seal is strongly dependent on the size of the aperture, the size of the $SiO_2$ window, and the number, size, and size distribution of the vesicles in the vesicle solution. If substrates having aperture diameters less than about 2 µm and window sizes greater than about 40 µm are used in conjunction with suspensions of vesicles having a vesicle diameter greater than about 40 µm, the probability of binding and forming an electrically tight seal may exceed 90% (n>15, where n is the number of trials). In general, a decrease in the width of the aperture and an increase in the purity of the vesicle suspensions lead to greater reproducibility in the formation of tight aperture seals, both substrate to substrate and vesicle preparation to vesicle preparation.

Vesicles that bind to the surface subsequently may be drawn out to form substantially flat, defect-free membranes. Fluorescence microscopy studies performed using vesicles labeled with both rhodamine (to label vesicle membranes) and carboxyfluorescein (to label vesicle interiors) show that vesicles flatten and may burst upon binding, forming unilamellar structures, since bound vesicles appear flat and red, suggesting that carboxyfluorescein has been released. These studies were conducted using polylysine-coated glass and a confocal microscope (LSM 510, Zeiss Jena, Germany). Electrical studies of membrane resistance, $R_M$, demonstrate that the bound vesicles may form substantially defect-free lipid membranes, since very high membrane resistances (e.g., $R_M$>6.4 GΩ (n=26)) are measured on the substrates in symmetric 85 mM KCl. An analogous series of measurements in symmetric 10 mM KCl demonstrates binding of the vesicles, after appropriate proximity, in less than about 0.2 seconds, with a probability greater than about 70% (n>15) and a membrane resistance greater than about 10 GΩ.

To promote strong adhesion of the vesicles, the surface of the substrate, in given cases, is coated with an adhesion promoter, for example, polycations.[xiv] For physiorption, for example, an aqueous solution of polycations (e.g., 0.1% poly-l-lysine bromide, MW 100,000, Sigma) may be added to the substrate for about 2-5 minutes directly before the measurement and subsequently rinsed off with measurement buffer solution. The covalent binding of peptide polycations preferably is done using previously activated hydroxyl groups of the quartz surface, for example by means of tosyl chloride (triphenylchloromethane).[xv] Through the modification of the substrate surface, an attraction of vesicles with negative surface charge is achieved, which is completely sufficient for electrically tight seals between the membrane and the substrate surface. Alternatively, the surface also may be modified by other compounds having cation characteristics in the desired pH range, such as, for example, 4-aminobutyl-dimethyl-methoxysilane. Finally, treating the substrates in $O_2$ plasma for several minutes before surface modification leads to more consistent surface characteristics.

Figure 12B:
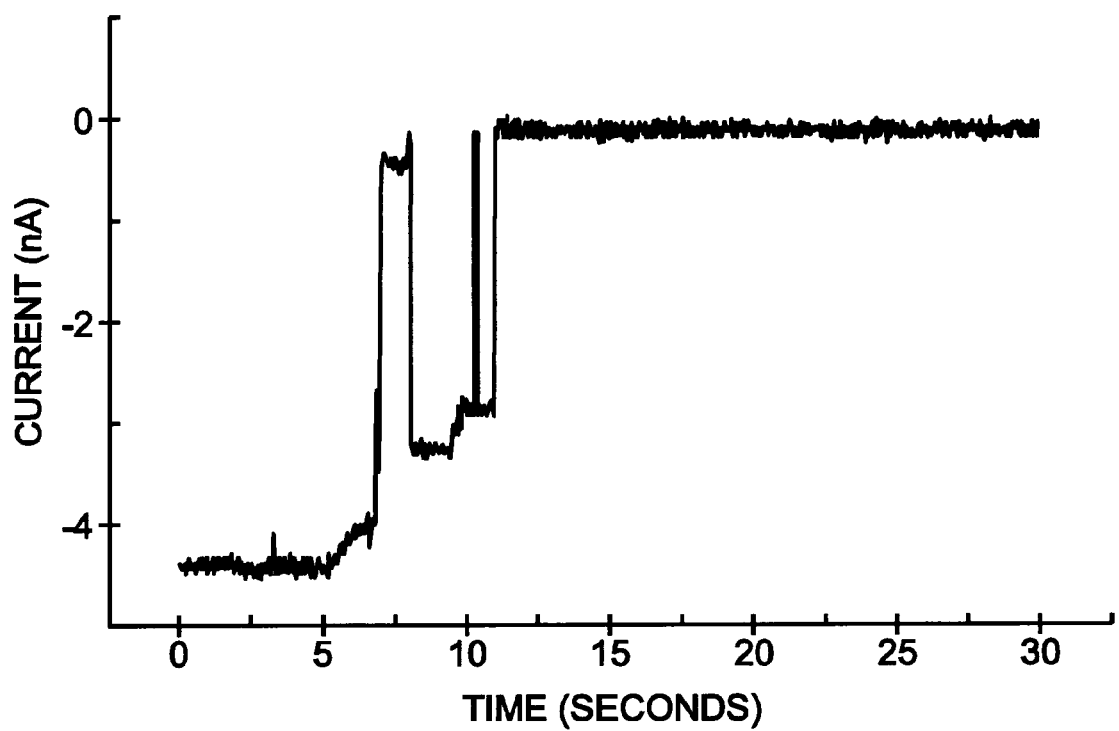

FIG. 12AB shows the time course of vesicle binding and the subsequent development of membranes with very high electrical insulation resistance for a 4-μm aperture (FIG. 12A) and a 7-μm aperture (FIG. 12B) in a poly-L-lysine-coated $SiO_2$ substrate. The measurements were performed in the presence of 10 μM KCl, using a clamp voltage of −80 mV.

Example 12

Membrane Electrical Properties

This example describes electrical factors relating to preferred aperture sizes, including characteristic electrical properties.

The thermal noise σ of a circular lipid membrane is proportional to $R_M^{-1/2}$:[xvi]

$$\sigma = \sqrt{\frac{4kTf_c}{R_M}}$$

where $R_M = R_{spec}/(\pi r_M^2)$. It follows therefrom that $$\sigma = r_M \sqrt{\frac{4\pi kTf_c}{R_{spec}}}$$

In these formulae, σ is the effective noise flow, r is the radius, f is the frequency, k is the Boltzmann constant, R is the resistance, and T is the temperature.

Thus, to be a usable membrane for measurement purposes, $r_M/\sqrt{R_{spec}}$ should be very small. The minimization of this product can be pursued according to the invention in two ways: (1) by minimizing the membrane radius $r_M$, and/or (2) by the electrically tight sealing of the membranes used.

Example 13

Electrical Parameters of Lipid Membranes

This example describes the effects of vesicle fusion on electrical parameters of the measurement system, as described above.

The resistance across the sample substrate changed significantly following vesicle fusion. Before fusion, the resistance is up to 1 MΩ (usually <450 kΩ) in 85 mM KCl, and similarly usually up to 1 MΩ in 1 mM KCl, depending in both cases on the size of the aperture. Greater resistances are interpreted as artifacts, possibly reflecting, for example, the inclusion of air bubbles under the aperture opening. After fusion, the resistance is greater than about 6.4 GΩ in 85 mM KCl, greater than about 10 GΩ in 10 mM KCl, and greater than about 40 GΩ in 1 mM KCl, corresponding to four order-of-magnitude increases in resistance. Here, the resistance R is at least approximately related to the applied voltage V and the current I according to Ohm's law, i.e., R=V/I.

The capacitance of the sample substrate changed only insignificantly following fusion, by several pF in 85 mM KCl, and by 160 to 280 pF in 1-10 mM KCl.

Example 14

Vesicle Passage through Micrometer Pores

Figure 13:
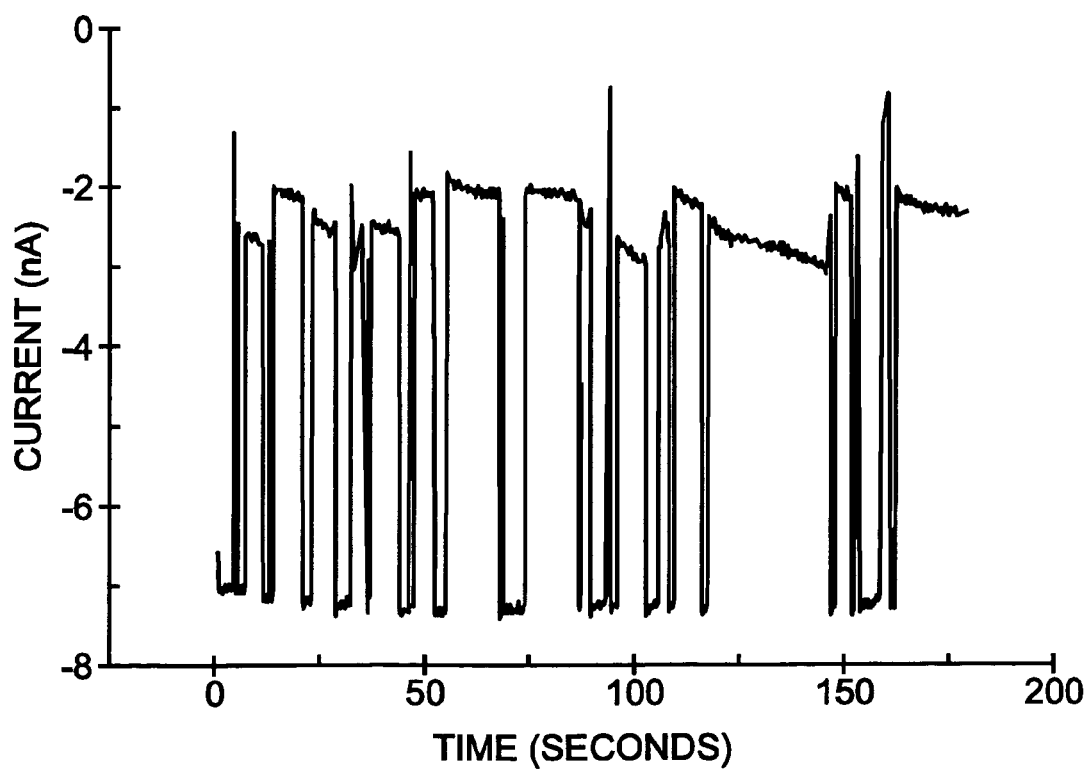
FIG. 13 is a plot of current versus time showing the passage of individual vesicles through a 7-µm aperture, as reflected in fluctuations in the plot recorded at a constant clamp voltage, $V_c$, of −80 mV.

This example, illustrated in FIG. 13, describes the passage of vesicles through apertures in the substrate.

The passage of vesicles through an aperture in the presence of negatively charged surfaces, such as unmodified $SiO_2$ layers, can be observed by monitoring changes in current (or, equivalently, resistance) across the aperture. Specifically, the passage of vesicles will lead to a decrease in current and an associated increase in resistance. To monitor for artifacts in the observed values, the polarity of the voltage is reversed, whereupon no modulation of current or resistance is observed.

The duration of observed changes in the amplitude of resistance can be correlated with size of the vesicles passing through the aperture being monitored. For example, modulations in the amplitude of resistance lasting up to 18 seconds suggest the passage of very large vesicles with sufficiently fluid membranes. Where vesicle populations with diameters greater than about 50 μm (n=4) are used in conjunction with aperture openings with diameters of about 7 μm, an almost exclusive variation of the time of passage for fixed changes in amplitude as a function of vesicle size is observed. It is presumed that vesicles undergoing passage through the aperture opening are drawn out during their passage to form tubular structures with definite diameters and closed surfaces.

By analyzing the typical time of passage for large vesicles ($d_{vesicle} \gg d_{aperture}$) and the typical change in the amplitude of resistance for small vesicles ($d_{vesicle} \sim d_{aperture}$), the composition of the vesicles with respect to size can be determined for a given vesicle solution. The method of the invention therefore possesses utility for analyzing size distributions in selected populations of vesicles and cells.

Example 15

Observation of Alamethicin Pores and Nicotinic Acetylcholine Receptors

Figure 14:
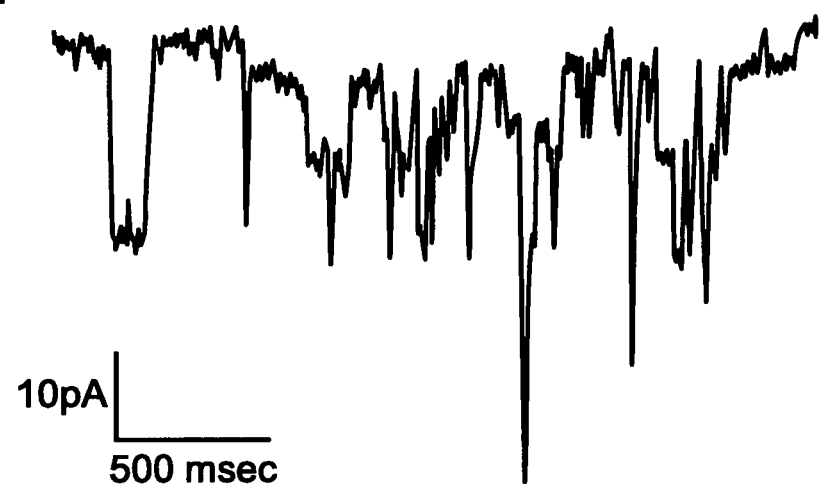
FIG. 14 is a plot of current versus time showing the time- and voltage-dependent switching of alamethicin pores in a membrane produced on the substrate ($C_{alamethicin}$=0.1 µg/mL in 85 mM KCl) at negative potentials.
Figure 15A:
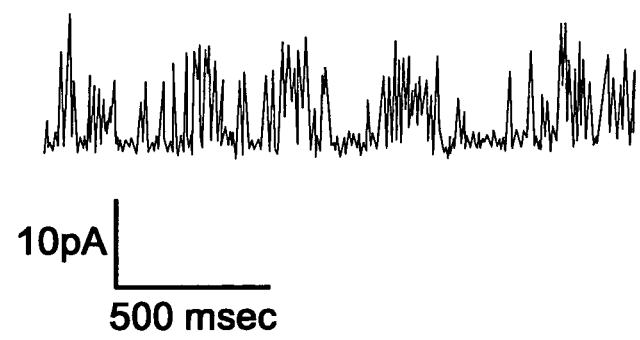
FIG. 15AB is a pair of plots of current versus time showing the changes in measured membrane resistance of a membrane produced on a Si/SiO$_2$ carrier chip after fusion with vesicles containing nAChR (nicotinic acetylcholine receptor).

This example, illustrated in FIGS. 14 and 15AB, describes observation of electrical activity of alamethicin pores and nicotinic acetylcholine receptors (nAChR) in fused vesicles. These observations confirm the biological utility of the invention.

FIG. 14 shows a plot of current versus time for membranes containing alamethicin. In these experiments, a membrane is formed over an aperture in 85 mM KCl. Next, alamethicin is added to the measurement compartment, to a final concentration of 0.1 μg/mL.[xvii] Finally, a potential is applied, and a plot of current versus time is generated. The amplitude and dwell times of the current fluctuations observed in this plot, corresponding to 600 pS conductivities of the alamethicin pores, prove the functionality and high sensitivity of the system.

Figure 15B:
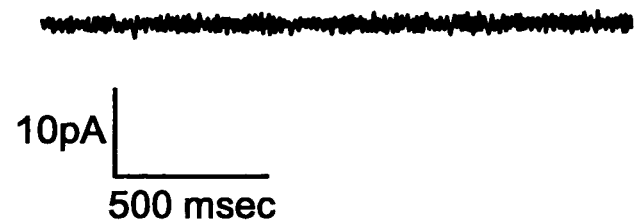
FIG. 15B shows the membrane resistance 150 seconds after the addition of the nAChR agonist carbamylcholine (20 µm final concentration), where no receptor openings are observed due to desensitization of the receptors.

FIG. 15AB shows an analogous plot of current versus time for membranes containing the membrane protein nAChR. In these experiments, a membrane is formed as above. Next, nAChR is introduced into the membrane via $Ca^{2+}$-mediated fusion. Specifically, nAChR is purified from an appropriate source, and then reconstituted into small unilamellar vesicles.[xviii] Next, these vesicles are added to the measurement compartment, and then fused to the membrane by increasing the $Ca^{2+}$ concentration of the sample chamber to greater than about 1 mM. In given cases, the fusion is supported by the subsequent temporary setup of an osmotic gradient.[xix] Finally, a potential is applied, and a plot of current versus time is generated. In the absence of agonists, typical receptor opening events are observed (FIG. 15A), whereas, in the presence of agonists, such as carbamylcholine (20 μM final concentration), such receptor opening events are substantially extinguished within a short time (t<100 seconds) (FIG. 15B).

Example 16

Analysis of Cells

This example, illustrated in FIGS. 16-18AB, describes use of the above-described systems in the study of cells.

The methods of the invention are generally applicable to the investigation and analysis of cells. Such cells may be positioned and electrically characterized using procedures substantially analogous to those described above for vesicles. However, in some cases, the positioning and measurement methods may be modified as desired to accommodate differences in vesicles and cells, including, among others, the cytoskeleton, the varied lipid and protein content of cell membranes, and the cell wall in plants and certain algae, bacteria, and fungi. For example, the cell may be made more flexible by disrupting the cytoskeleton, for example, using cytochalasin and/or colchicine. Similarly, in measurements using plant cells, the cell wall may be removed to expose a relatively smooth membrane surface capable of forming a tighter electrical seal. Similarly, in measurements using animal cells derived from tissues, the extracellular matrix may be removed or digested, for example, using one or more proteases, lipases, and/or glycosidases, among others.

The methods may be used for a variety of patch clamp experiments, in a variety of formats or configurations. The cell, as initially bound and sealed, is in a "cell-attached configuration." If the membrane patch over the aperture then is ruptured or destroyed, for example, by applying a pulse of voltage or suction, electrical measurements can be performed over the entire cell membrane in a "whole-cell configuration." Alternatively, if the membrane patch over the aperture is permeabilized, for example, by the addition of pore formers such as amphotericin B or nystatin to the reference compartment, electrical measurements again may be performed over the entire cell membrane in a "perforated-patch configuration." Alternatively, if the cell (instead of the membrane patch over the aperture) is lysed, electrical properties of the patch may be measured in an "inside-out configuration." In the lattermost approach, the cytosolic side of the membrane is exposed to the measurement solution, and the relatively small area of membrane being analyzed potentially makes possible the study of individual channel events.

Figure 16:
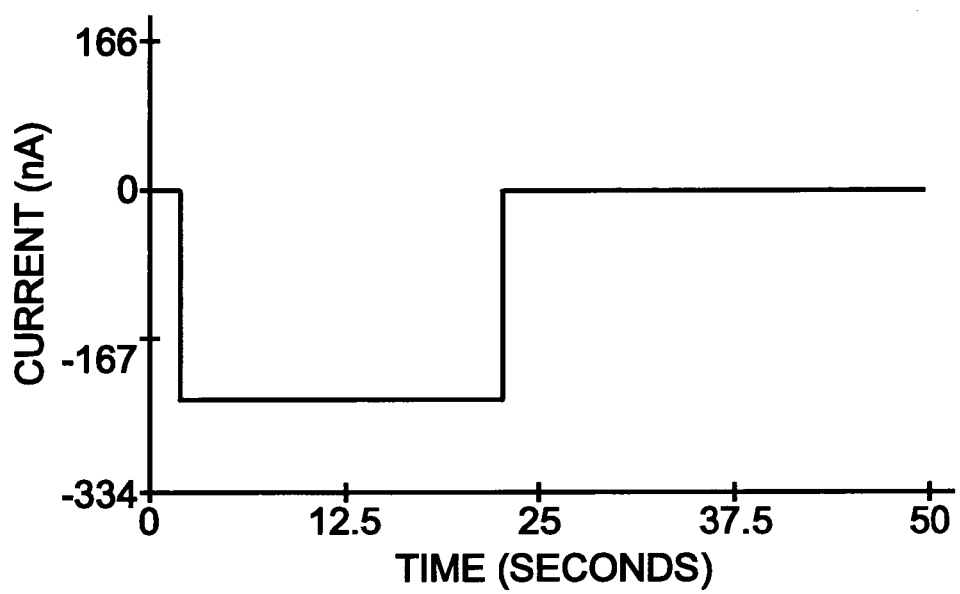
FIG. 16 is a plot of current versus time showing the time course of positioning, binding, and subsequent development of a tight electrical seal for a Jurkat cell.
Figure 17:
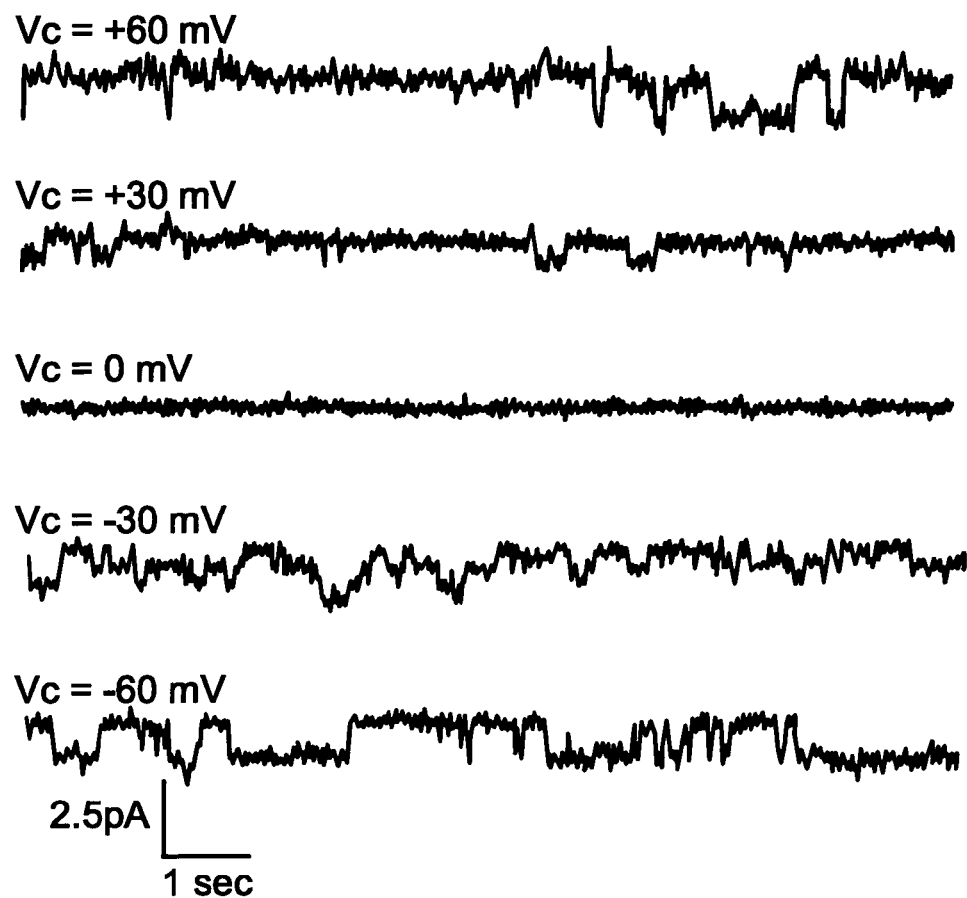
FIG. 17 is a series of plots of current versus time showing the current flowing through the membrane of a Jurkat cell for the indicated positive and negative clamp voltages.
Figure 18A:
FIG. 18 is an analysis of the current flowing through the membrane of a Jurkat cell for a +60 mV clamp voltage showing (A) a representative plot of current versus time, and (B) a histogram showing the relative likelihood of the measured currents.
Figure 18B:
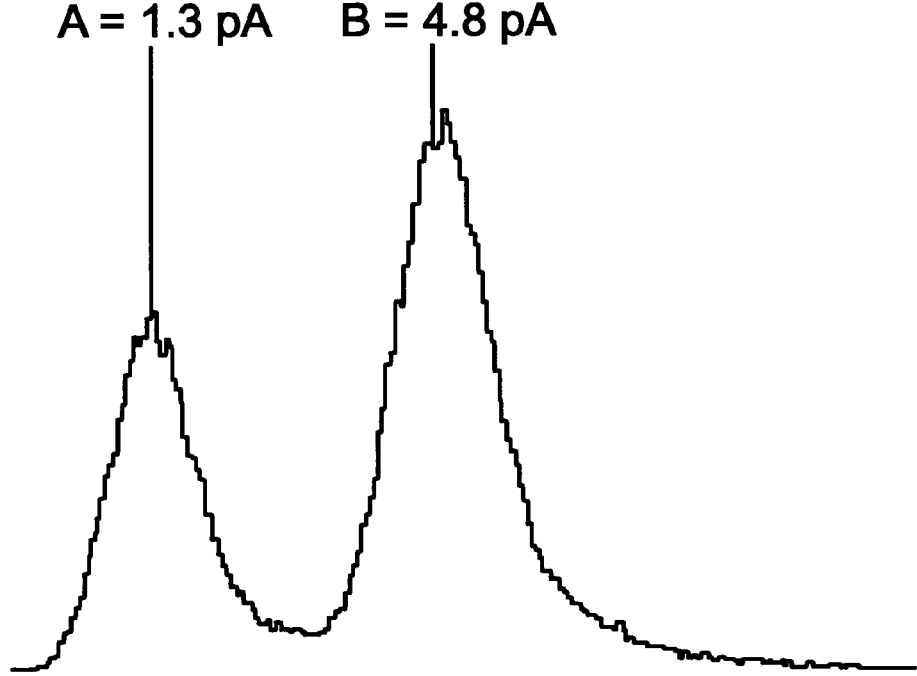

FIGS. 16-18 show exemplary results of positioning and voltage clamp experiments performed using Jurkat cells. These cells, a human mature leukemic cell line, phenotypically resemble resting human T lymphocytes and are widely used to study T cell physiology. Similar results (not shown) were obtained using TE 671 cells and CHO cells.

The cells were cultured and prepared using standard cell culture techniques. These cells were maintained for 2-5 days at 37° C. in 5% CO2 in RPMI with Glutamax, supplemented with 10% FCS and P/S (100U/100 μg/mL). Before use, cells were resuspended in a physiological buffer (PB=NaCl, 140 mM; HEPES, 10 mM; KCl, 5 mM; $CaCl_2$, 2 mM; $MgCl_2$, 1.2 mM; pH 7.3, osmolarity 290 mOsm) at a density of $10^7$ cells/mL. Lower and upper fluid compartments were filled with 20 μL and 15 μL of PB, respectively. Five μL of the cell suspension was added to the upper compartment. Positioning was made at $V_m$=−60 or −90 mV. All experiments were performed at room temperature.

FIG. 16 shows the time course of positioning, binding, and subsequent development of a tight electrical seal for a Jurkat cell. The cell was positioned at −60 mV. Seal formation occurred about 15 seconds after cell addition, quickly rising to about 1000 GΩ. The aperture size was about 3 μm, and the chip resistance was about 250 kΩ.

FIG. 17 shows a series of plots of current versus time showing the current flowing through the membrane of a Jurkat cell at the indicated positive and negative clamp voltages in a cell-attached configuration. The curves appear quantized, switching largely between just two values, one low and one high, particularly at higher voltages. This characteristic suggests that single-channel events are being observed, corresponding to the opening and closing of the channel.

FIG. 18 shows an analysis of the current flowing through the membrane of a Jurkat cell for a +60 mV clamp voltage. Panel A shows a representative plot of current versus time. This plot again has a quantized character, like FIG. 17. Panel B shows a histogram plotting the relative occurrence of a given current versus the current. The histogram is bimodal, with peak values of about 1.3 pA (the relatively smaller peak at left) and about 4.8 pA (the relatively larger peak at right), corresponding to an average of about 3.5 pA.

Example 17

Positioning and/or Analysis Systems

This example describes exemplary systems, including apparatus and methods, for micropositioning and/or analyzing biological membranous samples, including biological cells, liposomes, and/or portions thereof These systems may involve a contact region such as a surface divided into one or more zones distinguished by their differential affinity for the sample and/or sample medium.

17A. Summary

The invention provides systems for micropositioning and/or analyzing biological membranous samples.

The systems may include an apparatus for precisely micropositioning a biological membranous object, including, for example, biological cells, liposomes, or portions thereof. The apparatus has a surface having first and second distinct zones. The first zone is repulsive against a liquid that is compatible with the objects to be positioned and in which the objects are immersed. The second zone is attractive to the liquid. The first zone normally circumscribes the second zone and is immediately adjacent to the second zone. The first zone controls the shape and location of the liquid in contact with the second zone. The second zone is small, typically having an area of less than about 500 μm², more typically having an area of less than about 200 μm², and somewhat more typically having an area of less than about 100 μm².

The systems also may include a method for precisely positioning a biological membranous object on the apparatus of the invention. In the practice of the method, the membranous object is first suspended in a small volume of a suitable compatible liquid. For example, a physiological buffer will typically be used. Generally, the volume of buffer is from about 5 to 200 nanoliters ("nl"). More typically, the volume of buffer is from about 10 to 100 nl.

The compatible liquid, having the biological membranous objects of interest suspended therein, is loaded onto the apparatus of the invention. The liquid is restricted to the second zone on the apparatus, and the object comes into contact with and adheres to the second zone within a short time because of the distinct repulsive properties of the first zone and attractive properties of the second zone. Thus, the membranous objects are positioned on the apparatus in contact with the second zone.

The apparatus and methods of the invention for positioning a membranous object are useful in the electrical and optical analyses of cells, cell membranes, membrane proteins, lipid bilayers, liposomes, and the like. The invention can be used, for example, to analyze biological cells or components by various techniques, including voltage clamping, voltage sensing, and impedance spectroscopy techniques. The method of this invention is simple and does not require the degree of skill normally required by conventional electrophysiological methods.

17B. Detailed Description

Figure 19:
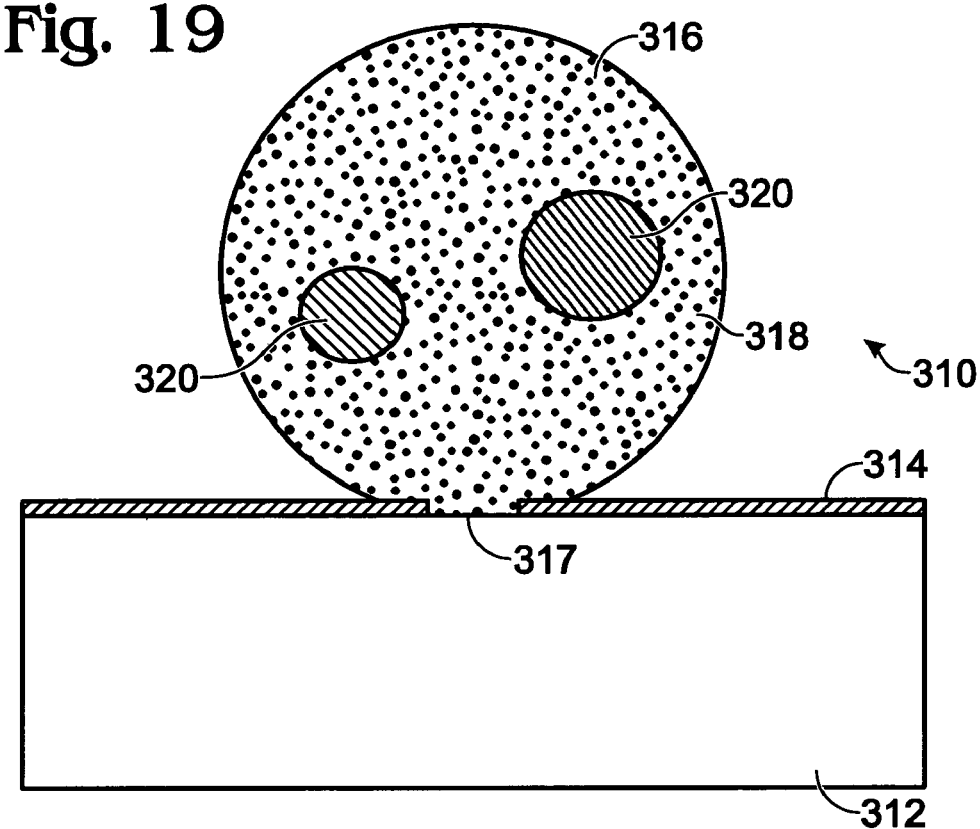
FIG. 19 illustrates one embodiment of the apparatus of this invention in a schematic sectional front planar view.

FIG. 19 is a schematic sectional diagram illustrating a front planar view of one embodiment of an apparatus 310 of the invention. Apparatus 310 comprises a body 312, the upper surface of which is covered by a hydrophobic material 314. An aqueous carrier fluid 316 for biological membranous objects contacts the body 312. Direct contact between the body and the fluid is possible only at the contact zone 317, which is not covered by the hydrophobic material. Hydrophobic material 314 constitutes a first zone, which is repulsive to the carrier fluid. The contact zone which is characterized by the absence of hydrophobic material, constitutes a second zone, which is attractive to the carrier fluid. Repulsion between the hydrophobic surface coat 314 of the first zone and the aqueous carrier fluid 316 creates a freestanding fluid compartment in contact with the contact zone 317 and defined by surface 318 and maintained by the surface tension that is characteristic of the fluid. Cells, liposomes, or other biological membranous objects 320 are contained within carrier fluid 316 within compartment 318. The objects drift into the contact or second zone 317 by sedimentation due to the shape and location of the fluid compartment above the second zone.

Figure 20:
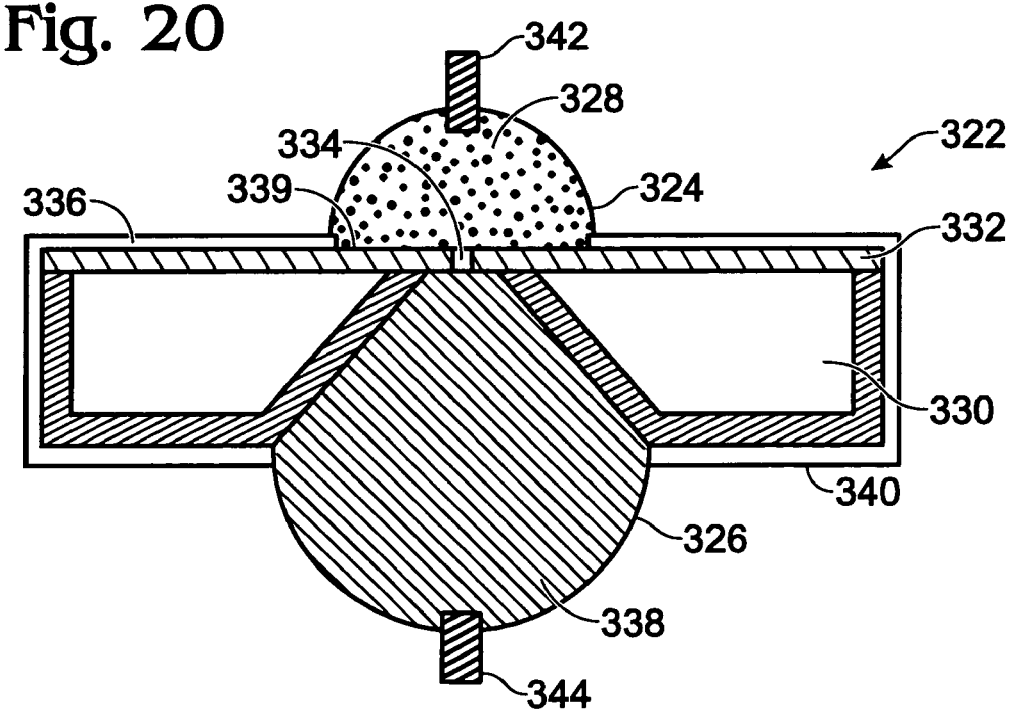
FIG. 20 illustrates another embodiment of the apparatus of this invention for obtaining electrical measurements on cells and liposomes or the like in a schematic sectional front planar view.

FIG. 20 is a schematic sectional front planar view of an apparatus 322 of the invention having two separate fluid compartments, 324 and 326, which can be the same or different fluids. The arrangement illustrated in FIG. 20 is especially useful for taking electrical measurements of biological objects, including cells or liposomes.

The carrier fluid 328 is contained in compartment 324. The body of the apparatus is a silicon chip that comprises a bulk silicon body 330 having an adherent insulating diaphragm 332 thereon that separates the two fluid compartments. An aperture in diaphragm 332 is shown at 334 between the two fluid compartments and provides electrical communication between the two compartments. The carrier fluid 328 in compartment 324 is restricted by a hydrophobic coat 336 over the insulating diaphragm 332 that is repulsive to the carrier fluid and defines the first zone. The fluid 338 in compartment 326 is also restricted by hydrophobic coat 336, further defining the first repulsive zone. Similar to the embodiment illustrated in FIG. 19, repulsion between the hydrophobic surface coat 336 and the aqueous carrier fluid of compartment 324 and between the hydrophobic surface coat 336 and the fluid of fluid compartment 326 creates freestanding fluid compartments 324 and 326, respectively, maintained by the surface tension that characterizes each fluid. The contact zone for the objects of interest is that surface area 339 that is in contact with the fluid 328 in compartment 324 and includes the aperture 334 and is limited by the repulsion zone defined by surface 336.

Compartment 324 contains the biological membranous particles or objects of interest. Vesicles, cells, or other membranous particles sedimenting in the contact zone of compartment 324 cover the aperture 334 to physically separate the two fluid compartments 324 and 326. The membranous object covering the aperture can be referred to as a "patch." Current passing between the two compartments flows through the portion of a biological membrane covering the aperture and defines the "membrane current." The membrane current can be used for analyzing membrane proteins, including ion channel proteins.

The potential difference driving the current is applied by electrodes 342 and 344 located opposite each other in the fluid compartments 324 and 326, respectively. If desired, an insulating layer 340 can be placed on the silicon body opposite the insulating diaphragm 332 to reduce or preclude capacitive noise and other artifacts of electrical measurement.

The apparatus of this invention can be used to carry or position any biological cells, artificial simulations of biological cells, liposomes, or portions thereof, including, for example, portions of cell membranes, protoplasts, and cell organelles. Cell organelles include, for example, mitochondria, chloroplasts, lipid bilayers, lipid micelles, and the like. The apparatus of this invention is useful for positioning many other cell-like materials including viral particles, mycoplasms, macromolecular complexes, and the like. The apparatus and method of this invention are especially useful for obtaining optical and electrical measurements on membranous objects.

The apparatus provides electrical and optical access to the cellular and liposomal membrane proteins of interest, when necessary, and also provides precise positioning of membranes on apparatus, which is important for taking optical and electrical measurements on membranes.

As illustrated in connection with FIGS. 19 and 20, the invention provides positioning of particles at a specific site or contact zone on a carrier by providing for adhesion of the particles only at the specific site. The space available for movement of the particles is confined to the close vicinity of the adhesion site by the geometry of the fluid compartment in which the particles are carried. The fluid compartment that contains the particles is confined to a particular geometry by the construction of the carrier and by the size of the carrier and the amount of fluid used so that the fluid stays in contact with the site.

The particles are immersed in fluid that is in contact with the part of the carrier surface containing the contact, zone. The particles are immersed in a fluid that is compatible with the particles and does not adversely affect the physical, chemical, and physiological state of the immersed particles. Normally, this fluid is a liquid and is a compatible aqueous solution. For example, a cell culture medium or a modified cell culture medium would be used for a biological cell. Other buffers and solutions useful for suspending, diluting, or storing the particles can typically be used. The fluid should not interfere with or adversely affect the attachment of the particle to the contact zone on the cell carrier. The fluid should not affect the analysis of the particles on the carrier, including electrical recording and optical analysis.

Normally, physiological buffers, including PBS, or Hank's buffer, and the like, will be useful.

In the embodiment of FIG. 20, two fluids are used, one as the carrier fluid 328 and one opposite the carrier fluid 338 for electrical transmission. These fluids can be the same or different, but the fluid 338 should be selected from the same group set forth above.

Precise positioning of particles on the carrier is achieved by providing, simultaneously, (1) surface patterns on the carrier that allow adhesion between the particle and the carrier only at the contact zone, but substantially precludes adhesion of particles outside the contact zone; (2) a defined fluid compartment in which the particles are immersed at the contact zone so that the movement of the particles is restricted to the vicinity of the contact zone, which normally is less than about 100 to 500 µm into the fluid compartment, depending on the particle size; and (3) directed motion of the particles towards the contact zone and random motion of the particles within the fluid compartment.

Directed motion is due to force fields, including gravitation, electrophoresis, and dielectrophoresis. Random motion is due to Brownian motion and convection. Together, these forces enable precise positioning within the fluid compartment after the compartment has been created at the contact zone.

A surface patterning that allows adhesion between the particle and the carrier only at the contact zone and precludes adhesion to all other places can be accomplished by creating the first zone repulsive surface and restricting the adhesive contact zone which is a portion of the apparatus main body 312 (FIG. 19) and 330 (FIG. 20) to a total area of from about 0.1 to 500 µm². Usually the total area of the contact zone will be from about 0.5 to 200 µm². Somewhat more typically, the total contact area will be from about 1 to 100 µm².

The defined, self-contained fluid compartment at the contact zone is created by adjacent attractive forces at the contact zone and repulsive forces outside the zone acting on the fluid. These forces may have different origins, including electrical charge interactions and hydrophilic/hydrophobic interactions. Physically or chemically patterned surfaces for the body of the apparatus are mainly hydrophobic surfaces that contain small hydrophilic contact zones within them. Various carrier materials can be used in the practice of the method of the invention, including, for example, $SiO_2$, Pyrex™, and various plastics in various geometries and sizes. Electrostatic interactions between these hydrophilic zones and the particles can occur that are particularly useful. For example, negatively charged giant liposomes can be attached to a positively charged planar surface contact zone of about 1 to 100 µm² prepared from $SiO_2$ modified with physisorbed poly-L-lysine and surrounded by a hydrophobic material, including, for example, Teflon® or $Si_3N_4$ Other hydrophobic materials, including the silanes in the case of $SiO_2$ and Pyrex™ carrier surfaces, and photosensitive coats allow the definition of contact zones by assembly and by photolithographic techniques, respectively. The specific geometries and combinations of materials useful in the practice of the invention are too numerous to mention and are believed to be well within the scope of the abilities of the skilled artisan once apprised of the examples of this disclosure.

Contact zones can be produced by partial activation of hydrophobic carrier surfaces. Surfaces can be activated by applying an oxygen plasma, high energy radiation, including UV radiation, or reactive chemical compounds, including $Cl_2$ and $Br_2$, to the surface area intended to be the contact zone. For example, an oxygen plasma can be applied to a PDMS carrier whose surface is covered by a mask that allows plasma access only at the contact zone. The same technique is also applicable to $SiO_2$ and similar carrier surfaces, which can be covered with, for example, silanes or polyaminoacids. If necessary, the activated surface can be further modified by physisorption or covalent attachment of functional groups that promote the binding of selected cells or vesicles, as is described further below.

For example, the contact zone can be made selective for certain types of cells or liposomes. The contact zone can be modified for specific interactions with the surface of the cells or liposomes. The contact zone can be coated with materials having binding affinity to the cell surface or liposome surface. Suitable materials can include, but are not limited to, biotin, avidin, laminin and the laminin receptor, integrin and integrin receptors, and the like. In general, interactions between a membrane receptor and a suitable ligand, or substrate in general, can be used for affinity binding. Thus, only cells or their organelles with specific properties are permanently positioned.

The contact zone can also be treated with antibodies and antigens in a similar manner so that certain objects are attached to the contact zone. For example, the second zone, which is the adhesion or contact zone, can be coated with antibodies that attach to certain specific molecules or structures on the cells or liposomes that it is desirable to position on the carrier.

The invention provides small fluid volumes that restrict the possible movement of the particles to allow positioning. For small fluid volumes of less than about 10 to 100 nl, the time required for cells or liposomes to enter the attractive range of the attractive contact zones for positioning becomes very small, and usually less then 5 minutes. The smaller the fluid volume in which the particles are suspended, the higher the chance to touch the contact zone or to enter the attractive range of this zone where charge interactions are operative. Also, the smaller the compartment size, the shorter the time required for positioning. For these reasons, the sample volumes in which the particles of interest are suspended should be as small as possible during the positioning process. Normally, the volume can be in the range from about 1 nanoliter to 500 nanoliters. Somewhat typically, the volume is from about 5 nl to 200 nl. Even more typically, the volume is from about 10 nl to 100 nl.

Other factors, including the rate of evaporation and the minimal buffer volume required for a specific cell to survive, may impose a compromise on the actual volume used. However, a very small fluid volume can be used for fast attachment of the particle to the specified contact zone and the fluid volume can be increased immediately thereafter. Using a two-step process in this manner may allow small volumes for positioning and short positioning intervals without impairing biological particles.

Another way of using very small volumes without the danger of evaporation of significant volume percentages is the employment of essentially inert and hydrophobic fluids overlaying the actual buffer volume. These fluids should be selected for a low dielectric constant and dissipation factor for sensitive electrical measurements. These fluids, an example of which is an alkane, including, for example, decane, can be added after the buffer fluid or before if adequate means are provided. A pipette can be used to dispense the buffer directly at the interface of the cell carrier surface and the inert fluid. Fluid injection can also be accomplished by InkJet technology and is believed to be within the purview of the skilled artisan once apprised of this disclosure.

After positioning onto a carrier of defined geometry, the exact location of the membranous object attached to the carrier is the place of the contact zone and is thus predetermined. The predetermined location of the membranous object provides the basis for constructing optical apparatus, and, in particular, confocal optical apparatus, for observation of the membranous objects. For example, cell membranes can be observed with high numerical aperture objectives after positioning the cells on a thin planar and transparent carrier, including glass. Examples of optical methods suited for such a use include fluorescence correlation spectroscopy (FCS), single molecule detection, and simple fluorescence observation of the cytosol. The latter does not require high numerical aperture objectives because of the three-dimensional size of the cytosol and the freedom to place the confocal spot within the cytosol. The cytosol can be loaded with fluorescent dyes that serve as probes for various cellular parameters, including free calcium concentration and membrane potential.

Optical and electrical analysis methods can be combined in one single set-up enabling electrical and optical measurements on particles to be performed simultaneously on membranous objects positioned in accordance with the invention. Thus, new insights can be obtained into the molecular behavior of single molecules. As an example, the embodiment of FIG. 20 may include a fully flat insulating diaphragm 332 onto which the membranous object of interest is positioned. The diaphragm may also serve as the carrier described in connection with confocal optical techniques and then subsequently provide for the concurrent optical and electrical analysis of the patch, or membranous object, covering the diaphragm aperture.

The size of the various set-ups and the combined opto-electrical set-up described above can be very small, less then 1 mm×1 mm×1 mm. The small size can be achieved due to the small size of the fluid compartments and carrier structures. This miniaturization makes it possible to build miniaturized biosensors and to integrate multiple set-ups into one single device, or to use one single carrier for multiple set-ups, as required for HTS.

Figure 21:
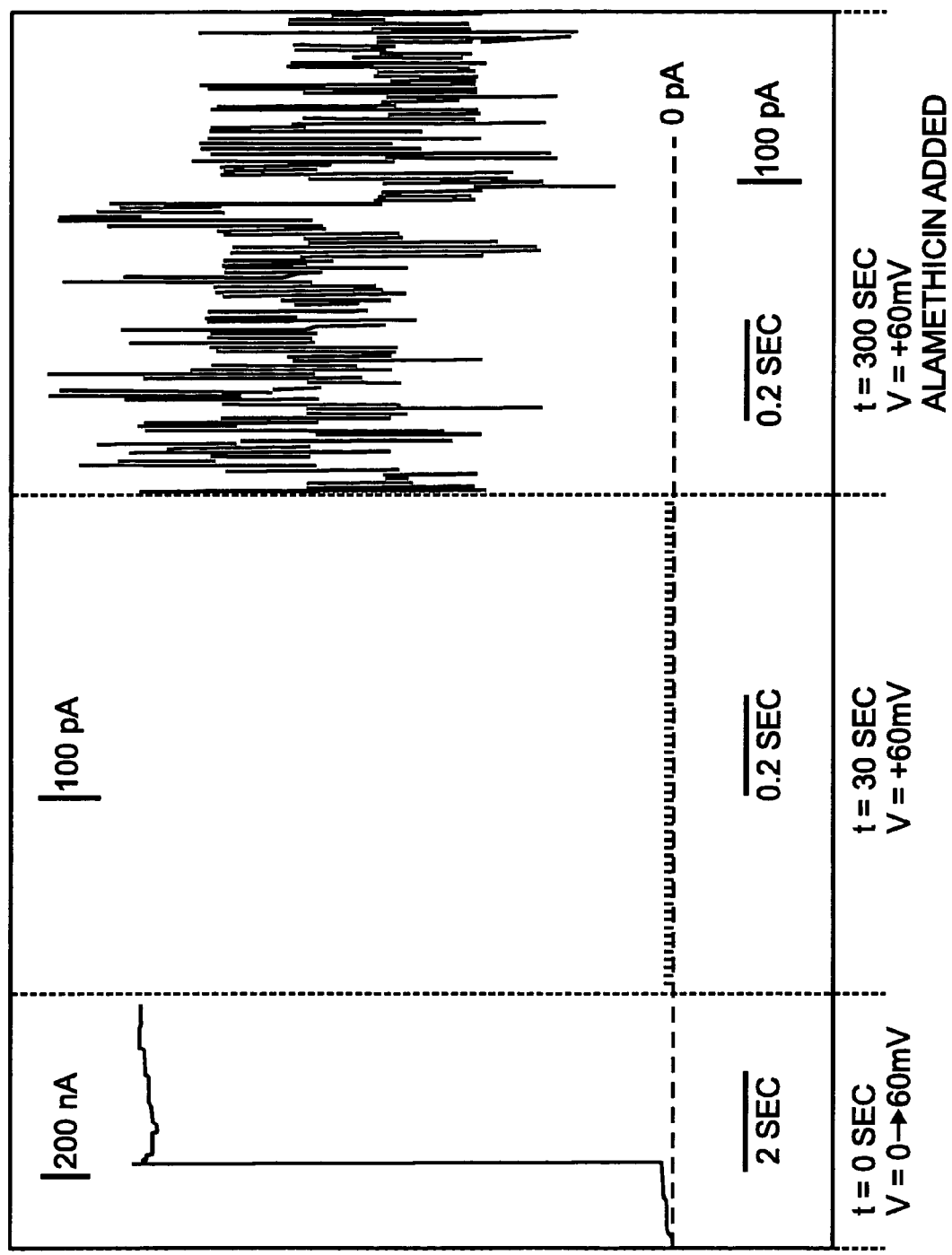
FIG. 21 is a voltage-clamp recording taken from membranous objects positioned on a specific embodiment of the apparatus illustrated in FIG. 20 and is a record of current at three different times taken over the time period indicated and at the voltage indicated.

FIG. 21 shows a voltage-clamp recording for a more specific embodiment of the cell carrier as illustrated in FIG. 20. The carrier can be fully or partly insulating and separate two fluid compartments as illustrated in and described above in connection with FIG. 20. The fluid compartments can be electrically connected by a small fluid passage through the carrier such as aperture 334 in the contact zone. The apparatus can be fully covered by positioning of a membranous object over the aperture in the contact zone. After positioning and electrically tight binding of the object over the passage, a voltage is applied between the two compartments via electrodes, and the resulting current is analyzed. Electrically tight binding means that complete coverage of the aperture is achieved. The current that results thus represents the actual membrane current mediated by transmembrane proteins and the leak currents flowing between the membrane and carrier body. A tight bond between surface and particle, referred to as a tight seal, reduces the leak current and allows sensitive current measurements. Tight seals of greater than $10^9$ Ohm can be achieved that allow low noise analysis of single ion channel proteins.

The membrane currents can be measured as follows for an electrically insulating carrier that separates the two fluid compartments and has a small aperture of diameter of from about 0.1 to 10 μm within the contact area that connects the fluid compartments. A voltage is applied across the liposome or cell or their respective membranes that covers the aperture by immersing electrodes such as redox electrodes into the fluid compartments. The current, which flows between the two conductive fluid compartments, is mainly determined by the resistance of the membrane patch covering the aperture, or by rupturing the patch by the resistance of the entire membrane.

A micromachined silicon $Si/Si_3N_4SiO_2$ chip is used as the carrier body 330 in the embodiment of FIG. 20 from which the data in FIG. 21 was obtained. The silicon body 330 is covered by an insulating diaphragm 332 comprising $Si_3N_4SiO_2$. This diaphragm has been made accessible from the silicon body side by silicon etching. The access from the opposite side is restricted to an adhesive or contact zone that surrounds an aperture 334 located within the freestanding part of the insulating diaphragm 332. Placement of cells and vesicles over the diaphragm aperture allows electrical recordings as described below in connection with FIG. 19.

The contact zone used in the embodiment of FIG. 20 from which the FIG. 21 data was obtained had a diameter of 15 μm and the diameter of the aperture was 3 μm. The contact zone was formed of $SiO_2$ covered by physisorped Poly-L-Lysine. Physisorption was accomplished by 12 hours immersion of the carrier body in a solution of 0.1% by weight of Poly-L-Lysine that was provided by Sigma Diagnostics Inc. under their stock no. P8920. After addition of 85 mM KCl at a pH of 7.2 as a buffer on both sides of the carrier fluid and insertion of Ag/AgCl redox electrodes, unilamellar vesicles having a density $10^6$ to $10^7$ vesicles/ml and consisting of 70% asolectin, 25% 1-palmitoyl-2-oleoyl-sn-glycero-3-[phospho-rac-(1-glycerol)] (POPG), and 5% cholesterol by weight suspended in $H_2O$ containing 200 mM Sorbitol, were added to the upper compartment 324, as shown in FIG. 20, to a total volume of about 200 nl.

Current traces are shown in FIG. 21 before the addition of vesicles at time 0, again after about 30 sec after addition of the vesicles, and then at about 4 minutes after the addition of alamethicin, which is a pore forming peptide that produces typical current modulations at the applied voltage V. All traces of current were referenced to the 0 pA base line, which is shown in FIG. 21 as a dashed line. To avoid electrophoretic positioning and other undesirable artifacts of current measurement, a voltage clamp was turned off during positioning and positive voltages were not applied until afterwards. This action counteracted electrophoretic positioning during current measurement.

The redox electrodes used for voltage application and current recordings can be directly attached to the carrier. Those electrodes will usually be underneath the hydrophobic surface coat and directly in contact with the buffer interfacing the contact zone. Electrodes of Ag or Pd can be sputtered or evaporated directly onto the carrier. Conductive silver inks can be used to print electrodes onto the carrier. Normally, it is necessary to chlorinate electrodes by immersion of the entire carrier into a $Cl_2$ atmosphere when working with silver. All of these methods are suited for bulk processing of large carrier quantities or carriers containing multiple contact and recording sites.

Undesirable artifacts caused by conductive or semiconductive carrier body materials, including silicon, can be reduced or eliminated by adding an insulating layer 340 to the carrier body before recording. The insulating layer reduces capacitive artifacts, including capacitive noise, that arises when a large area of the diaphragm is located between the fluid compartment and the carrier body due to an increase in capacitance C. Insulation is of importance for all types of electrical measurements and recording set-ups based on chips used for the carrier body that contain semiconductive or conductive material. Insulation is particularly useful for set-ups having large areas of a thin insulating diaphragm directly sandwiched between the seiniconductive carrier body and the fluid conipartrnent, as in U.S. patent application Ser. No. 09/581,837, filed Jun. 16, 2000 (now U.S. Pat. No. 6,258,961), which is incorporated herein by reference in its entirety for all purposes.

The method for positioning the membranous objects on the carrier and the apparatus described can also be combined with other types of electrical recording apparatus than the voltage clamp, including voltage sensing devices and impedance spectroscopy techniques. The partially or fully conductive contact zone of an insulating carrier can be used as an electrode and connected to a voltage sensing device, a voltage follower. The contacting fluid volume can be connected to ground by an electrode. The skilled artisan will recognize that the arrangement could be reversed with the carrier connected to ground by an electrode and the contacting fluid connected to a voltage follower. A cell placed onto the contact zone thus provides for recording changes in the extracellular potential. These changes can be used for analyzing cells under various environmental conditions. For such a set-up, it is important to isolate the contact zone electrode sufficiently against the extracellular fluid, which is the fluid in the fluid compartment.

Standard analysis procedures used in impedance spectroscopy in connection with current-voltage and phase-shift relations are suited for the analysis of the membrane properties of cell and lipid bilayers. Applying an alternating voltage between the electrodes provides for analysis of the membrane attached to the contact zone electrode.

17C. Examples

The following numbered paragraphs describe additional and/or alternative aspects of the invention:

1. Apparatus for positioning a biological membranous object contained within a fluid that is compatible with the object, said apparatus comprising a surface having a first zone that is repulsive against the fluid and a distinct second zone adjacent the first zone that contacts the fluid, wherein said second zone has an area of less than about 500 $\mu m^2$, and wherein said first zone controls the location of the fluid in contact with said second zone, whereby biological membranous objects in the fluid are positioned in contact with said second zone.

2. The apparatus of paragraph 1, wherein the fluid is an aqueous liquid, then said first zone is hydrophobic and said second zone is at least partially hydrophilic.

3. The apparatus of paragraph 2, wherein said fluid is a cell culture medium or a physiological buffer.

4. The apparatus of paragraph 2, where the aqueous liquid is overlaid by a hydrophobic liquid that contacts said first zone.

5. The apparatus of paragraph 1, wherein said first zone is selected from the group consisting of a hydrophobic plastic material, silane, and silicon nitride.

6. The apparatus of paragraph 5, wherein said plastic material is PTFE or PDMS.

7. The apparatus of paragraph 1, wherein said second zone has been made by a spatially selective surface treatment of a homogeneous surface so that said surface attracts the fluid.

8. The apparatus of paragraph 7, where the selective surface treatment comprises a treatment medium selected from a group consisting of an oxygen plasma, UV-radiation, and reactive chemicals.

9. The apparatus of paragraph 1, wherein said second zone has a surface of pure or doped $SiO_2$.

10. The apparatus of paragraph 1, wherein said second zone is coated with a charged material.

11. The apparatus of paragraph 10, wherein the charged material is selected from the group consisting of poly-L-lysine, a charged silane, and a lipid.

12. The apparatus of paragraph 1, wherein said second zone is coated with a molecule capable of binding to a cell surface.

13. The apparatus of paragraph 12, wherein said molecule is selected from the group consisting of lamin, biotin, avidin, integrin, antibodies, and compounds that can act as agonist or antagonist to cell membrane receptors.

14. Apparatus for positioning a biological membranous object in a fluid that is compatible with the object, said apparatus comprising a body having a surface applied thereto that is repulsive against the fluid, said surface defining a contact zone on a portion of the body not covered by said surface for attracting the fluid, said contact zone having a diameter of from 0.5 to 200 $\mu m$, and wherein a fluid volume of from about 1 to 500 nl is positioned over and covers said contact zone and the membranous objects in the fluid are in contact with said contact zone.

15. The apparatus of paragraph 14 wherein said contact zone further defines an aperture and the biological membranous objects cover said aperture.

16. Apparatus for positioning a biological membranous object in a liquid that is compatible with the objects for electrical analysis of said objects, said apparatus comprising a body for separating two compartments of liquid on opposite sides thereof, a dielectric surface applied to one side of said body for separating the two liquid components and having an aperture therein providing electrical communication between the compartments, a surface covering a portion of the dielectric surface that is repulsive to the liquid and confines the liquid to a zone of contact with the dielectric surface that is defined by the repulsive surface, whereby membranous objects of interest cover said aperture, and a pair of electrodes, one in each fluid compartment, for application of voltage to cause a current to travel through the aperture and membranes covering the aperture, whereby electrical properties of biological membranous objects located over said aperture are determined.

17. The apparatus of paragraph 14, where an electrode is directly attached to the carrier body surface that is in contact with the fluid.

18. The apparatus of paragraph 17, wherein said electrodes are a redox electrodes.

19. The apparatus of paragraph 18, wherein said aperture is filled with the fluid.

20. A method for positioning a biological membranous object, comprising: providing a body comprising a surface having a first zone defining a second zone, the first zone being repulsive against a fluid and the second zone being attractive to the fluid, wherein the second zone has an area of less than about 500 $\mu m^2$; immersing an object in no greater than about 500 nl of the fluid; and loading the fluid having the object immersed therein onto the surface such that the fluid is restricted to the second zone and the object comes into contact with the second zone.

21. The method of paragraph 19, wherein the second zone comprises materials capable of interacting with the object.

22. The method of paragraph 21, wherein said second zone interacts with the object through electrical charges.

23. The method of paragraph 21, wherein the second zone interacts with the object through affinity binding.

24. The method of paragraph 21, wherein the materials are selected from the group consisting of biotin, avidin, integrin, laminin, antibodies, polylysine, and substances acting as agonists or antagonists to membrane receptors.

25. The method of paragraph 20, wherein the fluid is a cell culture medium or an aqueous cell buffer.

26. The method of paragraph 20, wherein the membranous objects are selected from the group consisting of animal cells, plant cells, bacteria cells, fungal cells, liposomes, or a portion thereof.

27. The method of paragraph 20, wherein the membranous object is a lipid bilayer.

28. The method of paragraph 20, further comprising adding additional fluid to the contact zone upon the positioning of the membranous particle on the second zone, up to a maximum of about 500 nl.

29. The method of paragraph 20, wherein the second zone has an aperture having an area of from about 0.01 to about 50 $\mu m^2$.

30. A method for studying a membranous object comprising: loading the membranous particle onto the apparatus of paragraph 1; and analyzing the membranous particle on the apparatus.

31. The method of paragraph 30, wherein said step of analyzing the membranous object comprises electrical recording.

32. The method of paragraph 31, wherein the electrical recording is a voltage clamp recording performed by applying a voltage difference across the positioned membranous object.

33. The method of paragraph 32, wherein the electrical recording is obtained from an impedance-spectroscopic measurements.

34. The method of paragraph 30, wherein the step of analyzing the membranous object comprises optical analysis of said membranous object.

Example 18

Analysis of Ion Channel Proteins

This example describes systems, including apparatus and methods, for the functional analysis of membrane proteins. These systems may include methods for the reconstitution of membrane proteins derived from biological cells into artificial membranes so as to facilitate their analysis using electrical and optical techniques.

18A. Background

Standard methods used for the electrophysiological analysis of ion channels and biological membranes, such as standard patch clamp techniques (B. Sakmann and E. Neher, Eds., *Single-Channel Recording*, Plenum, 1983), black lipid membrane techniques ("BLM": W. R. Schlue and W. Hanke, *Planar Lipid Bilayers*, Academic Press, 1993), and voltage clamp techniques (J. G. Nicholls, *From Brain to Neuron*, Sinauer Association, Sunderland, 1992) are limited in performance due to the slow and typically manual handling of the membranes. Recent methods permit the automated positioning of biological and artificial membranes (e.g., U.S. patent application Ser. No. 09/581,837, filed Jun. 16, 2000, which is incorporated herein by reference in its entirety for all purposes) on structured carriers in such a way that electrical and optical measurements on them are possible. These methods also permit integration and miniaturization of several such systems on one carrier.

However, the analysis of cell membranes directly still requires the maintenance of cell lines in culture, or the availability of donors for primary cells. Additionally, some cells are not compatible with such new techniques due to unfavorable surface properties (e.g., they lack surface charge or have an extracellular matrix) or due to general inaccessibility (e.g., because they are bound to tissue, or possess an unfavorable morphology). In other cases, it would be helpful to study intracellular membranes that are not normally directly accessible.

Attempts to circumvent these problems by purifying the protein of interest and subsequently reconstituting it into an artificial bilayer positioned on a carrier may fail due to problems associated with finding the right purification/reconstitution protocols for each protein. Moreover, such manipulation risks the loss of possible membrane-bound cofactors or native lipids that are required for proper function of the membrane protein of interest (W. R. Schlue and W. Hanke, *Planar Lipid Bilayers*, Academic Press, 1993).

18B. Summary

The invention provides methods for analyzing membrane proteins. In one embodiment, the methods involve the fusion of small vesicles derived from the cell membrane, or the membrane of an intracellular organelle, into lipid membranes that have been formed by autopositioning giant vesicles on a mostly insulating carrier, followed by the subsequent electrical and/or optical analysis of the membrane proteins. The methods provide a powerful tool for the analysis of membrane proteins, with applications to pharmacology, biosensors, and other scientific fields.

18C. Detailed Description

The invention provides methods for the electrical and/or optical analysis of membrane proteins. These methods may partially or completely circumvent the need for preparing and/or maintaining primary cells or cell cultures, as well as the difficulties attending the complicated protein reconstitution processes associated with such analyses. The methods are based on the formation of lipid bilayers that are tightly bound to a carrier material, for example, by the "autopositioning" of giant vesicles (e.g., U.S. patent application Ser. No. 09/581,837, filed Jun. 16, 2000, and now U.S. Pat. No. 6,758,961, which is incorporated herein by reference in its entirety for all purposes) and the fusion of small, cell-derived vesicles into this bilayer. The methods of the invention may be used for the direct electrophysiological analysis of ionotropic membrane proteins, as well as for the analysis of various associated proteins and factors. The methods additionally permit the optical analysis of such proteins.

The term "autopositioning," as used here, refers to any and all methods that lead to a positioning of vesicles and cells at a predetermined position as a result of preexisting or imposed constraints (e.g., electrical and magnetic fields, and/or shape or geometry of the setup) during the positioning process. These constraints do not necessarily require manual or user-intervention during the positioning process.

For the analysis of membrane proteins, such as ion channel proteins, small vesicles containing the protein of interest (i.e., proteoliposomes) are derived, typically directly, from biological cells. The vesicle-containing suspension then is added to one or both sides of a small lipid bilayer (diameter <20 µm) that has been formed by autopositioning 5 (for example, by electrophoretic positioning as described in U.S. patent application Ser. No. 09/581,837, filed Jun. 16, 2000, and now U.S. Pat. No. 6,758,961 which is incorporated herein by reference in its entirety for all purposes) and subsequent tight adhesion of a large unilamellar vesicle across a small opening positioned in a mostly insulating carrier. Both sides of the bilayer are in contact with a small fluid volume (usually 0.1 - 100 µL) that is itself in contact with electrodes suitable for voltage-clamp recordings. Experimental conditions are chosen so that the proteoliposomes approach the bilayer membrane, attach to the membrane, and eventually fuse to the membrane. To permit subsequent fluorescence and/or confocal optical measurements of the lipid bilayers, the carrier may be designed in such a manner that the bilayer may be readily placed in the focus of a lens. For example, the carrier may be designed so as to have a generally planar conformation.

The small cell-derived vesicles (or proteoliposomes), generally having a diameter less than about 500 nm, may be obtained by various procedures. Depending on the particular procedure used, other proteins and factors that are important for the functioning of the membrane protein of interest may be contained in the vesicle, or attached to its membrane, so that upon vesicle fusion these additional proteins and factors are located in or near the preformed bilayer membrane.

The small size of the preformed bilayer membrane also permits another very efficient reconstitution method. The stability of the bilayer increases if the diameter of the aperture is reduced, as the diameter of the bilayer also is reduced. The diameter of the bilayers is less that about 20 µm, and typically less than about 5 gm, for example, as described in U.S. patent application Ser. No. 09/581,837, filed Jun. 16, 2000 (now U.S. Pat. No. 6,758,961), which is incorporated herein by reference in its entirety for all purposes. Consequently, the bilayers are significantly more stable than typical black lipid membrane bilayers. Under these coniditions, detergent-solubilized membrane proteins, such as the nicotinic acetylcholine receptor or CIC-O channel from Torpedo mannorai, may be added directly to one of the buffer compartments in contact with the preformed bilayer. For the solubilization of the membrane protein, a purification step typically is not required. In most cases, it is sufficient to solubilize the original membrane (e.g., plasma membrane, endoplasmic reticulum membrane (ER), mitochondrial membranes) in detergent (e.g., CHAPS: 3-((3-cholamidopropyl) dimethylammonio)-1-propanesulfonate) and to add a sufficient volume of solubilized membrane to one or both sides of the bilayer. After an optional washing step of the respective compartment, the membrane proteins may be analyzed.

The proteins of interest may be analyzed in a variety of ways, once they are reconstituted into the lipid bilayer. Most commonly, a voltage is applied across the bilayer via two redox electrodes that are immersed in the fluid compartments located on one or both sides of the bilayer membrane. The current registered using these electrodes serves as a direct measure of membrane protein activity. By placing the bilayer membrane within the focal spot of an objective, the (optionally confocal) optical observation of the bilayer also may provide information about binding properties and activity of the membrane protein of interest.

In a particular embodiment, the invention permits the measurement of the current through any ionotropic membrane protein expressed in the membrane of a biological cell, including the plasma membrane, the endoplasmic reticulum, the tonoplast and thylakoid membranes of plant cells, the inner and outer membranes of mitochondria, and the inner and outer membranes of bacteria. Fluorescent labeling of a particular membrane protein or another protein attached to it (e.g., G-protein) or a ligand (e.g., in case of the nicotinic acetylcholine receptor (nAChR), the fluorescent agonist (1-(5-dimethylaminonaphthalene)-sulfonamidol)-n-hexanoic acid-beta-N-trimerylammonium bromide ethyl ester (Dns-C6-Cho)) or other factor allows as well the (confocal) optical observation and optical analysis of such protein. The method achieves such broad applicability to membrane proteins by forming small vesicles of the original membrane and fusing these vesicles into a preformed lipid bilayer.

18D. Examples

The method of the invention is readily adapted to incorporate modifications intended to permit additional specific applications, as described below. These applications are included for illustration and should not be interpreted so as to restrict, limit, or define the entire scope of the invention.

18D.1 Preparation of a Suitable Carrier

The methods described herein generally may be used with any suitable carrier, including those described herein and/or in the following U.S. patent applications, which are incorporated herein by reference in their entirety for all purposes: Ser. No. 09/581,837, filed Jun. 16, 2000 (now U.S. Pat. No. 6,758,961); and Ser. No. 09/708,905, filed Nov. 8, 2000 (now abandoned). A carrier suited for electrophoretical positioning of large liposomes may be prepared as described in U.S. patent application Ser. No. 09/581,837, filed Jun. 16, 2000 (now U.S. Pat. No. 6,758,961), which is incorporated herein by reference in its entirety for all purposes. A suitable carrier is generally insulating, but contains a small hole typically having a diameter less than about 20 µm. The carrier generally separates two fluid compartments in such a way that the hole in the carrier is in contact with both compartments. Upon application of a voltage between the compartments, mediated by redox electrodes immersed in each compartment, a strongly inhomogeneous field around the aperture is created such that vesicles, cells and other charged objects are propelled towards the aperture.

The carrier may be sandwiched between two fluid compartments, for example, confined on the carrier surface by a hydrophobic material attached/bound to the surface. Electrodes such as redox electrodes used both for the application and/or recordation of voltage may be immersed in the fluid compartments. The redox electrodes may be directly attached to the carrier (e.g., by sputtering or printing) or to a container that itself contains the carrier.

In one embodiment of the invention, the carrier is a silicon chip containing a groove that is covered by a thin silicon nitride/silicon oxide diaphragm, where the diaphragm itself contains a small aperture (diameter usually <20 µm). The chip is otherwise be surrounded by an insulating layer, such as thermally grown silicon oxide, to reduce the capacitance of the setup.

Preferably, the surface of the carrier is either selected, or is modified, so that lipid bilayers adhere to the surface tightly. For example, the surface may be modified by the physisorption of poly-L-lysine (molecular mass usually >15,000 daltons), by chemical modification with 4-aminobutyl-dimethyl-methoxysilane, or derivatization with molecules that bind (specifically or non-specifically) to cell surfaces (for example, some lectins).

In some embodiments, a silicon chip can be used as a carrier material, for example, as described in U.S. patent application Ser. No. 09/581,837, filed Jun. 16, 2000, which is incorporated herein by reference in its entirety for all purposes. The carrier contains a small opening (aperture) of about 0.3 to 20 µm on which vesicles are positioned and subsequently a lipid membrane is created. On both sides of the carrier is a small buffer compartment located so that it may be free-standing (e.g., confined to hydrophilic carrier spots surrounded by hydrophobic areas) or physically confined (i.e., by grooves put into the carrier). The buffer compartments are usually between 0.1 to 40 µL. Redox electrodes are generally made of Ag/AgCl or Platinum, and may be directly attached to the recording carrier or a cartridge in which the carrier is packaged or attached to a holder that is not in direct contact with the chip. For measurements that refer only to optical or impedance spectroscopic analysis, it may be sufficient to use carriers that do not require either apertures or electric fields for positioning. In this embodiment, only one buffer compartment is required.

In another embodiment of the invention, several recording setups are integrated on a single chip that contains several apertures. In this manner, all fluids and electrodes on one side of the carrier can be unified. On the other side of the carrier, however, fluid compartments and electrodes are necessarily separated to allow independent recordings. Separation is made possible by utilizing hydrophilic/hydrophobic surface patterning, or by producing small compartment wells on the carrier surface, for example by laminating a thin polydimethylsiloxane (or PDMS) layer containing small holes adjacent to the aperture to the carrier surface.

The carrier may have multiple recording sites, as illustrated elsewhere herein. The carrier contains on one side a patterned surface to separate fluid compartments physically and permit multiple independent recordings. Patterning is done by attachment of hydrophilic substances or materials. These fluid compartments are accessed with independent electrodes for every compartment (1,2,3, . . . ) that are independently connected to voltage clamp circuits. On the other side, while each compartment can be separated as shown for the first side, it is however more simple to unify the compartments and bring them in contact with only one electrode (typically the ground electrode). In one embodiment, the carrier is a silicon chip containing grooves that are closed by a silicon nitride/silicon oxide diaphragm containing a small aperture (diameter usually <20 µm). The chip is otherwise typically surrounded by an insulating layer, e.g., thermally grown silicon oxide, to reduce the capacitance of the setup.

18D.2 Positioning a Vesicle Across the Aperture

To place the large, preferably unilamellar vesicle across the aperture, a voltage is applied between the two carrier compartments. The voltage is typically between −1 V and +1 V, and the vesicles added to one compartment are (typically electrophoretically) attracted towards the aperture and permitted to adhere to the carrier surface surrounding the aperture. Vesicles will usually break apart upon surface adhesion and leave a membrane patch that tightly seals the aperture, typically with a seal resistance greater than 100 MOhm. It may necessary to rinse both compartments with an osmotically appropriate solution after positioning, to match the osmolarity of the small vesicle to be fused in step 4 (as discussed below).

Large vesicles that are appropriate for the purposes of the method of the invention may consist of various combinations of particular lipids in particular relative amounts. In one embodiment of the invention, the large vesicle is composed of 70% asolectin, 25% 1-palmitoyl 2-oleoyl-sn-glycero-3-[phospho-rac-(1-glycerol)] (POPG), 5% cholesterol or 45% POPE, 25% cholesterol, 22.5% 1 palmitoyl-2-oleoyl-sn-glycerol-3-phosphocholine (POPC), and 7.5% POPG. Vesicles are optionally prepared by rehydration of a thin and dried lipid film for several hours (usually more than 2 hours) with subsequent size purification to remove vesicles with diameters less than 5 µm. A film that is suitable for such rehydration is a film of 1.25 mg total lipid in 10 ml deionized water containing 200-1000 mM sorbitol. The formation of large vesicles by rehydration can be supported by the application of an AC electrical field (frequency about 10 Hz, E about 1000 V/m) as described in, for example, Mathivet L., Cribier S., and Devaux, P. F., Biophys J 1996 70(3): 1112-21, Shape change and physical properties of giant phospholipid vesicles prepared in the presence of an AC electric field. The resulting vesicles may be separated, for example by dialysis of the vesicle containing solution across a 10-µm nylon net.

The vesicles of the method may be positioned using various methods, including the applied constraints that focus the movement of the vesicles towards the recording site (e.g., aperture) or that only allow the attachment of vesicles at that place, as discussed above. Examples of such constraints include, without limitation, electric and dielectric forces, hydrophilic-hydrophobic surface patterning, and physical constraints of the setup, such as a cone-shaped compartment and/or liquid streams. For positioning, a small volume (usually 0.1 to 10 µL) of a gant vesicle-containing solution is added to the fluid compartment. The utilization of inhomogeneous electrical fields is particularly useful, for example, as described in U.S. patent application Ser. No. 09/581,837, filed Jun. 16, 2000 (now U.S. Pat. No. 6,758, 961), which is incorporated herein by reference in its entirety for all purposes. In this method, a voltage of about 10 to 200 mV (absolute value) is applied between the two fluid compartments located on both sides of the recording aperture of the carrier. As the voltage drop between the electrodes peaks near and within the aperture, there is a resulting very high field strength in this area that attracts charged vesicles to the aperture, where the field strength is highest. After vesicle positioning, any remaining giant vesicles may be washed away.

To make electrical recordings, a very tight adhesion of the giant vesicles and its remaining membrane with the carrier is required (a so-called "Giga-Seal"). The seal resistance between carrier and membrane should be >100 MΩ. Such resistances are promoted by smooth carrier surfaces and strong interaction (electrostatic forces, molecular recognition/binding) between carrier and membrane.

18D.3 Manufacturing of Small Vesicles Directly Derived from Cellular Membranes

Suitable small vesicles may be prepared using any of a variety of different methods, including for example:

Destruction of the cytoskeleton, for example using cytochalasin.

Application of mechanical shear-forces to the cell or cell fragments (e.g., by pressing cells through a filter membrane as described by Regueiro P., Monreal J., Diaz R. S., and Sierra F., J Neurochem 1996 67(5):2146-54, Preparation of giant myelin vesicles and proteoliposomes to register ionic channels.).

Solubilization of the membrane and subsequent detergent removal (by dialysis).

Purification of vesicles produced by osmotically driven shrinking of cells (Kubitscheck U., Homann U., and Thiel G., Planta 2000 210(3):423-3, Osmotically evoked shrinking of guard-cell protoplasts causes vesicular retrieval of plasma membrane into the cytoplasm).

Isolation of vesicles produced by other endocytotic processes (e.g., Sattsangi S., and Wonderlin W. F., Methods Enzymol 1999 294:339-50, Isolation of transport vesicles that deliver ion channels to the cell surface).

Isolation of synaptic vesicles (Kelly M. L., and Woodbury D. J., Biophys J 1996 70(6):2593-9, Ion channels from synaptic vesicle membrane fragments reconstituted into lipid bilayers).

Ultrasonification of cells.

Alternatively, suitable small vesicles may be obtained directly from a variety of native sources, including:

Cytoplasmatic droplets of *Chara corallina*, made by cutting an internodal cell in 1M NaCl solution. The resulting droplets are surrounded by tonoplast, while larger vesicles may also be directly positioned across the recording aperture (Bertl A., J Membrane Biol 1989 109:9-19, Current-voltage relationships of a sodium sensitive potassium channel in the tonoplast of *Chara corallina*).

Cholinergic synaptic vesicles isolated from the electric organ of *Torpedo californica* (Kelly M. L., and Woodbury D. J., Biophys J 1996 70(6):2593-99, Ion channels from synaptic vesicle membrane fragments reconstituted into lipid bilayers).

Transport vesicles isolated from cultured cells (e.g., N1E-115 cells: Sattsangi S., and Wonderlin W. F., Methods Enzymol 1999 294:339-50, Isolation of transport vesicles that deliver ion channels to the cell surface).

It generally is important that the vesicles used in the method be small, typically less than 500 mm in diameter, preferably even less than 150 mm in diameter, to encourage an effective fusion of vesicles to the lipid bilayer. In some embodiments, this vesicle suspension may be purified, for example by centrifugation (removal of supernatant solution and addition of clean buffer) or by dialysis.

18D.4 Adhesion and Fusion of Vesicles

Upon the addition of a suspension of small vesicles to one of the buffer compartments, the small vesicles will be in constant motion, due to turbulences, thermal movement, gravity, and other forces, and the vesicles will eventually touch the bilayer. To promote the adhesion and fusion of the vesicles to the lipid bilayer, the addition of calcium ions, zinc ions, polyethylene glycol (PEG) or any combination thereof to the buffer may be appropriate. Calcium ions are typically added to a concentration of about 40 mM, and zinc ions are added to a concentration of about 200 µM).

Fusion of the adhering vesicles is also strongly promoted by imposing mechanical stresses to them, or to the bilayer membrane to which they are fused (and which covers the aperture). Such stress may be induced by osmotic swelling of the vesicles, for example by reduction of the osmolarity of the buffer medium (e.g., to about 50% of its original value). Suitable stress to promote fusion may also be created by strongly increasing the osmolarity of the solution on the vesicle containing side of the aperture with respect to the solution on the other side of the aperture (Cohen F. S., Zimmerberg J., et al., J Gen Physiol 1980 75(3):251-70, Fusion of phospholipid vesicles with planar phospholipid bilayer membranes. II. Incorporation of vesicular membrane market into the planar membrane). A sophisticated variant of this method involves the semi-permeabilization of the membrane (Woodbury D. J., Methods Enzymol 1999 294:319-39, Nystatin/ergosterol method for reconstituting ion channels into planar lipid bilayers).

18D.5 Addition of Solubilized Membrane Proteins

As an alternative to the methods of Example 4, detergent solubilized membrane proteins may be added to one compartment, and integration of those proteins into the bilayer will take place automatically without the need for further process steps.

The addition of solubilized membrane proteins requires that such proteins remain functional (i.e., are not denatured) upon solubilization with the addition of detergent. Examples of appropriate solubilization procedures include the solubilization of the CIC chloride channel with the addition of CHAPS to membrane preparations of *Torpedo marmoraia* (solubilized in 85 mM KCl, 4 mM NACl, 1 mM HEPES pH 7.4 and 59 mM CHAPS with 2 mg/ml lipids (85% asolectin, 8% cholesterol and 7% POPG). The suspension is 200-fold diluted in buffer immediately before addition to the sample compartment (final channel protein concentration of <10 pg/µL)).

The use of solubilized membrane proteins does not require the isolation or production of proteoliposomes, nor does it require the utilization of osmotic stress to integrate the membrane protein into the bilayer.

18D.6 Post-Integration Analysis

After membrane protein integration, the compartment may be rinsed to remove excess vesicles or detergent traces. Rinsing may also be needed to change the buffer composition, if needed. Membrane proteins may then be analyzed by monitoring the membrane current at a given voltage, with the addition if necessary addition of ligands, co-factors, etc. Alternatively, the membrane proteins may be analyzed by confocal observation of the lipid bilayer patch (and consequently reconstituted membrane protein) covering the carrier aperture.

For electrical recordings, a voltage is typically applied across the bilayers membrane via the redox electrodes immersed in the buffer compartments (in case of U.S. patent application Ser. No. 09/581,837, filed Jun. 16, 2000, and now 6,758,961 which is incorporated herein by reference in its entirety for all purposes). (It can be the same electrodes as used for positioning). The resulting current represents a direct measure of membrane protein activity.

For optical measurements, the membrane in which the proteins have been integrated is located within the focal point of an objective lens or the beam path of a laser. The membrane is typically illuminated at an appropriate excitation wavelength, and the resulting fluorescence is monitored. Typically, the fluorescence intensity and time-course are monitored. A variety of fluorescence-based techniques are available, including the binding of fluorescently labeled compounds to the membrane, or monitoring energy transfer between fluorescent parts of the membrane (including appropriately fluorescently labeled compounds). To increase the signal to noise ratio of the fluorescence signal, all light received from non-confocal areas can be eliminated before reaching the detector by e.g., placing an aperture within the confocal plane.

The method of the invention is also useful for screening the interactions between the membrane proteins and a variety of compounds, by observing the effect on protein activity, binding affinity, or binding modulation of the membrane proteins.

The method of the invention optionally may be performed using apparatus, methods, and/or compositions described in the various patents, patent applications, and other material listed above under Cross-References and incorporated herein by reference. The apparatus include planar electrophysiology substrates, electrical positioning and measurement devices, luminescence detectors, and sample holders such as microplates, among others. The methods include electrophysiology methods, such as patch clamp and voltage clamp methods, among others, and photoluminescence methods, such as fluorescence intensity, polarization, and energy transfer methods, among others. The compositions include photoluminescent probes, and precursors and partners thereof, such as polarization probes and energy transfer probes, including donors and acceptors, particularly for measuring membrane potentials and/or the presence or concentration of selected ions, including $Na^+$, $K^+$, $Cl^-$, and/or $Ca^{2+}$, among others.

Figure 22:
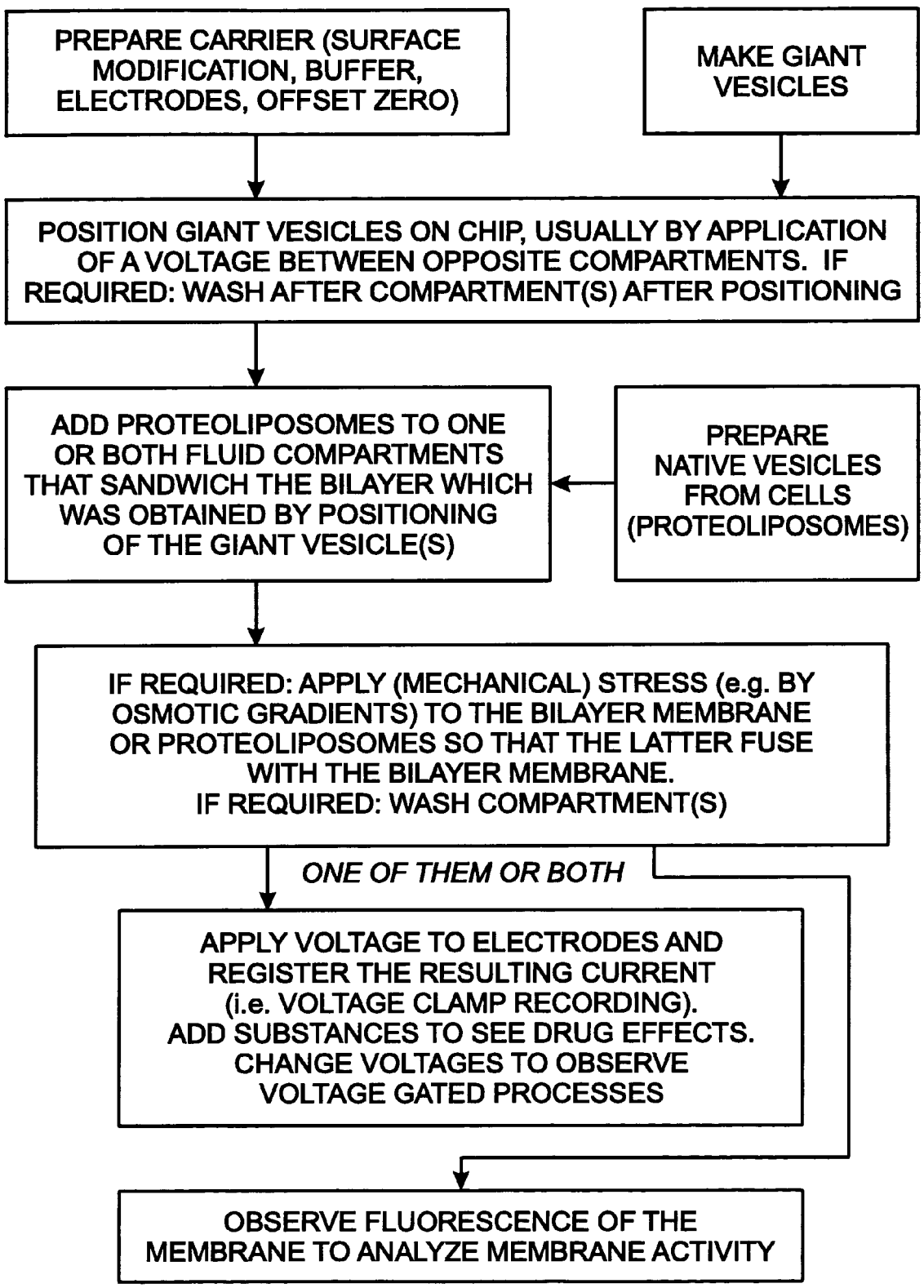
FIG. 22 is a flow chart showing the steps leading from a biological cell to a reconstituted membrane protein that can be analyzed.

An overview of the key process steps of the instantly described new method of membrane protein analysis is given in FIG. 22.

18D.7 Additional Examples

The following numbered paragraphs describe additional and/or alternative aspects of the invention:

1. A method of analyzing membrane proteins, comprising (A) positioning a vesicle on a substantially insulating carrier; (B) forming a lipid membrane on the carrier; (C) forming one or more smaller vesicles that contain at least one membrane protein, where the smaller vesicles are derived from a cell membrane or organelle membrane; (D) incorporating the membrane protein in the lipid membrane by fusing the small vesicles with the lipid membrane; and (E) analyzing the membrane protein.

2. The method of paragraph 1, where the step of analyzing comprises electrical analysis of the membrane protein.

3. The method of paragraph 1, where the step of analyzing comprises optical analysis of the membrane protein.

4. The method of paragraph 1, where the carrier separates two fluid compartments, and includes a small aperture between the two fluid compartments.

5. The method of paragraph 4, where the vesicle is positioned on the carrier across the aperture by generating a voltage difference between the fluid compartments.

6. The method of paragraph 1, where the carrier is in contact on one side with at least one fluid compartment that is confined to such a small area that the lipid membrane will form at a particular position.

7. The method of paragraph 1, where one carrier comprises a plurality of distinct sites for analyzing membrane proteins.

8. The method of paragraph 1, where a surface of the carrier is chemically or physically modified so as to enhance the formation of a high electrical seal with the lipid bilayer.

9. The method of paragraph 1, where the membrane protein is analyzed using voltage-clamp techniques.

10. The method of paragraph 1, where the carrier further comprises a conductive material, and where the step of analyzing comprises analyzing the membrane protein using impedance spectroscopy.

11. The method of paragraph 1, further comprising orienting the lipid bilayer in the focal plane of an objective lens.

12. The method of paragraph 3, where the optical analysis comprises confocal observation.

13. The method of paragraph 1, where the smaller vesicles are derived by endocytosis, exocytosis, or synaptic vesicle release.

14. The method of paragraph 1, where the smaller vesicles are derived by mechanical destruction of a cell or chemical destruction of a cytoskeleton.

15. The method of paragraph 1, further comprising sorting the smaller vesicles according to origin and membrane protein content prior to incorporating them into the lipid bilayer.

16. The method of paragraph 1, where the step of incorporating is promoted by the presence of polyvalent cations, fusogenic proteins, or both.

17. The method of paragraph 1, where the step of incorporating is promoted by the application of osmotic stress on the lipid bilayer or the smaller vesicles or both.

18. A method of analyzing membrane proteins, comprising (A) positioning a vesicle on a substantially insulating carrier; (B) forming a lipid membrane on the carrier; (C) forming one or more membrane fractions that contain at least one membrane protein, where the membrane fractions are derived by solubilization of a cell membrane or organelle membrane; (D) incorporating the membrane protein in the lipid membrane by integrating the membrane fractions into the lipid membrane; and (E) analyzing the membrane protein.

Example 19

Miscellaneous Applications 1

This example describes a variety of exemplary applications of the positioning and measurement systems provided by the invention.

19A. Screening of Ingredients

The system may be used to screen libraries according to any suitable criterion, such as the identification of candidate drugs, modulators, and the like. Suitable libraries include compound libraries, combinatorial chemistry libraries, gene libraries, phage libraries, and the like. The system is exceptionally well suited to probing libraries whose members are present only in small amounts, such as (1) the large number of potential ligands that can be produced using combinatorial chemistry, and (2) many receptor proteins, above all ligand-controlled and G-protein-coupled receptors (GPCRs). Owing to the process according to the invention, or alternatively the measurement arrangement/measurement apparatus according to the invention, it is possible to work with very few cells, either directly or after previous isolation and reconstitution of the receptor proteins in vesicles or lipid membranes. By the uncomplicated arrangements of the sensor elements in arrays, different substances or receptors can be selected simultaneously. There is moreover the possibility of receptor cleaning and reconstitution in lipid vesicles microchromatographically in on-chip containers that optionally may be integrated into the apparatus according to the invention.

19B. Replacement of Conventional Patch-clamp Technologies

Conventional patch-clamp technologies form the foundation of the investigation of the functionality of membrane receptors as well as the modification of membrane characteristics as a response to signal and metabolic processes in cells. If isolated cells of a homogeneous cell population serve as the object of the investigation, as is, for example, often the case in transformed cells, the process according to the invention serves as an at least comparable replacement for the patch-clamp technologies. As objects of investigation for this process, for example, dissociated neurons and cultivated mammalian cells as well as plant protoplasts are suitable.

19C. Portable Biosensors/Environmental Analytics

The automation and outstanding mechanical stability of the measurement system according to the invention permits its use in biosensors. By using suitable transformed cells, receptors reconstituted in vesicles, or channel-forming proteins, sensors can be set up that are sensitive to very different substrates or metabolites. Moreover, if sufficiently tight electric seals are formed, which is possible using the apparatus according to the invention, then measurement sensitivity will in principle only be dependent on the binding constant of the receptor. This sensitivity may lie under one nanomole for G-protein-coupled receptors, and in the nanomolar range for ionotropic receptors (e.g., 5 HT3, nAChR, $GABA_AR$, glycine R, and GluR).$^{xx}$ Example 20

Miscellaneous Applications 2

This example describes additional selected embodiments of the invention, primarily relating to systems, presented as a series of indexed paragraphs.

A. A multiaperture system for analyzing samples such as cells, vesicles, and cellular organelles, and fragments, derivatives, and mixtures thereof, comprising (1) a carrier having a plurality of apertures, the carrier being adapted so that at least one of the samples can be sealed across at least one of the apertures; (2) at least two fluid compartments, connected via at least one of the apertures; and (3) at least two electrodes in electrical contact with at least one of the fluid compartments, wherein the electrodes are adapted to measure at least one of an electrical potential and a current, across at least a portion of the at least one of the samples.

B. A multiaperture system for analyzing samples such as cells, vesicles, and cellular organelles, and fragments, derivatives, and mixtures thereof, comprising (1) a holder; and (2) a plurality of measurement sites disposed in the holder, each measurement site having a carrier that separates from one another two fluid compartments; wherein the carrier contains an aperture that connects the two compartments, the carrier being adapted so that a sample can be sealed across the aperture; and wherein each compartment is in electrical contact with at least one electrode, the electrodes being adapted to measure at least one of an electrical potential and a current, across at least a portion of the sample.

C. A multiaperture system for positioning and/or analyzing samples such as cells, vesicles, and cellular organelles, and fragments, derivatives, and mixtures thereof, comprising (1) a carrier having a plurality of apertures, the carrier being adapted so that at least one of the samples can be sealed across at least one of the apertures; (2) at least one sample fluid compartment and at least one reference fluid compartment, in contact via the apertures; and (3) at least one sample electrode and at least one reference electrode, each sample electrode in contact with at least one of the sample fluid compartments, and each reference electrode in contact with at least one of the reference fluid compartments, wherein the at least one sample electrode and the at least one reference electrode are adapted to apply and/or measure an electrical potential across the apertures.

1. The system of paragraph A, B, or C, wherein the samples are selected from the group consisting of cells, vesicles, and biological organelles, and fragments thereof.

2. The system of paragraph 1, wherein the samples are selected from the group consisting of transformed cells, dissociated neurons, and cultivated mammalian cells.

3. The system of paragraph 2, wherein the samples are transformed cells.

4. The system of paragraph 2, wherein the samples are dissociated neurons.

5. The system of paragraph 2, wherein the samples are cultivated mammalian cells.

6. The system of paragraph A, B, or C, wherein the samples are selected from the group consisting of natural, artificial, and modified lipid membranes.

7. The system of paragraph A, B, or C, wherein at least one electrode is used for measurement over more than one aperture.

8. The system of paragraph 7, wherein the at least one electrode is a reference electrode.

9. The system of paragraph A, B, or C, wherein several or all of the electrodes on one side of the carrier have a common electrical potential.

10. The system of paragraph A, B, or C, wherein several or all of the electrodes on one side of the carrier are combined to form one electrode.

11. The system of paragraph A, B, or C, wherein the compartments and electrodes are separated on one side of the carrier to allow independent measurements.

12. The system of paragraph 11, there being twice as many electrodes as apertures, wherein the compartments and electrodes are separated on both sides of the carrier.

13. The system of paragraph A, B, or C, wherein the compartments and electrodes are partially or totally combined on one side of the carrier.

14. The system of paragraph A, B, or C, there being twice as many electrodes as apertures, wherein the electrodes and apertures are disposed so that there is always one aperture between two electrodes.

15. The system of paragraph A, B, or C, wherein the carrier comprises a single chip with multiple apertures.

16. The system of paragraph A, B, or C, wherein the carrier comprises several chips, each with one aperture.

17. The system of paragraph A, B, or C, wherein the system is configured for sequential measurements over at least two apertures.

18. The system of paragraph A, B, or C, wherein the system is configured for parallel measurements over at least two apertures.

19. The system of paragraph A, B, or C, wherein the electrodes are positioned symmetrically about the aperture.

20. The system of paragraph A, B, or C, wherein the electrodes are positioned at a distance of between about 0.5 mm and about 3 mm from the carrier.

21. The system of paragraph A, B, or C, wherein the electrodes are redox electrodes.

22. The system of paragraph A, B, or C, wherein the electrodes are selected from the group consisting of silver electrodes, silver/silver chloride electrodes, and platinum electrodes.

23. The system of paragraph A, B, or C, wherein one electrode and at least one aperture are connected to one another through a channel or a chamber in a spacer, with the formation of an open or closed compartment.

24. The system of paragraph A, B, or C, wherein the diameter of the aperture is less than about 15 μm.

25. The system of paragraph 24, wherein the diameter of the aperture is between about 0.3 μm and about 7 μm.

26. The system of paragraph 25, wherein the diameter of the aperture is between about 1 μm and about 5 μm.

27. The system of paragraph A, B, or C, wherein the diameter of the aperture is about one-tenth the diameter of the sample.

28. The system of paragraph A, B, or C, further comprising a sample-handling mechanism for adding, manipulating, exchanging, storing, and/or removing samples and sample components from at least one compartment.

29. The system of paragraph 28, wherein the sample-handling mechanism is configured to add fluid and/or store fluid and/or exchange fluid on one or both sides of the carrier.

30. The system of paragraph 28, wherein the sample-handling mechanism is configured to add cells, vesicles, and other biological organelles or particles on one or both sides of the carrier.

31. The system of paragraph 28, wherein the sample-handling mechanism is configured to separate samples or sample components.

32. The system of paragraph 31, wherein the separation is performed using capillary electrophoresis (CE) or high-pressure fluid chromatography (HPLC).

33. The system of paragraph 31, wherein the sample-handling mechanism is further configured to analyze the separated substances.

34. The system of paragraph 28, wherein the sample-handling mechanism is configured to check the fluid level in the compartments.

35. The system of paragraph 34, wherein the checking is performed continuously or regularly.

36. The system of paragraph 34, wherein the sample-handling mechanism is further configured to correct the fluid level according to a preset filling parameter, if an error is detected during checking.

37. The system of paragraph 28, wherein the sample-handling mechanism can add fluid or samples to arbitrary compartments.

38. The system of paragraph 28, wherein the sample-handling mechanism can exchange fluid or samples at arbitrary compartments.

39. The system of paragraph 28, wherein the sample-handling system is coupled to at least one compartment through a tubing.

40. The system of paragraph 28, wherein the sample-handling system is based on pumps, hydrostatic pressure differentials, electro-osmotic processes, piezo drop-on-demand processes, ink-jet processes, contact transfer processes, temperature-controlled processes, and/or mechanical displacement.

41. The system of paragraph 28, wherein the sample-handling system is configured to introduce samples into a compartment through an inlet opening arranged concentrically above the aperture.

42. The system of paragraph 41, wherein the sample arrives near the aperture by at least one of convection and sedimentation.

43. The system of paragraph 41, wherein the sample is moved onto the aperture electrophoretically.

44. The system of paragraph 41, wherein the inlet opening is at least substantially circular.

45. The system of paragraph 41, wherein the diameter of the inlet opening is between about 0.2 mm and about 1 mm.

46. The system of paragraph A, B, or C, further comprising means for adding, manipulating, exchanging, storing, and/or removing samples and sample components from at least one compartment.

47. The system of paragraph A, B, or C, wherein the sample arrives near the aperture by at least one of convection and sedimentation.

48. The system of paragraph 47, wherein the sample is moved electrophoretically onto the aperture.

49. The system of paragraph A, B, or C, wherein the carrier is at least substantially planar.

50. The system of paragraph A, B, or C, wherein the carrier has an electrically charged surface that attracts biological membranes.

51. The system of paragraph 50, wherein the electrically charged surface is produced by modification.

52. The system of paragraph 51, wherein the modification is produced with the aid of polycations and/or silanes.

53. The system of paragraph A, B, or C, wherein the carrier has a surface that provides a molecule-specific bonding of cells, vesicles, membrane fragments, or biological organelles on it.

54. The system of paragraph 53, wherein the molecule-specific bonding is mediated by biotin-streptavidin interactions or histidine-nitriloacetic acid interactions.

55. The system of paragraph A, B, or C, wherein the carrier has a surface that provides a multivalent-ion-mediated bonding of cells, vesicles, membrane fragments, or biological organelles on it.

56. The system of paragraph 55, wherein the multivalent-ion-mediated bonding is mediated by $Ca^{2+}$ ions.

57. The system of paragraph A, B, or C, wherein the bonding between the sample and the carrier is tight enough so that the variance of leakage currents through the aperture during electrical measurements lies below the signals to be measured by 0.1-50 pA at $V_M$=−60 mV by a factor of 5-10.

58. The system of paragraph A, B, or C, wherein the carrier has a coating with an electrically charged surface that attracts biological membranes.

59. The system of paragraph A, B, or C, wherein the carrier is cleaned in an oxygen plasma before the surface of the carrier is modified or immediately before the carrier is used.

60. The system of paragraph A, B, or C, wherein the carrier is made partially or completely hydrophilic before the surface of the carrier is modified or immediately before the carrier is used.

61. The system of paragraph A, B, or C, wherein the sample is modified to enhance bonding between the sample and the carrier.

62. The system of paragraph 61, the carrier surface being charged, wherein the sample is modified by charging its surface with a charge opposing that on the carrier surface.

63. The system of paragraph A, B, or C, further comprising means for enhancing the binding between the sample and the carrier.

64. The system of paragraph A, B, or C, wherein the carrier is electrically insulating.

65. The system of paragraph A, B, or C, wherein the carrier is formed at least in part of materials selected from the group consisting of silicon, silicon derivatives, glass, and plastic.

66. The system of paragraph A, B, or C, wherein the carrier is formed at least in part of silicon.

67. The system of paragraph 66, wherein the carrier includes an applied oxide or oxynitride layer.

68. The system of paragraph 66, wherein the carrier comprises a silicon chip or a silicon wafer.

69. The system of paragraph A, B, or C, the surface of the carrier having hydrophilic and hydrophobic regions, wherein the hydrophilic regions are disposed around the apertures.

70. The system of paragraph 69, wherein the hydrophobic regions are disposed between the apertures, so that the hydrophilic and hydrophobic regions define the fluid compartments.

71. The system of paragraph A, B, or C, wherein the compartments on at least one side of the carrier are open.

72. The system of paragraph 71, wherein fluid is fixed in the open compartments at least in part by capillary forces.

73. The system of paragraph 71, wherein fluid is fixed in the open compartments at least in part by hydrophilic/hydrophobic forces.

74. The system of paragraph 71, wherein fluid is fixed in the open compartments at least in part by surface tension.

75. The system of paragraph 71, wherein the compartments on the sample side of the carrier are open.

76. The system of paragraph A, B, or C, wherein the compartments on at least one side of the carrier are closed.

77. The system of paragraph A, B, or C, wherein the compartments on at least one side of the carrier have a physical boundary on the side.

78. The system of paragraph A, B, or C, wherein the compartments on at least one side of the carrier have no physical boundary on the side.

79. The system of paragraph A, B, or C, wherein at least two fluid compartments are disposed on one side of the carrier, each of those compartments being in contact, via the apertures, with a single fluid compartment disposed on the other side of the carrier.

80. The system of paragraph A, B, or C, wherein the volume of each compartment is no more than about 100 microliters.

81. The system of paragraph A, B, or C, further comprising a sample-analysis mechanism for analyzing samples positioned about at least one aperture, other than by direct electrical measurement using the positioning and measurement system.

82. The system of paragraph 81, wherein the sample-analysis mechanism is configured for optical measurements.

83. The system of paragraph 82, wherein the sample-analysis mechanism is configured for fluorescence measurements.

84. The system of paragraph 82, wherein the system is configured for simultaneous optical and electrical measurements.

85. The system of paragraph A, B, or C, further comprising means for analyzing samples positioned about at least one aperture, other than by direct electrical measurement using the positioning and measurement system.

86. The system of paragraph A, further comprising a holder adapted to support the carrier.

87. The system of paragraph 86, the holder being substantially rectangular, wherein the length of the holder ranges between about 125 mm and about 130 mm, and wherein the width of the holder ranges between about 80 mm and about 90 mm.

88. The system of paragraph 86, wherein the holder is a microplate frame.

89. The system of paragraph A, B, or C, wherein the number of apertures is selected from the group consisting of 96, 384, and 1536.

90. The system of paragraph A, B, or C, wherein the density of apertures is at least about 1 aperture per 81 $mm^2$.

90A. The system of paragraph B, the holder being substantially rectangular, wherein the length of the holder ranges between about 125 mm and about 130 mm, and wherein the width of the holder ranges between about 80 mm and about 90 mm.

91. The system of paragraph B, wherein the holder is a microplate frame.

92. The system of paragraph A, B, or C, wherein the application of a voltage difference across the aperture, mediated by the electrodes, causes samples to move toward the aperture.

93. The system of paragraph 92, wherein the voltage difference creates an inhomogeneous electric field around the aperture, which becomes larger as the aperture is approached.

94. The system of paragraph 92, wherein the voltage difference creates an electric field sufficient to cause the sample to seal to the carrier across the aperture.

95. The system of paragraph 92, wherein the voltage difference creates an inhomogeneous electric field around the aperture, the magnitude of the field being at least about 100 V/m adjacent the aperture.

96. The system of paragraph 92, wherein the voltage difference between the electrodes is in the range from about −200 mV to about +200 mV.

97. The system of paragraph A, B, or C, wherein the application of a voltage difference, mediated by the electrodes, creates an inhomogeneous electric field around the aperture, which becomes larger as the aperture is approached.

98. The system of paragraph 97, wherein the voltage difference creates an electric field sufficient to cause the sample to seal to the carrier across the aperture.

99. The system of paragraph 97, wherein the voltage difference creates an inhomogeneous electric field around the aperture, the magnitude of the field being at least about 100 V/m adjacent the aperture.

100. The system of paragraph 97, wherein the voltage difference between the electrodes is in the range from about −200 mV to about +200 mV.

101. The multiaperture system of paragraph B, where the carrier contains at least two apertures that connect the two compartments.

102. The multiaperture system of paragraph C, where the at least one sample fluid compartment and the at least one reference fluid compartment are disposed on opposite sides of the carrier.

Example 21

Miscellaneous Applications 3

This example describes additional selected embodiments of the invention, primarily relating to methods, presented as a series of indexed paragraphs.

E. A method for analyzing samples such as cells, vesicles, and cellular organelles, and fragments, derivatives, and mixtures thereof, comprising (1) selecting a multiaperture system according to paragraph A or B of Example 19; (2) adding a sample to one of the fluid compartments; and (3) measuring at least one of an electrical potential difference and a current across at least a portion of the sample, using the electrodes.

F. A method for analyzing samples such as cells, vesicles, and cellular organelles, and fragments, derivatives, and mixtures thereof, comprising (1) selecting a carrier having a plurality of apertures, a first sample being sealed across a first aperture, and a second sample being sealed across a second aperture, wherein fluid is disposed on opposite sides of the first and second apertures, and (2) measuring at least one of an electrical potential difference and a current, across at least a portion of the first and second samples.

1. The method of paragraph E/F, the sample being bound to the aperture, further comprising permeabilizing a portion of the sample to facilitate measurement of an electrical property of a remaining portion of the sample.

2. The method of paragraph 1, wherein the step of permeabilizing includes adding a pore former to at least one compartment.

3. The method of paragraph 1, the sample being a cell, a vesicle, or a biological organelle, wherein the step of permeabilizing includes permeabilizing the portion of the sample bound across and facing the aperture.

4. The method of paragraph 1, the sample being a cell, a vesicle, or a biological organelle, wherein the step of permeabilizing includes destroying the portion of the sample bound across and facing the aperture.

5. The method of paragraph 1, the sample being a cell, a vesicle, or a biological organelle, wherein the step of permeabilizing includes permeabilizing the portion of the sample facing the fluid compartment.

6. The method of paragraph E/F, further comprising applying an electrical potential difference across the portion of the sample, and measuring the current necessary for maintaining the applied electrical potential difference.

7. The method of paragraph 6, further comprising repeating the steps of applying an electrical potential difference and measuring the current for a second sample positioned about a second aperture.

8. The method of paragraph 7, wherein the steps of applying and measuring are performed sequentially on the first and second samples.

9. The method of paragraph 7, wherein the steps of applying and measuring are performed in parallel on the first and second samples.

10. The method of paragraph 6, further comprising computing a quantity indicative of the conductivity of the sample based on the applied electrical potential difference and the measured current.

11. The method of paragraph 10, further comprising correlating the computed conductivity with the conformation state of a channel-forming protein present in the sample.

12. The method of paragraph 6, wherein the step of measuring the current includes monitoring current fluctuations.

13. The method of paragraph 12, wherein the step of monitoring current fluctuations includes at least one of monitoring the amplitudes and residence times of the fluctuations.

14. The method of paragraph 6, further comprising adding an agonist to the compartment containing the sample, wherein the steps of applying an electrical potential difference and measuring the current are repeated before and after the step of adding the agonist.

15. The method of paragraph E/F, further comprising applying an a current across the portion of the sample, and measuring the electrical potential difference necessary for maintaining the applied current.

16. The method of paragraph E/F, wherein the step of adding the sample includes introducing the sample into the compartment through an inlet opening arranged concentrically above the aperture.

17. The system of paragraph 16, wherein the sample arrives near the aperture by at least one of convection and sedimentation.

18. The system of paragraph 16, wherein the sample is moved onto the aperture electrophoretically.

19. The method of paragraph E/F, further comprising allowing the sample to bind to the carrier across the aperture.

20. The method of paragraph E/F, further comprising moving the sample onto the aperture electrophoretically.

21. The method of paragraph E/F, the sample being a cell, further comprising the step of isolating the sample from a population of samples prior to the steps of adding a sample and applying an electrical potential difference.

22. The method of paragraph E/F, the sample being a cell, further comprising the step of transforming the sample prior to the steps of adding a sample and applying an electrical potential difference.

23. The method of paragraph E/F, the sample being a cell from a cell line, further comprising the step of cultivating the cell line prior to the steps of adding a sample and applying an electrical potential difference.

24. The method of paragraph E/F, further comprising the step of purifying the sample prior to the steps of adding a sample and applying an electrical potential difference.

25. The method of paragraph 24, wherein the step of purifying the sample includes separating members of the sample according to size.

26. The method of paragraph 25, wherein the step of separating members of the sample according to size includes dialyzing the sample.

27. The method of paragraph E/F, the sample being a vesicle, further comprising the step of forming the vesicle prior to the steps of adding a sample and applying an electrical potential difference.

28. The method of paragraph E/F, further comprising modifying at least one of the sample and the carrier to enhance binding between the sample and the carrier.

29. The method of paragraph 28, wherein the step of modifying includes treating at least one of the sample and the carrier to enhance electrostatic interactions.

30. The method of paragraph 28, wherein the step of modifying includes treating at least one of the sample and the carrier to enhance molecule-specific interactions.

31. The method of paragraph 28, wherein the step of modifying includes treating at least one of the sample and the carrier to enhance multivalent-ion-mediated interactions.

32. The method of paragraph 31, wherein the step of treating includes adding $Ca^{2+}$ to the sample medium.

33. The method of paragraph 28, wherein the step of modifying includes treating at least one of the sample and the carrier to enhance hydrophilic/hydrophobic interactions.

34. The method of paragraph E/F, further comprising cleaning the carrier in an oxygen plasma.

35. The method of paragraph E/F, further comprising replacing a solution in at least one compartment with another solution.

36. The method of paragraph E/F, further comprising checking the fluid level in at least one compartment.

37. The method of paragraph 36, wherein the step of checking is performed continuously or regularly.

38. The method of paragraph 36, further comprising correcting the fluid level according to a preset filling parameter, if an error is detected during checking.

39. The method of paragraph E/F, further comprising adding a substance of interest to at least one compartment.

40. The method of paragraph E/F, further comprising adding a pore former to at least one compartment, thereby increasing the electrical conductivity or permeability of the sample toward certain ions.

41. The method of paragraph 40, wherein the pore former is selected from the group consisting of amphotericin B or nystatin.

42. The method of paragraph E/F, further comprising adding proteoliposomes to at least one compartment, wherein the proteoliposomes fuse with the sample above the aperture, so that membrane proteins contained in the proteoliposomes are accessible to electrical or optical measurements.

43. The method of paragraph E/F, further comprising incorporating membrane proteins into the sample above the aperture, after the sample is bound to the aperture.

44. The method of paragraph 40, wherein the membrane proteins are selected from the group consisting of ligand-controlled and G-protein-coupled receptors.

45. The method of paragraph E/F, further comprising carrying out an optical measurement on the sample.

46. The method of paragraph 45, wherein the optical measurement is a fluorescence measurement.

47. The method of paragraph E/F, further comprising repeating the steps of adding a sample and applying an electrical potential difference for a second sample and a second compartment.

48. The method of paragraph E/F, there being samples positioned across at least two apertures, wherein measurements are performed sequentially over the at least two apertures.

49. The method of paragraph E/F, there being samples positioned across at least two apertures, wherein measurements are performed in parallel over the at least two apertures.

50. The method of paragraph E/F, further comprising (1) adding a second sample to a second one of the fluid compartments; and (2) measuring at least one of an electrical potential difference and a current across at least a portion of the second sample, using the electrodes.

51. The method of paragraph 50, the sample being a first sample, where the steps of measuring are performed sequentially for the first and second samples.

52. The method of paragraph 50, the sample being a first sample, where the steps of measuring are performed simultaneously for the first and second samples.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

[i] J. P. Changeux (1993), "Chemical Signaling in the Brain," *Sci. Am.* Nov. Pages 30 ff; A. G. Gilman (1995), *Angew. Chem. Int. Ed. Engl.* 34:1406-1428; M. Rodbell (1995), *Angew. Chem. Int. Ed. Engl.* 34: 1420-1428.

[ii] J. Hodgson (1992), *Bio/Technology* 9:973.

[ii] J. Knowles (1997), "Medicines for the New Millennium Hunting Down Deseases [sic: Diseases]." *Odyssey* Vol. 3(1).

[iv] O. P. Hamill, A. Marty, et al. (1981), "Improved Patch-clamp Techniques for High-resolution Current Recording from Cells and Cell-free Membrane Patches". *Pflugers Arch* 391(2):85-100.

[v] (Radler, J., H. Strey, et al. (1995), "Phenomenology and Kinetics of Lipid Bilayer Spreading on Hydrophilic Surfaces." *Langmuir* 11(11):4539-4548.

[vi] For example, polycations, such as described by Mazia, Schatten, et al. (see D. Mazia, G. Schatten et al. (1975), "Adhesion of Cells to Surfaces Coated with Polylysine." *J. Cell Biol.* 66:198-200).

[vii] J. Edelstein, O. Schaad, J. -P. Changeux (1997), "Single Binding versus Single Channel Recordings: A New Approach to Study Ionotropic Receptors." *Biochemistry* 36:13755-13760.

[viii] See Hamill, Marty, et al. (1981), loc. cit.; J. G. Nicholls, A. R. Martin, et al. (1992), *From Neuron to Brain: A Cellular and Molecular Approach to the Function of the Nervous System*. Sunderland, Mass., Sinauer Associates, Inc.

[ix] R. Horn, A. Marty (1988), "Muscarinic Activation of Ionic Currents Measured by a New Whole-cell Recording Method," *J. Gen. Physiol.* 92(2):145-59; J. Rae, K. Cooper, et al. (1991), "Low Access Resistance Perforated Patch Recordings Using Amphotericin B." *J. Neurosci. Methods* 37(1): 15-26.

[x] Z. M. Pei, J. M. Ward, et al. (1996), "A Novel Chloride Channel in Vicia Faba Guard Cell Vacuoles Activated by the Serine/Theonine Kinase, CDPK." *EMBO J.* 15(23): 6564-74.

[xi] See, e.g., R. B. Gennis (1989), *Biomembranes: Molecular Structure and Function*. New York, Springer Verlag.

[xii] H. H. Hub, U. Zimmerman, et al. (1982), "Preparation of Large Unilamellar Vesicles." *FEBS Lett.* 140(2):254-256; P. Mueller, T. F. Chien, et al.(1983), "Formation and Properties of Cell-like Lipid Bilayer Vesicles." *Biophys. J.* 44(3):375-81, K. Akashi, H. Miyata, et al. (1996), "Preparation of Giant Liposomes in Physiological Conditions and their Characterization under an Optical Microscope." *Biophys. J.* 71(6):3242-50

[xiii] M. Criado and B. U. Keller (1987), "A Membrane Fusion Strategy for Single-channel Recordings of Membranes Usually Non-accessible to Patch-clamp Pipette Electrodes." *FEBS Lett.* 224(1):172-6; B. U. Keller, R. Hedrich, et al. (1988), "Single-channel Recordings of Reconstituted Ion Channel Proteins: An Improved Technique." *Pflugers Arch* 411(1):94-100.

[xiv] See Mazia, Schatten, et al. loc. cit., 1975.

[xv] M. L. Williamson, D. H. Atha, et al. (1989), "Anti-T2 Monoclonal Antibody Immobilization on Quartz Fibers: Stability and Recognition of T2 Mycotoxin." *Analytical Letters* 22(4):803-816.

[xvi] B. Sakmann and E. Neher (1983), *Single-channel Recording*, New York, Plenum Press.

[xvii] R. B. Gennis (1989), *Biomembranes: Molecular Structure and Function*, New York, Springer Verlag.

[xviii] T. Schürholz, J. Kehne et al. (1992), "Functional Reconstitution of the Nicotinic Acetylcholine Receptor by CHAPS Dialysis Depends on the Concentration of Salt, Lipid, and Protein," *Biochemistry* 31(21):5067-77; Schürholz, T. (1996), "Critical Dependence of the Solubilization of Lipid Vesicles by the Detergent CHAPS on the Lipid Composition. Functional Reconstitution of the Nicotinic Acetylcholine Receptor into Preformed Vesicles above the Critical Micellization Concentration," *Biophys. Chem.* 58(1-2):87-96).

[xix] See Eray, Dogan, et al. (1995) loc. cit.

[xx] R. A. North (1994), *Ligand- and Voltage-gated Ion Channels*, CRC Press; S. J. Peroutka, (1991), *Serotonin Receptor Subtypes-Basic and Clinical Aspects*, New York, John Wiley; Peroutka, S. J. (1994), *G-protein-coupled Recep-* tors, CRC Press; E. C. Conley, (1996), *The Ion Channel Facts Book*, Academic Press.

We claim:

1. A system for analyzing the presence or activity of ion channels in membranous samples, comprising:
    a carrier having an aperture and a substantially planar seal surface circling the aperture;
    first and second fluid compartments, separated by the carrier, and fluidically connected to one another, in the absence of a membranous sample, via the aperture;
    a membranous sample, selected from the group consisting of cells, organelles, and vesicles, sealed across the aperture, wherein the seal has an electrical resistance of greater than about 1GΩ;
    first and second electrodes, in electrical contact with the first and second fluid compartments, respectively, wherein the first and second electrodes are adapted to apply and/or measure at least one of an electrical potential and a current from at least a portion of the membranous sample sealed across the aperture within the seal surface; and
    a sample-analysis mechanism adapted to perform a fluorescence measurement on a sample positioned about the aperture.

2. The system of claim 1, wherein the sample is a cell.

3. The system of claim 1, wherein the carrier is at least substantially planar.

4. The system of claim 1, wherein the carrier is formed at least in part of silicon.

5. The system of claim 1, wherein the carrier includes first and second layers having different compositions.

6. The system of claim 1, wherein the carrier has first and second sides facing the first and second fluid compartments, respectively, and wherein at least one of the sides is at least substantially planar.

7. The system of claim 1, wherein the aperture is characterized by an aperture axis that extends between opposite ends of the aperture, and wherein the carrier includes at least one surface that is at least substantially perpendicular to the aperture axis.

8. The system of claim 1, wherein the carrier comprises a ledge.

9. The system of claim 1, wherein at least a portion of the carrier is annular in shape.

10. The system of claim 1, wherein a surface of the carrier is modified to promote sample adhesion.

11. The system of claim 10, wherein the surface is electrically charged.

12. The system of claim 10, wherein the surface is hydrophilic.

13. The system of claim 10, wherein the surface is plasma cleaned before the carrier is modified or immediately before the carrier is used.

14. The system of claim 1, wherein the carrier includes a plurality of apertures.

15. The system of claim 1, wherein the membranous sample is positioned at least substantially outside the aperture.

16. The system of claim 1, wherein the membranous sample is positioned at least substantially inside the aperture.

17. The system of claim 1, wherein the aperture is formed at least in part by anisotropic etching.

18. The system of claim 1 further comprising a sample-handling mechanism configured to add at least one of a sample and a fluid to at least one of the fluid compartments.

19. The system of claim 18, wherein the sample-handling mechanism is configured to introduce samples into at least one compartment through an opening arranged above the aperture.

20. The system of claim 18, wherein the sample-handling mechanism is configured to check the fluid level in at least one compartment.

21. A system for analyzing the presence or activity of ion channels in membranous samples, comprising:
    a carrier having an opening and a substantially planar seal surface circling the aperture;
    first and second fluid compartments, separated by the carrier, and fluidically connected to one another, in the absence of a membrane sample, via the opening;
    first and second electrodes, in electrical contact with the first and second fluid compartments, respectively, wherein the first and second electrodes being adapted to apply and/or measure at least one of an electrical potential and a current from at least a portion of a membranous sample sealed within the opening;
    a membranous sample, selected from the group consisting of cells, organelles, and vesicles, sealing the opening within the seal surface; and
    a sample-analysis mechanism adapted to perform a fluorescence measurement on a sample positioned about the aperture.

22. The system of claim 21, wherein the sample seals the opening with an electrically tight bond.

23. The system of clam 21, wherein the opening has a wall surrounding an interior.

24. The system of claim 21, wherein the interior of the opening further includes a funnel structure.

25. The system of claim 21, wherein the opening includes the first or second or both fluid compartments.

26. A system for analyzing the presence or activity of ion channels in membranous samples, comprising:
    a carrier having a planar surface, an aperture at the planar surface, and a substantially planar seal surface circling the aperture;
    first and second fluid compartments, separated by carrier, and fluidically connected, in the absence of a sample, via the aperture;
    a membranous sample, selected from the group consisting of cells, organelles, and vesicles, sealed across the aperture, wherein the seal has an electrical resistance of greater than about 1 gigaohm;
    first and second electrodes, in electrical contact with the first and second fluid compartments, respectively, wherein the first and second electrodes are adapted to apply and/or measure at least one of an electrical potential and a current from at least a portion of the membranous sample sealed across the aperture within the seal surface; and
    a sample-analysis mechanism adapted to perform fluorescence measurement on a sample positioned about the aperture.

27. The system of claim 26, where the membranous sample is a cell.

28. The system of claim 26, wherein the planar surface is a first planar surface, and wherein the carrier includes a second planar surface, at least generally parallel to the first planar surface.

29. The system of claim 28, wherein the aperture has two ends, and wherein a first end terminates at the first planar surface, and a second end terminates at least generally at the second surface.

30. The system of claim 28, where n the aperture is characterized by an aperture axis that extends between opposite ends of the aperture, and wherein the aperture axis is at least substantially perpendicular to the first and second surfaces.

31. The system of claim 26, wherein the carrier includes first and second layers having different compositions, and wherein the aperture traverses the first and second layers.

32. The system of claim 26, wherein a surface of at least one of the layers is modified to promote sample adhesion.

33. The system of claim 26, wherein the carrier includes a plurality of apertures, each aperture disposed in a planar surface.

34. The system of claim 26 further comprising a sample-handling mechanism configured to add at least one of a sample and a fluid to at least one of the fluid compartments.

35. A system for analyzing the presence or activity of ion channels in membranous samples, comprising:
   a carrier comprising (i) a pluralilly of layers, the plurality including at least a first layer and a second layer having different compositions, (ii) an aperture that traverses the first and second layers, and (iii) and a substantially planar seal surface circling the aperture;
   first and second fluid compartments, separated by the carrier, and fluidically connected to one another, in the absence of a sample, via the aperture;
   a membranous sample, selected from die group consisting of cells, organelles, and vesicles, sealed across the aperture;
   first and second electrodes, in electrical contact with the first and second fluid compartments, respectively, wherein the first and second electrodes are adapted to apply and/or measure at least one of an electrical potential and a current from at least a portion of the membranous sample sealed across the aperture within the seal surface; and
   a sample-analysis mechanism adapted to perform a fluorescence measurement on a sample positioned about the aperture.

36. The system of claim 35, wherein the carrier is at least substantially planar.

37. The system of claim 36, wherein the aperture spans the space between opposed surfaces of the carrier, and wherein, adjacent the aperture, the first and second layers are at least substantially parallel to the opposed surfaces.

38. The system of claim 36, wherein the aperture is characterized by an aperture axis that extends between opposite ends of the aperture, and wherein the aperture axis is at least substantially perpendicular to the plane of the carrier.

39. The system of claim 35, wherein the seal between the sample and the aperture has an electrical resistance of at least about 1 gigaohm.

40. The system of claim 35, wherein at least one of the first and second layers includes silicon.

41. The system of claim 35, wherein the aperture is at least substantially tapered in the first layer and at least substantially cylindrical in the second layer.

42. The system of claim 35, wherein the average diameter of the aperture in at least one of the first and second layers is comparable to the average thickness of the layer.

43. The system of claim 35, wherein the first and second layers have different thicknesses.

44. The system of claim 35, wherein the first and second layers have different etchabilities.

45. The system of claim 35, wherein a surface of at least one of the layers is modified to promote sample adhesion.

46. The system of claim 35, wherein the carrier includes a plurality of apertures, each of the apertures traversing the first and second layers.

47. The system of claim 35 further comprising a sample-handling mechanism configured to add at least one of a sample and a fluid to at least one of the fluid compartments.

48. A system for analyzing the presence or activity of ion channels in membranous samples, comprising:
   a earner comprising (i) an aperture, (ii) a substatially planar seal surface circling the aperture, and (iii) a binding surface associated with the aperture, the binding surface being adapted to bind a membranous sample such that the sample seals across the aperture;
   first and second fluid compartments, separated by the carrier, and fluidically connected to one another, in the absence of a sample, via the aperture;
   a membranous sample, selected from the group consisting of cells, organelles, and vesicles, bound to the binding surface, and sealed across the aperture within the seal surface;
   first and second electrodes, in electrical contact with the first and second fluid compartments, respectively, wherein the first and second electrodes are adapted to apply and/or measure at least one of an electrical potential and a current from at least a portion of the membranous sample sealed across the aperture; and
   a sample-analysis mechanism adapted to perform a fluorescence measurement on a sample positioned about the aperture.

49. The system of claim 48, wherein the carrier is at least substantially planar.

50. The system of claim 48, wherein the binding surface is adjacent the aperture.

51. The system of claim 48, wherein the binding surface is within the aperture.

52. The system of claim 48, wherein the seal between the sample and the aperture has an electrical resistance of at least about 1 gigaohm.

53. The system of claim 48, wherein the binding surface is electrically charged, such that it attracts biological membranes.

54. The system of claim 53, wherein the electrical charge is produced with the aid of polycations and/or silanes.

55. The system of claim 48, wherein the binding surface provides a molecule-specific bonding of cells, vesicles, or biological organelles.

56. The system of claim 55, wherein the molecule-specific bonding is mediated by biotin-streptavidin interactions or histidine-nitriloacetic acid interactions.

57. The system of claim 48, wherein the binding surface provides a multivalent-ion-mediated bonding of cells, vesicles, or biological organelles.

58. The system of claim 57, wherein the multivalent-ion-mediated bonding is modiayed by $Ca^{2+}$ions.

59. The system of claim 48, wherein the binding surface has hydrophilic and hydrophobic regions, and wherein the hydrophilic regions are disposed around the apertures.

60. The system of claim 48, wherein the carrier is plasma cleaned before the surface of the carrier is modified or immediately before the carrier is used.

61. The system of claim 48, wherein the sample is modified to enhance bonding between the sample and the carrier.

62. The system of claim 61, wherein the binding surface is charged, and wherein the sample is modified by charging its surface with a charge opposing that on the binding surface.

63. The system of claim 48, wherein the carrier includes a plurality of apertures, each of the apertures being adjacent a binding surface adapted to bind a sample such that the sample seals across the corresponding aperture.

64. The system of claim 48 further comprising a sample-handling mechanism configured to add at least one of a sample and a fluid to at least one of the fluid compartments.

* * * * *